United States Patent
Hauptman et al.

(10) Patent No.: US 11,398,243 B2
(45) Date of Patent: Jul. 26, 2022

(54) VERBAL PERIODIC SCREENING FOR HEART DISEASE

(71) Applicant: CardioKol Ltd., Modiln (IL)

(72) Inventors: Yirmiyahu Hauptman, Rishon-LeZion (IL); Alon Goren, Moshav Ben-Shemen (IL); Eli Attar, Rosh HaAyin (IL); Pinhas Sabach, Jerusalem (IL)

(73) Assignee: CardioKol Ltd., Modiln (IL)

( * ) Notice: Subject to any disclaimer, the term of this patent is extended or adjusted under 35 U.S.C. 154(b) by 118 days.

(21) Appl. No.: 16/485,173

(22) PCT Filed: Feb. 12, 2018

(86) PCT No.: PCT/IL2018/050162
§ 371 (c)(1),
(2) Date: Aug. 12, 2019

(87) PCT Pub. No.: WO2018/146690
PCT Pub. Date: Aug. 16, 2018

(65) Prior Publication Data
US 2019/0362740 A1 Nov. 28, 2019

Related U.S. Application Data

(60) Provisional application No. 62/457,914, filed on Feb. 12, 2017.

(51) Int. Cl.
*G10L 25/66* (2013.01)
*A61B 5/00* (2006.01)
(Continued)

(52) U.S. Cl.
CPC ............ *G10L 25/66* (2013.01); *A61B 5/4803* (2013.01); *G10L 17/26* (2013.01); *A61B 5/0022* (2013.01); *A61B 5/7264* (2013.01); *G10L 15/22* (2013.01)

(58) Field of Classification Search
None
See application file for complete search history.

(56) References Cited

U.S. PATENT DOCUMENTS

| 4,377,158 A | 3/1983 | Friedman et al. |
| 5,671,330 A | 9/1997 | Sakamoto et al. |

(Continued)

FOREIGN PATENT DOCUMENTS

| JP | H05-066774 | 3/1993 |
| JP | H05-329118 | 12/1993 |

(Continued)

OTHER PUBLICATIONS

Nivedita, Deshpande, Thakur Kavita, and A. S. Zadgaonkar. "First degree heart block determination from speech analysis." 2013 International Conference on Signal Processing, Image Processing & Pattern Recognition. IEEE, 2013. (Year: 2013).*

(Continued)

*Primary Examiner* — Brian L Albertalli

(57) ABSTRACT

A method for analyzing a voice sample of a subject to determine a cardiac condition, for example, an arrhythmic condition, comprising extracting at least one voice feature from the voice sample, detecting an effect of the cardiac condition on the at least one voice feature and determining the cardiac condition based on the effect. Disclosed is also a system for determining the cardiac condition in the voice sample provided by the subject. Related apparatus and methods are also described.

21 Claims, 32 Drawing Sheets

(51) Int. Cl.
  *G10L 17/26*     (2013.01)
  *G10L 15/22*     (2006.01)

(56) References Cited

U.S. PATENT DOCUMENTS

| | | | |
|---|---|---|---|
| 7,398,213 | B1 | 7/2008 | Levanon et al. |
| 7,917,366 | B1 | 3/2011 | Levanon et al. |
| 8,078,470 | B2 | 12/2011 | Levanon et al. |
| 8,249,875 | B2 | 8/2012 | Levanon et al. |
| 8,768,708 | B2 | 7/2014 | Levanon et al. |
| 10,796,805 | B2 * | 10/2020 | Lotan .................. G16B 40/00 |
| 2003/0120490 | A1 * | 6/2003 | Budde .................. G10L 15/063 704/254 |
| 2008/0045805 | A1 | 2/2008 | Sarel et al. |
| 2012/0095357 | A1 * | 4/2012 | Tran ..................... A61B 8/00 600/509 |
| 2012/0220899 | A1 | 8/2012 | Oh et al. |
| 2012/0265024 | A1 | 10/2012 | Shrivastav et al. |
| 2013/0138002 | A1 | 5/2013 | Weng et al. |
| 2014/0122063 | A1 | 5/2014 | Gomez Vilda et al. |
| 2015/0216448 | A1 | 8/2015 | Lotan et al. |
| 2016/0196837 | A1 | 7/2016 | Levanon |
| 2017/0007167 | A1 * | 1/2017 | Kostic .................. A61B 5/742 |
| 2017/0053665 | A1 * | 2/2017 | Quatieri, Jr ............ G10L 25/66 |
| 2020/0229708 | A1 * | 7/2020 | Bonomi ................ A61B 5/0205 |

FOREIGN PATENT DOCUMENTS

| | | |
|---|---|---|
| JP | H06-205847 | 7/1994 |
| JP | 2000-287943 | 10/2000 |
| JP | 2009-301125 | 12/2009 |
| JP | 2016-043041 | 4/2016 |
| WO | WO 2014/037937 | 3/2014 |
| WO | WO 2014/163584 | 10/2014 |
| WO | WO 2015/010129 | 1/2015 |
| WO | WO 2016/035070 | 3/2016 |
| WO | WO 2017/068581 | 4/2017 |
| WO | WO 2018/146690 | 8/2018 |

OTHER PUBLICATIONS

Pareek, Vishakha, and R. K. Sharma. "Coronary heart disease detection from voice analysis." 2016 IEEE Students' Conference on Electrical, Electronics and Computer Science (SCEECS). IEEE, 2016. (Year: 2016).*
Sakai, Motoki. "Estimation of heart rate from vocal frequency based on support vector machine,". International Journal of Advances in Scientific Research 2.1 (2016): 16-22. (Year: 2016).*
Mesleh, Abdelwadood, et al. "Heart rate extraction from vowel speech signals." Journal of computer science and technology 27.6 (2012): 1243-1251. (Year: 2012).*
Sakai, Motoki. "Modeling the relationship between heart rate and features of vocal frequency." International Journal of Computer Applications 120.6 (2015). (Year: 2015).*
Ryskaliyev, Aibek, Sanzhar Askaruly, and Alex Pappachen James. "Speech signal analysis for the estimation of heart rates under different emotional states." 2016 International Conference on Advances in Computing, Communications and Informatics (ICACCI). IEEE, 2016. (Year: 2016).*
Kaur, Jaswinder, and Rupinder Kaur. "Extraction of heart rate parameters using speech analysis." International Journal of Science and Research 3.10 (2014): 13741376. (Year: 2014).*
James, Alex Pappachen. "Heart rate monitoring using human speech spectral features." Human-centric Computing and Information Sciences 5.1 (2015): 1-12. (Year: 2015).*
Schuller, Björn, Felix Friedmann, and Florian Eyben. "Automatic recognition of physiological parameters in the human voice: Heart rate and skin conductance." 2013 IEEE International Conference on Acoustics, Speech and Signal Processing. IEEE, 2013. (Year: 2013).*
Tsiartas, Andreas, et al. "Prediction of heart rate changes from speech features during interaction with a misbehaving dialog system." Sixteenth Annual Conference of the International Speech Communication Association. 2015. (Year: 2015).*
International Preliminary Report on Patentability dated Aug. 22, 2019 From the International Bureau of WIPO Re. Application No. PCT/IL2018/050162. (12 Pages).
International Search Report and the Written Opinion dated May 25, 2018 From the International Searching Authority Re. Application No. PCT/IL2018/050162. (13 Pages).
De Oliveira Dias "Estimation of the Glottal Pulse From Speech or Singing Voice", Master's Thesis Submitted in Partial Fulfillment of the Requirements for the Degree of Master in Biomedical Engineering, School of Engineering of the University of Porto, Portugal, p. 1-39, Jul. 2012.
Deshpande et al. "Assessment of Heart Rate Variability From Speech Analysis", 167th Meeting of the Acoustical Society of America, Providence, RI, USA, May 5-9, 2014, Proceedings of Meetings on Acoustics, Session 5aSP: Signal Processing in Acoustics, 21: 055004-1-055004-8, May 20, 2014.
Deshpande et al. "Assessment of Systolic and Diastolic Cycle Duration From Speech Analysis in the State of Anger and Fear", Computer Science & Information Technology, CS & IT, 04: 137-141, 2012.
Dias et al. "Glottal Pulse Estimation—A Frequency Domain Approach", Retrieved From the Internet, Unpublished, 4 P., 2014.
Drugman "Advances in Glottal Analysis and Its Applications", PhD Thesis to Obtain the Title of PhD in Applied Sciences, Speciality: Speech Processing, University of Mons, Doctoral School Musics, Signal Processing, Faculty of Engineering, TCTS Lab, Belgium, p. 1-235, 2011.
James "Heart Rate Monitoring Using Human Speech Spectral Features", Human-Centric Computing and Information Sciences, 5(33): 1-12, 2015.
Kaplan et al. "Heartrate Measurement From Human Voice", SIPL, Poster Presentation, 13 P., 2017.
Kaur et al. "Extraction of Heart Rate Parameters Using Speech Analyis", International Journal of Science and Research, 3(10): 1374-1376, Oct. 2014.
Lei et al. "Discrete Wavelet Transform Decomposition Level Determination Exploiting Sparseness Measurement", International Journal of Electrical, Computer, Energetic, Electronic and Communication Engineering, 7(9): 1182-1185, Sep. 25, 2013.
Mbitiru et al. "Analysis of Stress in Speech Using Empirical Mode Decomposition", Proceedings of the 2008 IAJC-IJME International Conference, Paper 140, ENG 101, p. 140-146, 2008.
Mesleh et al. "Heart Rate Extraction From Vowel Speech Signals", Journal of Computer Science and Technology, 27(6): 1243-1251, Nov. 2012.
Reilly et al. "Voice Pathology Assessment Based on A Dialogue System and Speech Analysis", Proceedings of the AAAI Fall Symposium on Dialogue Systems for Health Communication, Washington DC, USA, p. 104-109, Oct. 2004.
Ryskaliyev et al. "Speech Signal Analysis for the Estimation of Heart Rates Under Different Emotional States", arXiv Preprint arXiv:1608.03720v1, 7 P., Aug. 16, 2016.
Sakai "Estimation of Heart Rate From Vocal Frequency Based on Support Vector Machine", International Journal of Advances in Scientific Research, 2(01): 016-022, Jan. 30, 2016.
Sakai "Modeling the Relationship Between Heart Rate and Features of Vocal Frequency", International Journal of Computer Applications, 120(6): 32-37, Jun. 2015.
Schuller et al. "The Munich Biovoice Corpus: Effects of Physical Exercising, Heart Rate, and Skin Conductance on Human Speech Production", LREC, p. 1506-1510, May 26, 2014.
Skopin et al. "Heartbeat Feature Extraction From Vowel Speech Signal Using 2D Spectrum Representaton", Proceedings of the 4th International Conference on Information Technology, ICIT, Amman, Jordan, 6 P., Jun. 2009.
Thakur et al. "Assistive Technology for Heart Monitoring of Elderly People Through Speech Analysis", Optimizing Assistive Technologies for Aging Populations, 14(Chap.13): 335-1-335-21, Sep. 2015.
Supplementary European Search Report and the European Search Opinion dated Nov. 18, 2020 From the European Patent Office Re. Application No. 18750913.8. (7 Pages).

(56) References Cited

OTHER PUBLICATIONS

Askaruly "Speech Signal Analysis for the Estimation of Heart Abnormalities", Bachelor of Engineering (Electrical & Electronic), P05574389, Nazarbavev University, Nur-Sultan, Kazakhastan, p. 1-45, May 12, 2016.
Sakai "Feasibility Study on Blood Pressure Estimations From Voice Spectrum Analysis", International Journal of Computer Applications, XP055747513, 109(7): 39-43, Jan. 2015.
Notice of Reason(s) for Rejection dated Feb. 8, 2022 From the Japan Patent Office Re. Application No. 2019-565085 and Its Translation Into English. (20 Pages).

\* cited by examiner

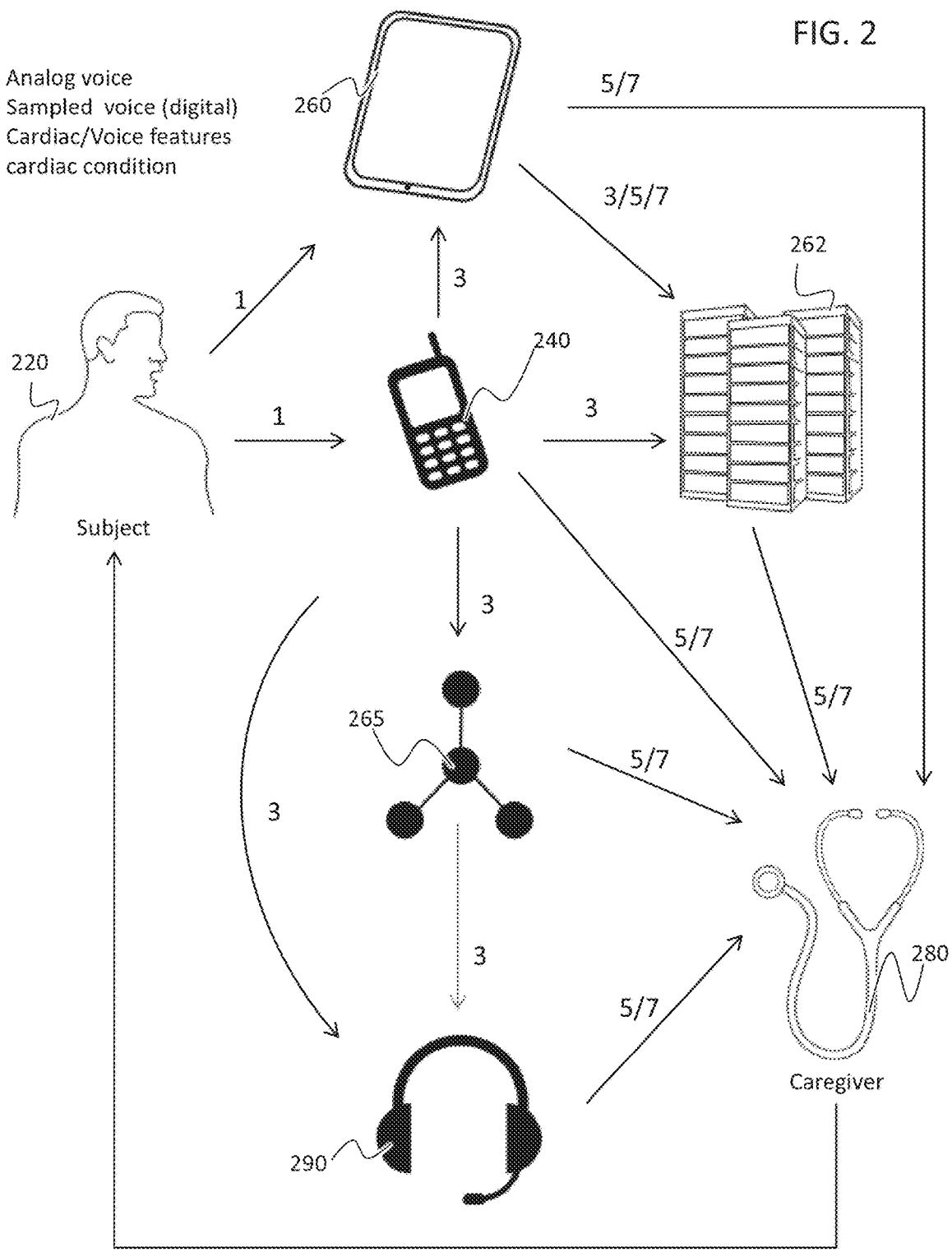

Tw=50, Ts=10

VERBAL PERIODIC SCREENING FOR HEART DISEASE

RELATED APPLICATIONS

This application is a National Phase of PCT Patent Application No. PCT/IL2018/050162 having International filing date of Feb. 12, 2018, which claims the benefit of priority under 35 USC § 119(e) of U. S. Provisional Patent Application No. 62/457,914 filed on Feb. 12, 2017. The contents of the above applications are all incorporated by reference as if fully set forth herein in their entirety.

FIELD AND BACKGROUND OF THE INVENTION

The present invention, in some embodiments thereof, relates to medical diagnosis using voice and, more particularly, but not exclusively, to estimating cardiac conditions based on human voice.

U.S. Patent Application Publication No. US2012/0220899 discloses a method and apparatus for diagnosing a user's health state. The apparatus includes including a voice detecting unit which detects and monitors a user's voice; a voice analyzing unit which extracts a voice feature from a voice detected by the voice detecting unit, based on a health state to be diagnosed; a voice diagnosing unit which diagnoses a health state of the user by comparing the voice feature extracted by the voice analyzing unit with an abnormal state reference, and which monitors a change in the health state; and a diagnosis outputting unit which outputs information regarding the health state and a health state change diagnosed by the voice diagnosing unit.

U.S. Patent Application Publication No. US2014/0122063 discloses a method and computing system for recording and analyzing the voice which allows a series of parameters of phonation to be calculated. These transmit relevant information regarding effects caused by organic disorders (which affect the physiology of the larynx) or neurological disorders (which affect the cerebral centers of speech). The classification methods are also considered an essential part of the invention which allow estimations of the existing dysfunction to be obtained and for the allocation of personality.

Additional background art includes:

An article titled: "Glottal Pulse Estimation—A Frequency Domain Approach" by Sandra Dias and Anibal Ferreira, of the Department of Electrical and Computer Engineering, University of Porto—Faculty of Engineering, Porto, Portugal, published on the World Wide Web in www(dot)ortra(dot)com/events/Portals/16/Dias %20et %20a_AfekaCon fSP2014(dot)pdf;

a Master's Thesis submitted to the School of Engineering of the University of Porto titled: "Estimation of the glottal pulse from speech or singing voice" by Sandra de Oliviera Dias, in July 2012.

an article titled "Discrete Wavelet Transform Decomposition Level Determination Exploiting Sparseness Measurement", by Lei Lei, Chao Wang, and Xin Liu, published in International Journal of Electrical, Computer, Energetic, Electronic and Communication Engineering Vol:7, No:9, 2013;

A PhD thesis titled "Advances in Glottal Analysis and its Applications" by Thomas Drugmore to obtain the title of PhD in Applied Sciences of University of Mons;

U.S. Pat. No. 8,078,470;
U.S. Patent Application Publication No. US 2008/0045805;
U.S. Pat. No. 7,917,366;
U.S. Pat. No. 8,249,875;
U.S. Pat. No. 8,768,708;
International Application Publication No. WO 2016/035070;
International Application Publication No. WO 2014/037937; and
U.S. Pat. No. 7,398,213.

SUMMARY OF THE INVENTION

Example 1

A method for analyzing a voice sample of a subject to determine an arrhythmic cardiac condition, comprising:
extracting at least one voice feature from the voice sample;
detecting an effect of a blood flow on the at least one voice feature;
determining an arrhythmic cardiac condition based on the effect.

Example 2

The method according to example 1, wherein the determining an arrhythmic cardiac condition comprises integrating a plurality of the identified effect.

Example 3

The method according to any of examples 1-2, wherein the identifying an effect comprises identifying an effect of at least one of a timing of the blood flow, a periodicity of the blood flow and a magnitude or change in magnitude of the blood flow.

Example 4

The method according to example 1, further comprising classifying the voice sample to identify voiced segments.

Example 5

The method according to example 4, further comprising concatenating the voiced segments, such that at least some segments are removed and remaining segment ends are smoothed.

Example 6

The method according to any of examples 1-5, further comprising extrapolating data pertaining to the blood flow in segments which are removed from the voice sample.

Example 7

The method according to any of examples 1-6, wherein the detected effect comprises a timing of heart pulses.

Example 8

The method according to example 7, wherein the detecting an effect comprises identifying at least three consecutive occurrences of heart pulses.

In some embodiments detecting an effect by identifying three consecutive occurrences of heart pulses potentially takes a time approximately equivalent to three consecutive occurrences of heart pulses, or approximately 2-3 seconds. The detecting an effect of a cardiac condition in 2-3 seconds is compared to detecting by an ECG, which typically requires just a setup (placing electrodes) lasting more than 2-3 seconds.

Example 9

The method according to example 8, wherein the determining an arrhythmic cardiac condition comprises calculating time intervals between the at least three consecutive occurrences of heart pulses.

Example 10

The method according to example 9, wherein the determining an arrhythmic cardiac condition comprises matching the time intervals with reference time intervals obtained from a reference heart condition.

Example 11

The method according to example 10, wherein the determining further comprises:
determining a probability of the matching; and
comparing the probability to a threshold for determining the arrhythmic cardiac condition.

Example 12

The method according to example 11, wherein the reference heart condition is healthy or arrhythmic.

Example 13

The method according to any of examples 7-12, wherein the at least three occurrences of a heart pulse are not identified in the same voiced segment.

Example 14

The method according to any of examples 7-13, wherein the detecting an effect comprises identifying at least two consecutive occurrences of heart pulses.

In some embodiments detecting an effect by identifying two consecutive occurrences of heart pulses potentially takes a time approximately equivalent to two consecutive occurrences of heart pulses, or approximately 2 seconds.

Example 15

The method according to any of examples 1-14, wherein the detected effect comprises an effect of a magnitude, or a change in a magnitude of a heart pulse.

Example 16

The method according to example 15, wherein the detecting an effect comprises calculating a distribution of a plurality of values of the at least one voice feature.

Example 17

The method according to example 16, wherein the distribution includes standard deviation.

Example 18

The method according to any of examples 16-17, wherein the determining an arrhythmic cardiac condition based on the effect comprises comparing a characterizing parameter of the distribution to a threshold.

Example 19

The method according to example 18, wherein the characterizing parameter comprises a shape of the distribution.

Example 20

The method according to example 19, wherein the value comprises a width of the shape.

Example 21

The method according to any of examples 1-20, wherein the detected effect comprises an effect of a periodicity of heart pulses.

Example 22

The method according to any of examples 1-21, further comprising estimating a heart rate of the subject.

Example 23

The method according to example 22, wherein the determining an arrhythmic cardiac condition comprises characterizing the periodicity at a predetermined range around a frequency of the heart rate.

Example 24

The method according to example 23, wherein the characterizing comprises calculating a band width of a peak at the predetermined range.

Example 25

The method according to example 24, wherein the determining the arrhythmic cardiac condition comprises comparing the band width to a threshold.

Example 26

The method according to any of examples 1-25, further comprising validating the determining an arrhythmic cardiac condition.

Example 27

The method according to example 26, wherein the validating comprises obtaining a second voice sample comprising a predetermined vocalization.

Example 28

The method according to example 26, wherein the validating comprises at least one of an electrocardiogram test and a photoplethysmography test to the subject.

Example 29

The method according to any of examples 1-28, wherein the arrhythmic cardiac condition comprises atrial fibrillation.

Example 30

The method according to any of examples 1-29, wherein the voice sample is spontaneous speech.

Example 31

The method according to any of examples 1-30, wherein the voice sample comprises voices of a plurality of subjects.

Example 32

The method according to example 31, further comprising extracting voice segments of the subject from the voice sample.

Example 33

The method according to any of examples 1-32, wherein the voice feature includes a pitch.

Example 34

The method according to any of examples 1-33, wherein extracting said voice feature includes extracting Mel Frequency Cepstral Coefficients (MFCC).

Example 34.1

The method according to any of examples 1-34 wherein extracting the voice feature comprises calculating cross coherence. In some embodiments the cross-coherence is calculated at the pitch and\or formant frequencies. In some embodiments cross coherence is optionally calculated between one or more sets of two segments in the speech signal. In some embodiments a set (two segments) with lower coherence can optionally serve as indication of heart pulse that occurs during the segments.

In some embodiments cross coherence is calculated as follows:

$$\text{Speech\_frame}(m) = \{\text{Speech}(t+Ts*m), \text{Speech}((t+1)+Ts*m) \ldots \text{Speech}((t+Tw)+Ts*m)\}$$

Where:
"Ts"—is a time step between frames [sec]
"Tw"—is a duration of each frame [sec]
"m"— is a frame number
"t"—time
"Speech"—are the speech samples
"Speech_frame(m)"—is a frame of speech samples at time Ts*m $$\text{Coh}(m, m+T) = \text{CrossCoherence}(\text{Speech\_frame}(m), \text{Speech\_frame}(m+T))$$

Coh(m, m+T) is a cross coherence between frame "m" (at time m*Ts) and frame "m+T" at time ((m+T)*Ts)

Values of the coherence are in a range of 0 to 1, where 1 is a perfect match.

The above method optionally includes finding, for each frame m (at a time of Ts*m [sec]) a frame distance T where the coherence drops below a threshold. In some embodiments the threshold is between 0.1 to 0.98, for example 0.1, 0.2, 0.3, 0.4, 0.5, 0.6, 0.7, 0.8, 0.9, 0.95, 0.97 and 0.98.

In some embodiments the time T*Ts is an estimation of RR interval.

In some embodiments the overall cross coherence perturbation (width of distribution) optionally serves as an indication of AF. That is Speech with AF will have a wider distribution, a larger standard deviation,

Example 34.2

The method according to any of examples 1-33, wherein extracting said voice feature includes specific properties of the modulation spectrum.

In some embodiments, the properties of the spectrum of the acoustic feature, that is optionally calculated in each frame, serve as indication of pathological speech.

34.3

The method according to any of examples 1-34.2 wherein extracting the voice feature comprises performing analysis of the speech signal selected from a group consisting of:
wavelet analysis;
glottal pulse analysis; and
Linear Predictive Coding (LPC) analysis.

Example 35

The method according to any of examples 1-33 wherein the voice feature includes performing cross coherence between a period of the speech signal and another period of the speech signal.

Example 36

The method according to any of examples 1-35 wherein extracting the voice feature includes performing wavelet transform (WT).

Example 35

A system for determining an arrhythmic cardiac condition in a voice sample provided by a subject, comprising:
a voice input for obtaining a digital voice sample of the voice sample;
a voice feature extractor that extracts at least one voice feature from the digital voice sample;
a voice feature processor that identifies an effect of cardiac activity on the at least one voice feature;
a cardiac condition classifier that determines arrhythmic cardiac condition based on the effect.

Example 36

The system according to example 35, wherein the voice input forms a part of a mobile phone.

Example 37

The system according to example 35, wherein the voice input forms a part of a car multimedia system.

Example 38

The system according to any of examples 35-37, wherein at least one of the voice feature extractor, voice feature processor and cardiac condition classifier is located at a server.

Example 39

The system according to example 38, wherein the server is collocated with a telephone switch and gets the data from the switch.

Example 40

The system according to any of examples 35-39, wherein the voice input is configured to obtain the digital voice sample according to a predetermined schedule.

Example 41

The system according to any of examples 35-40, further comprising a permanent memory.

Example 42

The system according to example 41, wherein the memory stores reference voice features derived from a plurality of voice samples associated with an arrhythmic cardiac condition or a healthy cardiac condition.

Example 43

The system according to example 42, wherein the cardiac condition classifier determines the arrhythmic cardiac condition based on a training stage characterizing the reference voice features.

Example 44

The system according to example 41, wherein the permanent memory stores at least one previously collected voice sample from the subject.

Example 45

The system according to example 44, wherein the cardiac condition classifier determines the arrhythmic cardiac condition based on a change between the previously collected voice samples and the digital voice sample.

Example 46

A method for analyzing a voice sample of a subject to determine a cardiac condition, comprising:
extracting at least one voice feature from the voice sample;
detecting an effect of a blood flow on the at least one voice feature, the effect being at least one of a timing of the blood flow, a periodicity of the blood flow and a magnitude or change in magnitude of the blood flow;
determining a cardiac condition based on the effect.

Example 47

The method according to example 46, wherein the determined cardiac condition comprises an abnormal heart rate.

Example 48

The method according to example 47, wherein the abnormal heart rate includes ventricle tachycardia.

Example 49

The method according to example 46, wherein the determined cardiac condition comprises ectopic beats.

Example 50

The method according to example 49, wherein the determined cardiac condition having the ectopic beats comprises premature ventricular contraction.

Example 51

A method for analyzing a voice sample of a subject to reconstruct a cardiac behavior, comprising:
extracting at least one voice feature from the voice sample;
detecting an effect of a blood flow on the at least one voice feature; and
reconstructing one or more parameters of the cardiac behavior from the detected effect.

Example 52

The method according to example 51, wherein the cardiac behavior comprises an occurrence of cardiac fibrillation.

Example 53

The method according to example 52, comprising determining a presence of an arrhythmic cardiac condition when identifying more than a predetermined number of occurrences of cardiac fibrillation.

Example 54

The method according to example 52, comprising ruling out a presence of an arrhythmic cardiac condition when identifying less than a predetermined number of occurrences of cardiac fibrillation.

Example 55

The method according to example 51, wherein the one or more parameters of cardiac behavior are indicative of a non-arrhythmic cardiac condition.

Example 56

The method according to example 51, wherein the one or more parameters comprise a pulse wave shape.

According to an aspect of some embodiments of the present invention there is provided a method for analyzing a voice sample of a subject to determine an arrhythmic cardiac condition, including extracting at least one voice feature from the voice sample, detecting an effect of a cardiac condition on the at least one voice feature, determining an arrhythmic cardiac condition based on the effect.

According to some embodiments of the invention, the detecting an effect of a cardiac condition on the at least one voice feature includes detecting an effect of a cardiac condition as effected by at least one cause affecting voice selected from a group consisting of blood flow, ventricular beat, and atrial beat on the at least one voice feature.

According to some embodiments of the invention, the detecting an effect includes identifying an effect of at least one of a timing of the cause affecting voice, a periodicity of the cause affecting voice and a magnitude or change in magnitude of the cause affecting voice.

According to some embodiments of the invention, the determining an arrhythmic cardiac condition includes integrating a plurality of the identified effect.

According to some embodiments of the invention, further including classifying the voice sample to identify voiced segments.

According to some embodiments of the invention, further including concatenating the voiced segments, such that at least some segments are removed and remaining segment ends are smoothed.

According to some embodiments of the invention, further including extrapolating data pertaining to the cause affecting voice in segments which are removed from the voice sample.

According to some embodiments of the invention, the detected effect includes a timing of heart pulses.

According to some embodiments of the invention, the detecting an effect includes identifying three consecutive occurrences of heart pulses.

According to some embodiments of the invention, the determining an arrhythmic cardiac condition includes calculating time intervals between the consecutive occurrences of heart pulses and matching the time intervals with reference time intervals obtained from a reference heart condition.

According to some embodiments of the invention, the determining further includes determining a probability of the matching, and comparing the probability to a threshold for determining the arrhythmic cardiac condition.

According to some embodiments of the invention, the reference heart condition is healthy or arrhythmic.

According to some embodiments of the invention, the three occurrences of a heart pulse are not identified in the same voiced segment.

According to some embodiments of the invention, the detecting an effect includes identifying two consecutive occurrences of heart pulses.

According to some embodiments of the invention, the detected effect includes an effect of a magnitude, or a change in a magnitude of a heart pulse.

According to some embodiments of the invention, the detecting an effect includes calculating a distribution of a plurality of values of the at least one voice feature.

According to some embodiments of the invention, the determining an arrhythmic cardiac condition based on the effect includes comparing a characterizing parameter of the distribution to a threshold.

According to some embodiments of the invention, the characterizing parameter includes a shape of the distribution.

According to some embodiments of the invention, the value includes a width of the shape.

According to some embodiments of the invention, the detected effect includes an effect on a periodicity of heart pulses.

According to some embodiments of the invention, further including estimating a heart rate of the subject.

According to some embodiments of the invention, the determining an arrhythmic cardiac condition includes characterizing the periodicity at a predetermined range around a frequency of the heart rate, the characterizing includes calculating a band width of a peak at the predetermined range, and the determining the arrhythmic cardiac condition includes comparing the band width to a threshold.

According to some embodiments of the invention, further including validating the determining an arrhythmic cardiac condition.

According to some embodiments of the invention, the validating includes obtaining a second voice sample including a predetermined vocalization.

According to some embodiments of the invention, the validating includes at least one of an electrocardiogram test and a photoplethysmography test to the subject.

According to some embodiments of the invention, the arrhythmic cardiac condition includes atrial fibrillation.

According to some embodiments of the invention, the voice sample is spontaneous speech.

According to some embodiments of the invention, the voice feature includes a pitch.

According to some embodiments of the invention, extracting the voice feature includes performing cross coherence between a first segment of the voice sample and a second segment of the voice sample.

According to some embodiments of the invention, extracting the voice feature includes performing analysis of the speech signal selected from a group consisting of wavelet analysis, Mel Frequency Cepstral Coefficient (MFCC) analysis, glottal pulse analysis, and Linear Predictive Coding (LPC) analysis.

According to an aspect of some embodiments of the present invention there is provided a system for determining an arrhythmic cardiac condition in a voice sample provided by a subject, including a voice input for obtaining a digital voice sample of the voice sample, a voice feature extractor that extracts at least one voice feature from the digital voice sample, a voice feature processor that identifies an effect of cardiac activity on the at least one voice feature, a cardiac condition classifier that determines arrhythmic cardiac condition based on the effect.

According to some embodiments of the invention, the voice input forms a part of at least one of a mobile phone, digital assistant and a car multimedia system.

According to some embodiments of the invention, at least one of the voice feature extractor, voice feature processor and cardiac condition classifier is located at a server.

According to some embodiments of the invention, the server is collocated with a telephone switch and gets the data from the switch.

According to some embodiments of the invention, the voice input is configured to obtain the digital voice sample according to a predetermined schedule.

According to some embodiments of the invention, further including a permanent memory wherein the memory stores reference voice features derived from a plurality of voice samples associated with an arrhythmic cardiac condition or a healthy cardiac condition.

According to some embodiments of the invention, the cardiac condition classifier determines the arrhythmic cardiac condition based on a training stage characterizing the reference voice features.

According to some embodiments of the invention, the permanent memory stores at least one previously collected voice sample from the subject.

According to some embodiments of the invention, the cardiac condition classifier determines the arrhythmic cardiac condition based on a change between the previously collected voice samples and the digital voice sample.

According to an aspect of some embodiments of the present invention there is provided a system for determining a cardiac condition in a voice sample provided by a subject, including a voice input for obtaining a digital voice sample of the voice sample, a voice feature extractor that extracts at least one voice feature from the digital voice sample, a voice feature processor that identifies an effect of a cardiac condition on the at least one voice feature, a cardiac condition classifier that determines the cardiac condition based on the effect.

According to an aspect of some embodiments of the present invention there is provided a method for analyzing a voice sample of a subject to determine a cardiac condition, including extracting at least one voice feature from the voice sample, detecting an effect of a blood flow on the at least one voice feature, the effect being at least one of a timing of the blood flow, a periodicity of the blood flow and a magnitude or change in magnitude of the blood flow, determining a cardiac condition based on the effect.

According to some embodiments of the invention, the determined cardiac condition includes an abnormal heart rate.

According to some embodiments of the invention, the abnormal heart rate includes ventricle tachycardia.

According to some embodiments of the invention, the determined cardiac condition includes at least one of ectopic beats and premature ventricular contraction.

According to an aspect of some embodiments of the present invention there is provided a method for analyzing a voice sample of a subject to reconstruct a cardiac behavior, including extracting at least one voice feature from the voice sample, detecting an effect of a blood flow on the at least one voice feature, and reconstructing one or more parameters of the cardiac behavior from the detected effect.

According to some embodiments of the invention, the cardiac behavior includes an occurrence of cardiac fibrillation.

According to some embodiments of the invention, including determining a presence of an arrhythmic cardiac condition when identifying more than a predetermined number of occurrences of cardiac fibrillation.

According to some embodiments of the invention, including ruling out a presence of an arrhythmic cardiac condition when identifying less than a predetermined number of occurrences of cardiac fibrillation.

According to some embodiments of the invention, the one or more parameters of cardiac behavior are indicative of a non-arrhythmic cardiac condition.

According to some embodiments of the invention, the one or more parameters include a pulse wave shape.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions, even a cellular phone. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as identifying and matching acoustic patterns, might be expected to use completely different methods, e.g., making use of expert knowledge and/or the pattern recognition capabilities of the human brain, which would be vastly more efficient than manually going through the steps of the methods described herein.

As used herein, the term circuit or circuitry refers to hardware and\or software having instructions to perform selected tasks, for example, a controller having a memory that performs certain calculations (software or algorithm), or a chip that performs some signal processing tasks—for example, in purpose to conduct voice analysis.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a data flow map illustrating the flow of data between optional voice analyzing stations, in accordance with some embodiments of the invention;

Figure 4A:
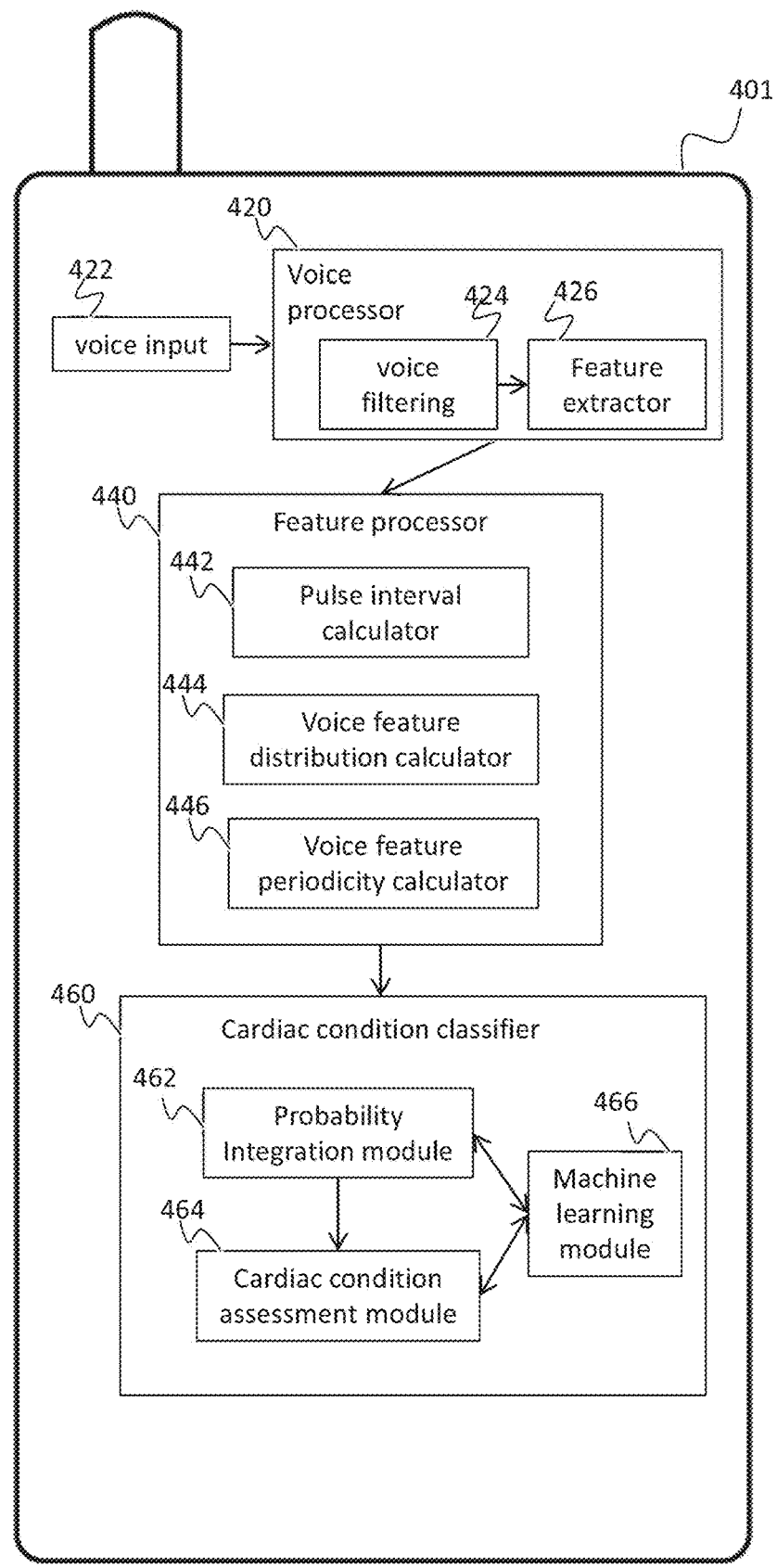
Figure 4B:
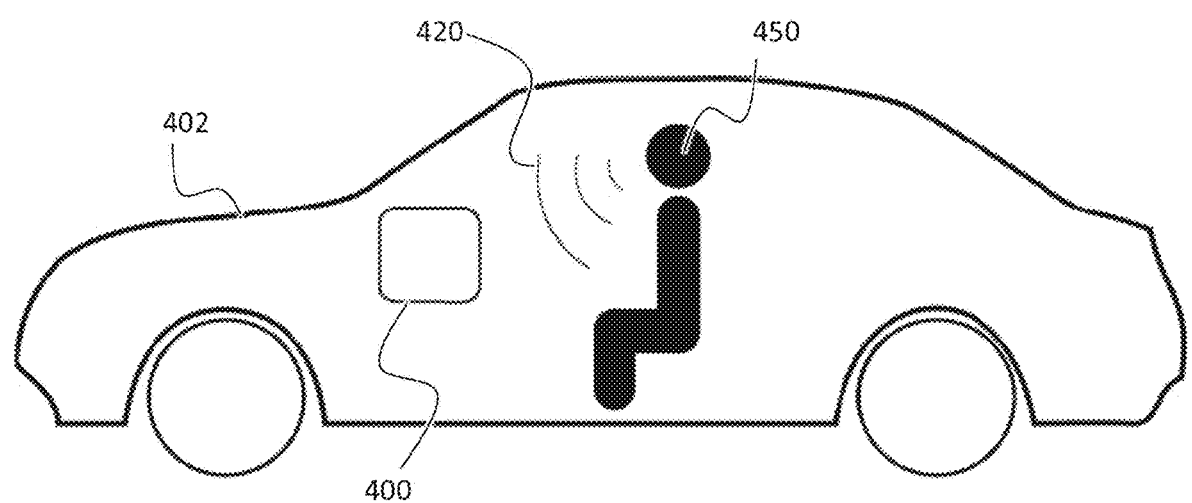
Figure 5A:
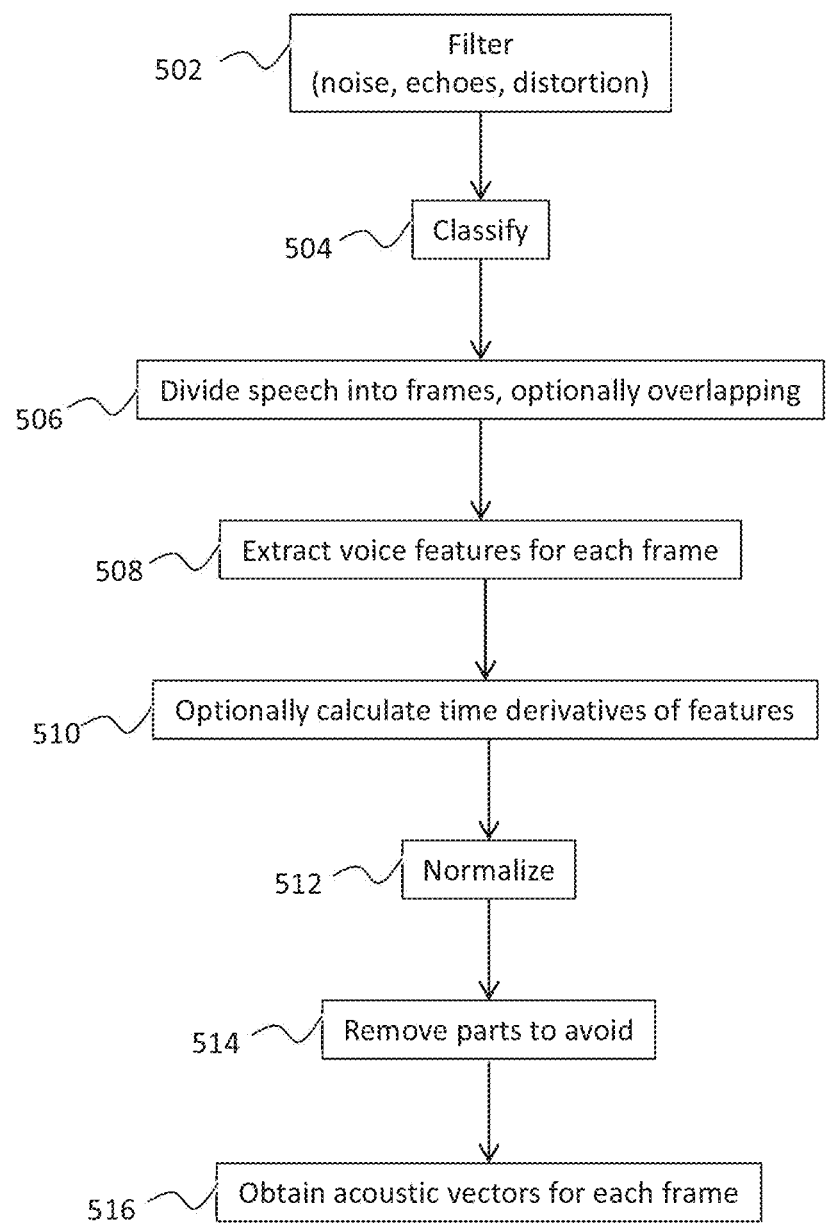
Figure 5B:
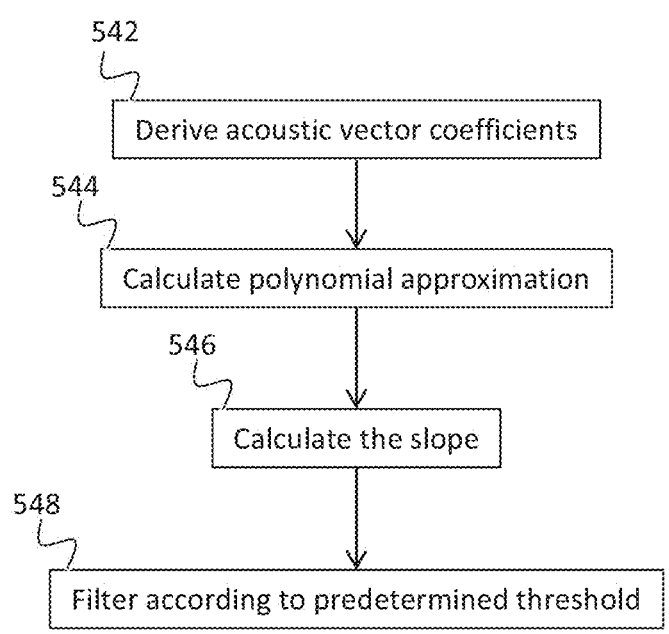
Figure 5C:
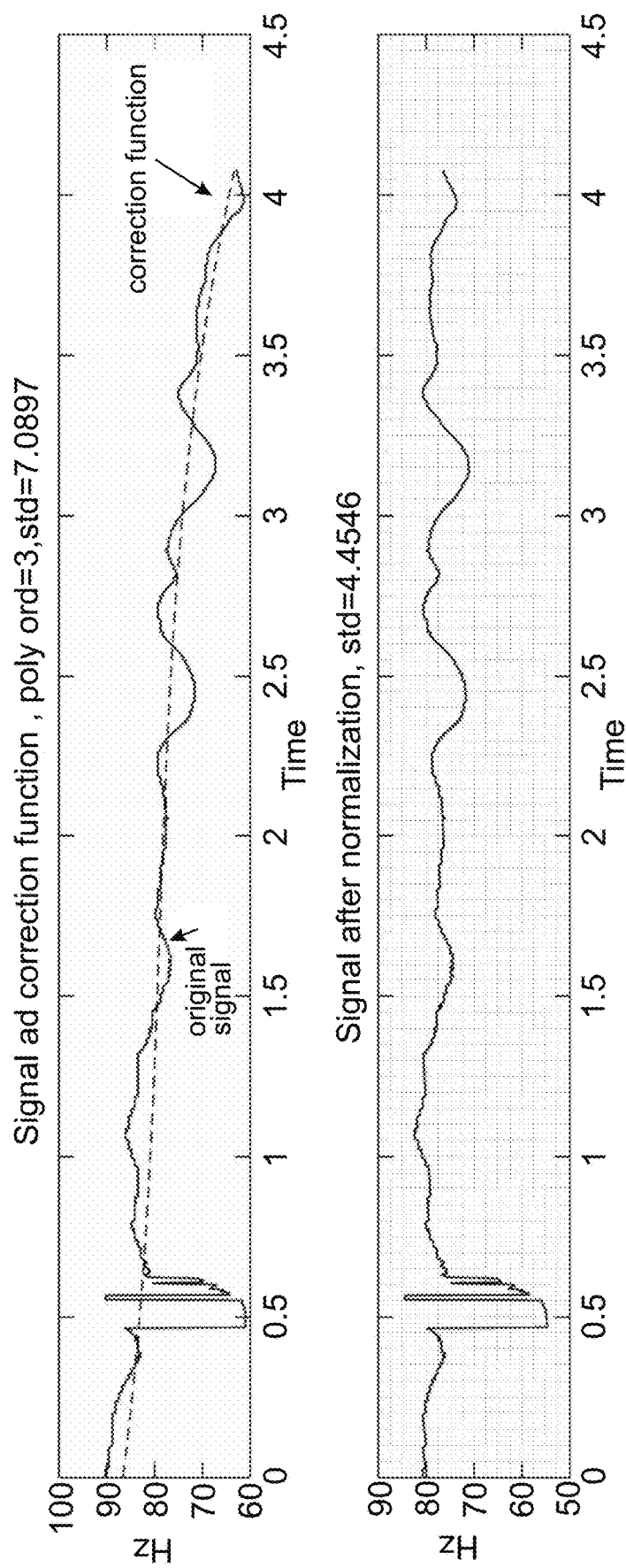
Figure 6A:
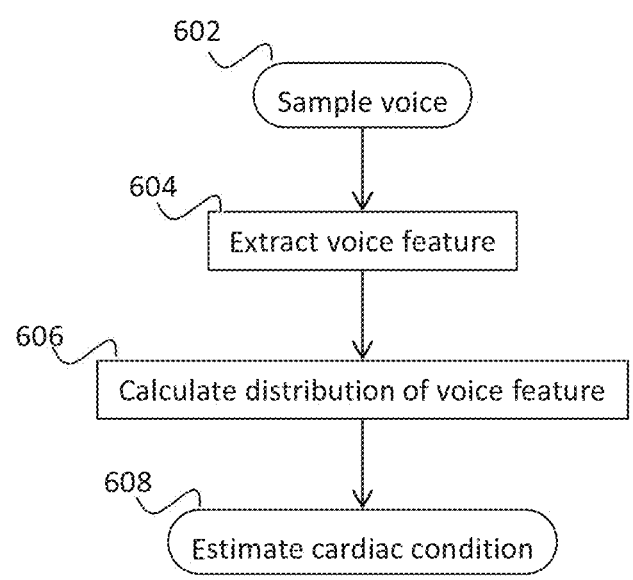
Figure 6B:
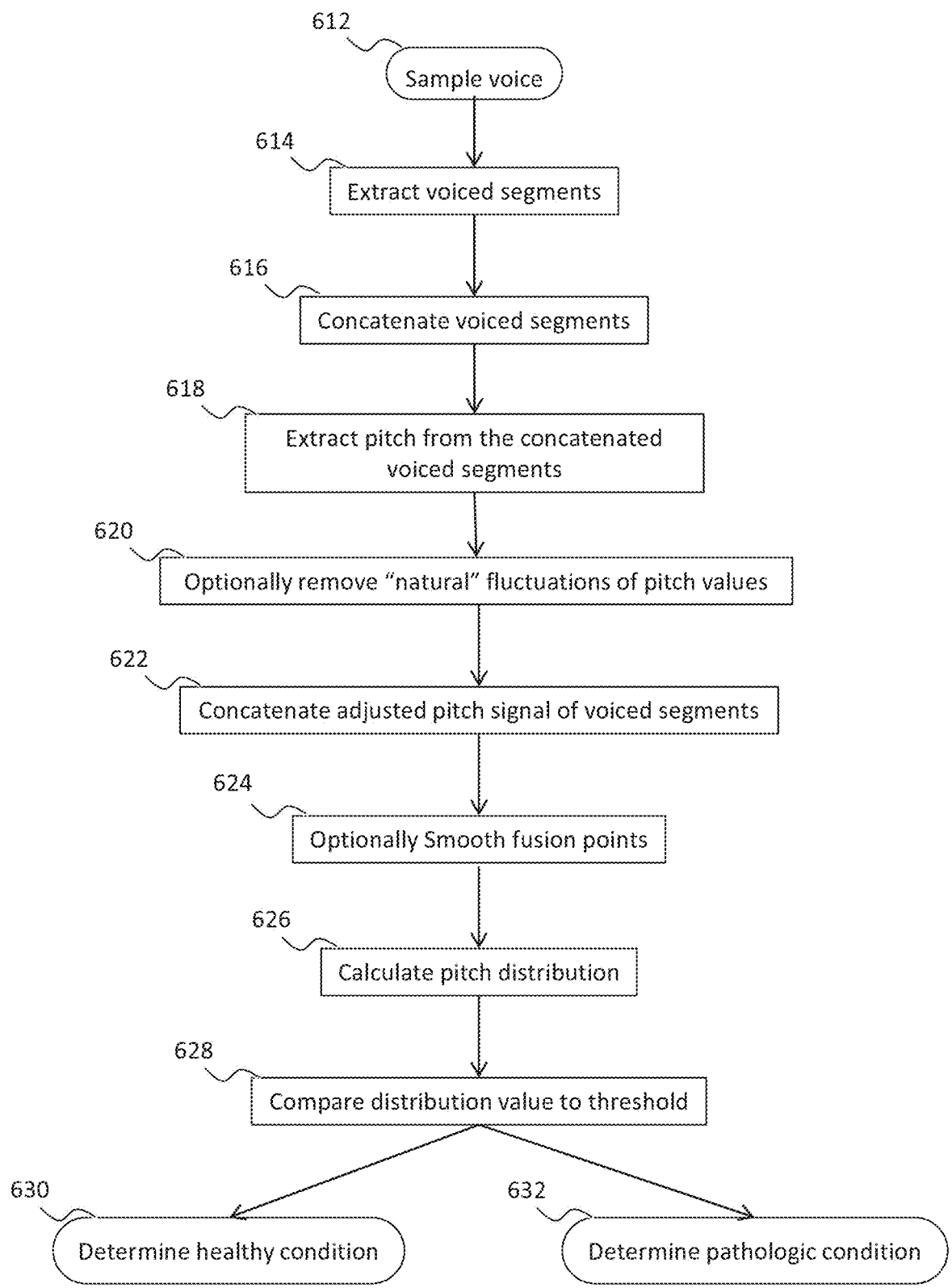
Figure 6C:
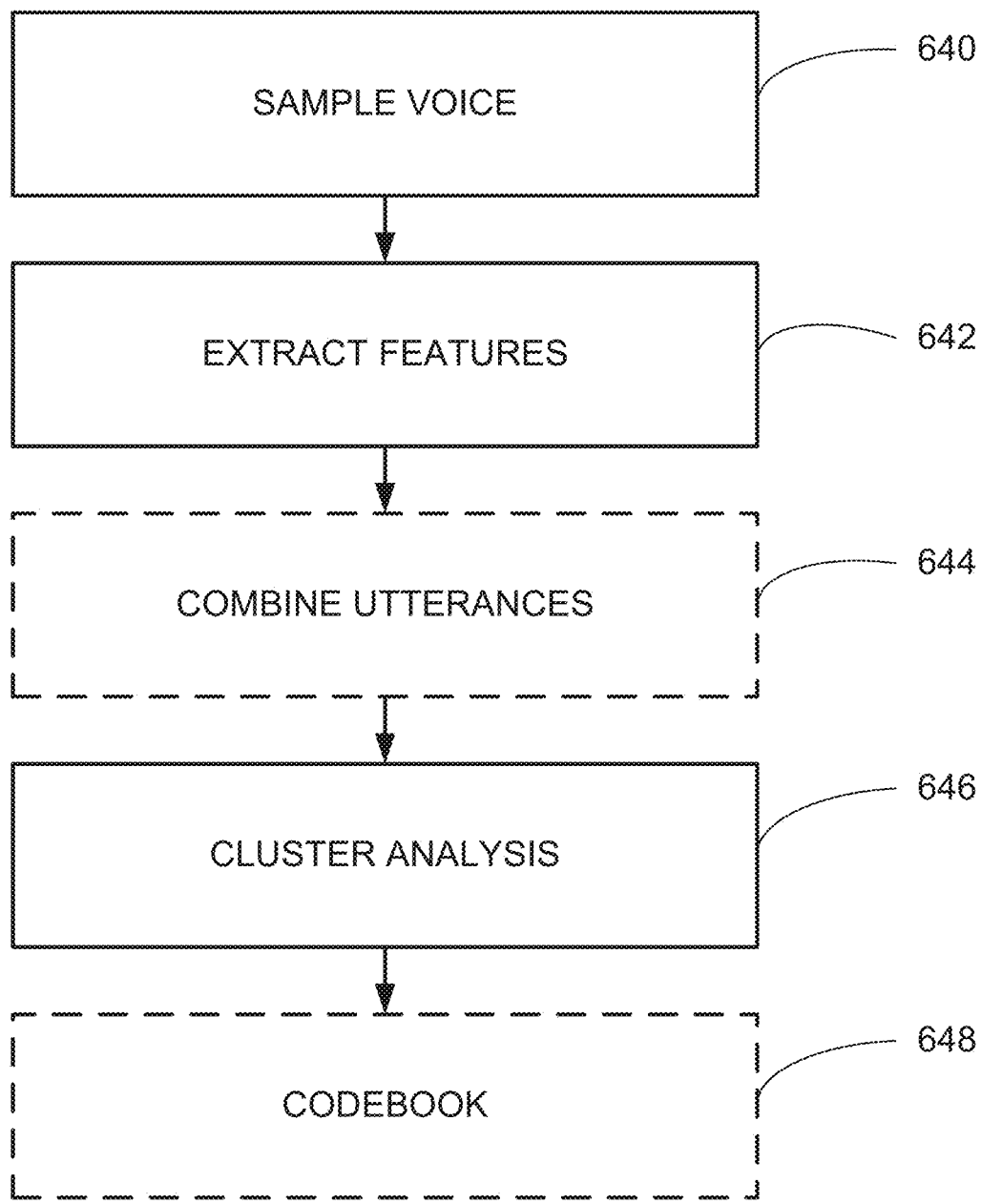
Figure 6D:
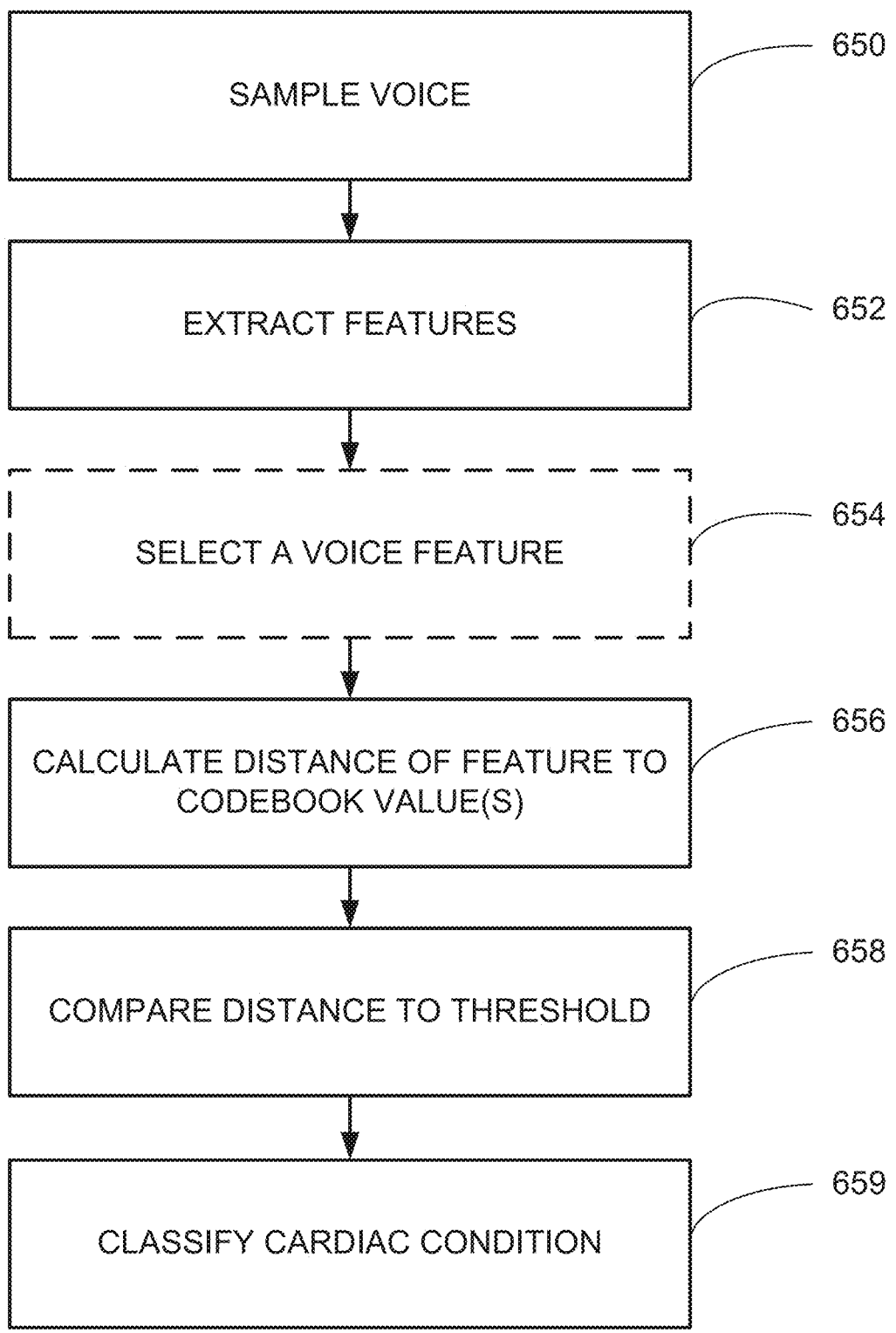
Figure 7A:
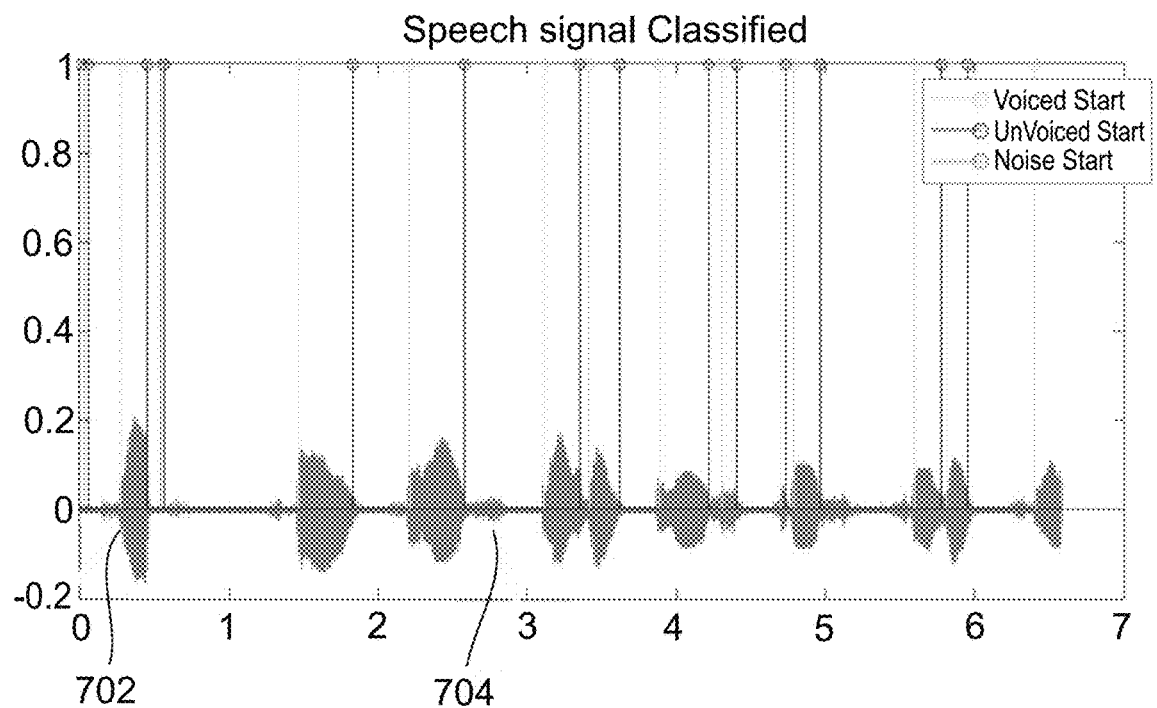
Figure 7B:
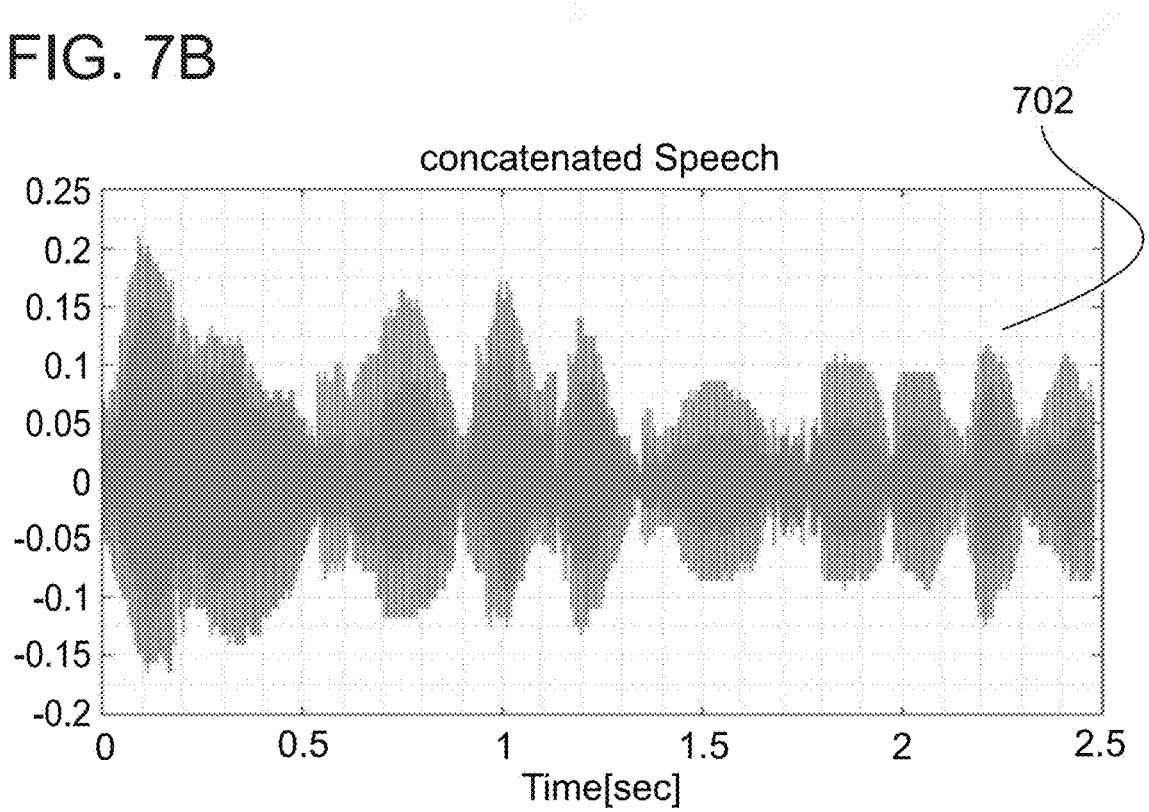
Figure 8A:
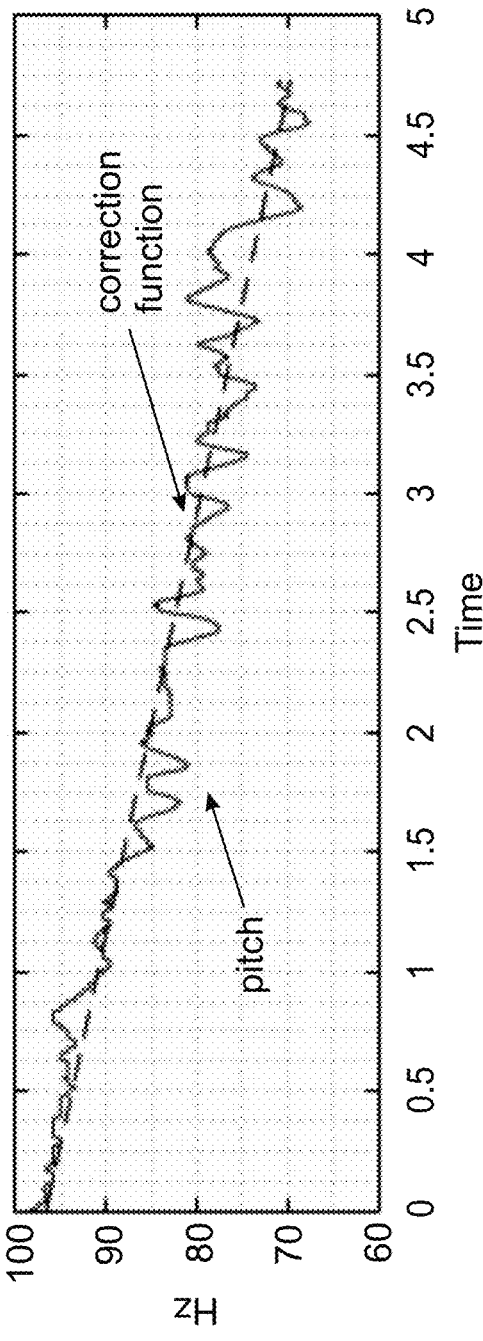
Figure 8B:
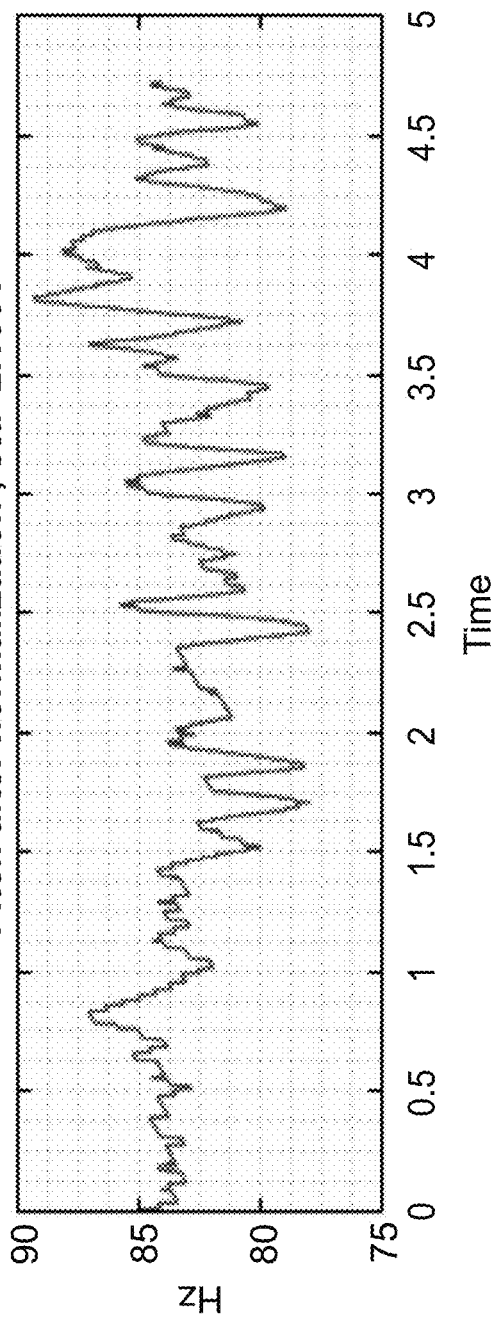
Figure 9A:
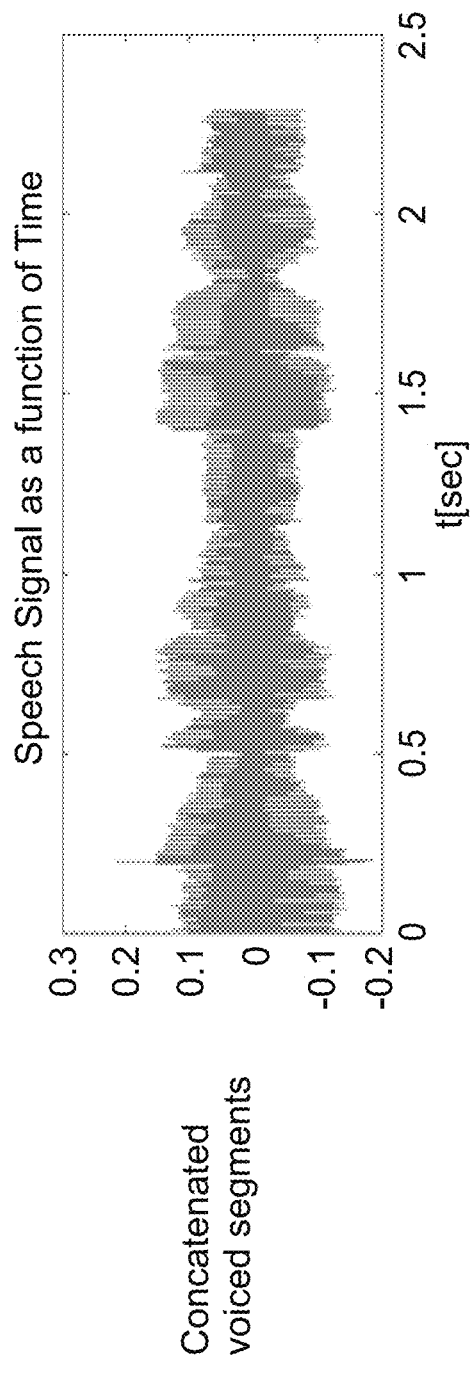
Figure 9B:
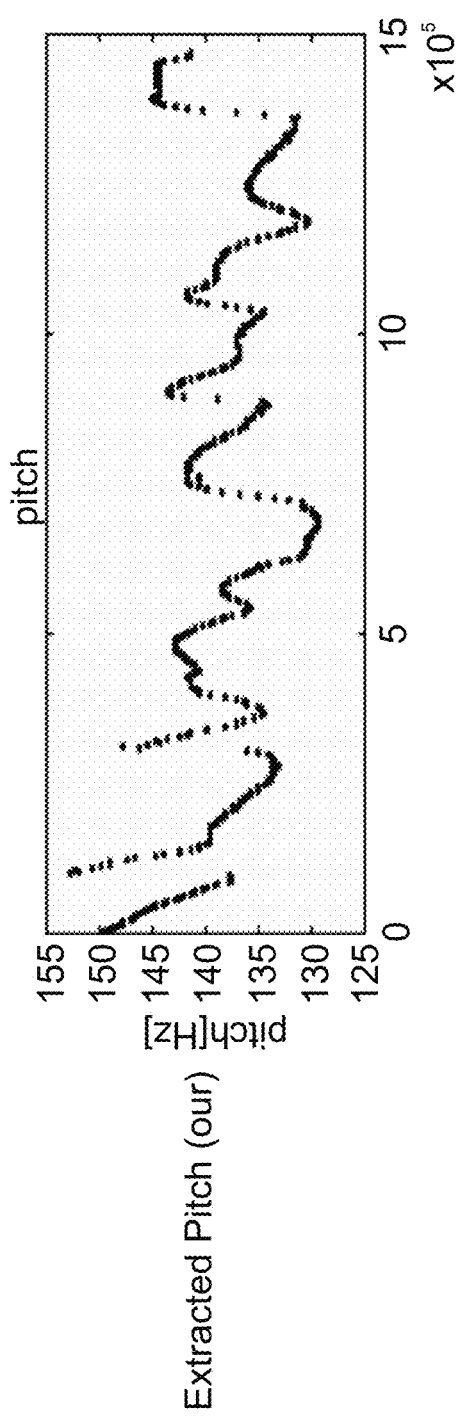
Figure 11A:
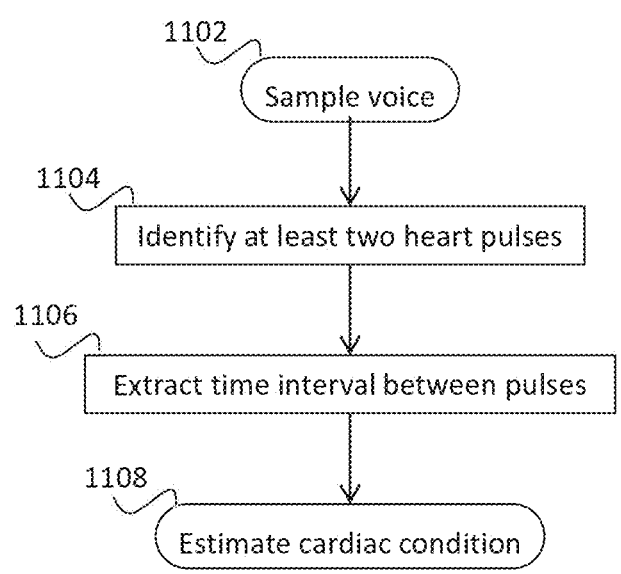
Figure 11B:
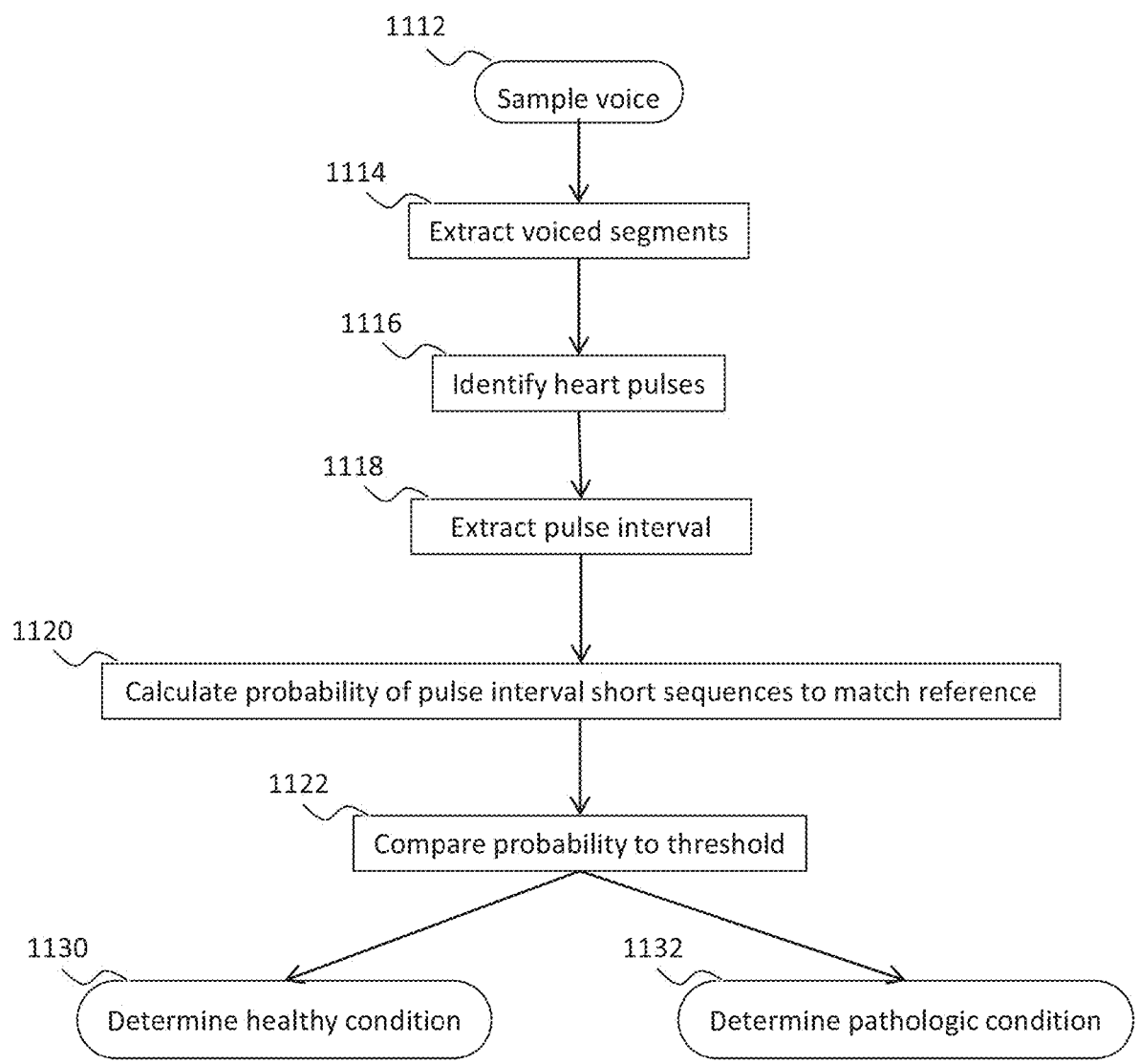
Figure 11C:
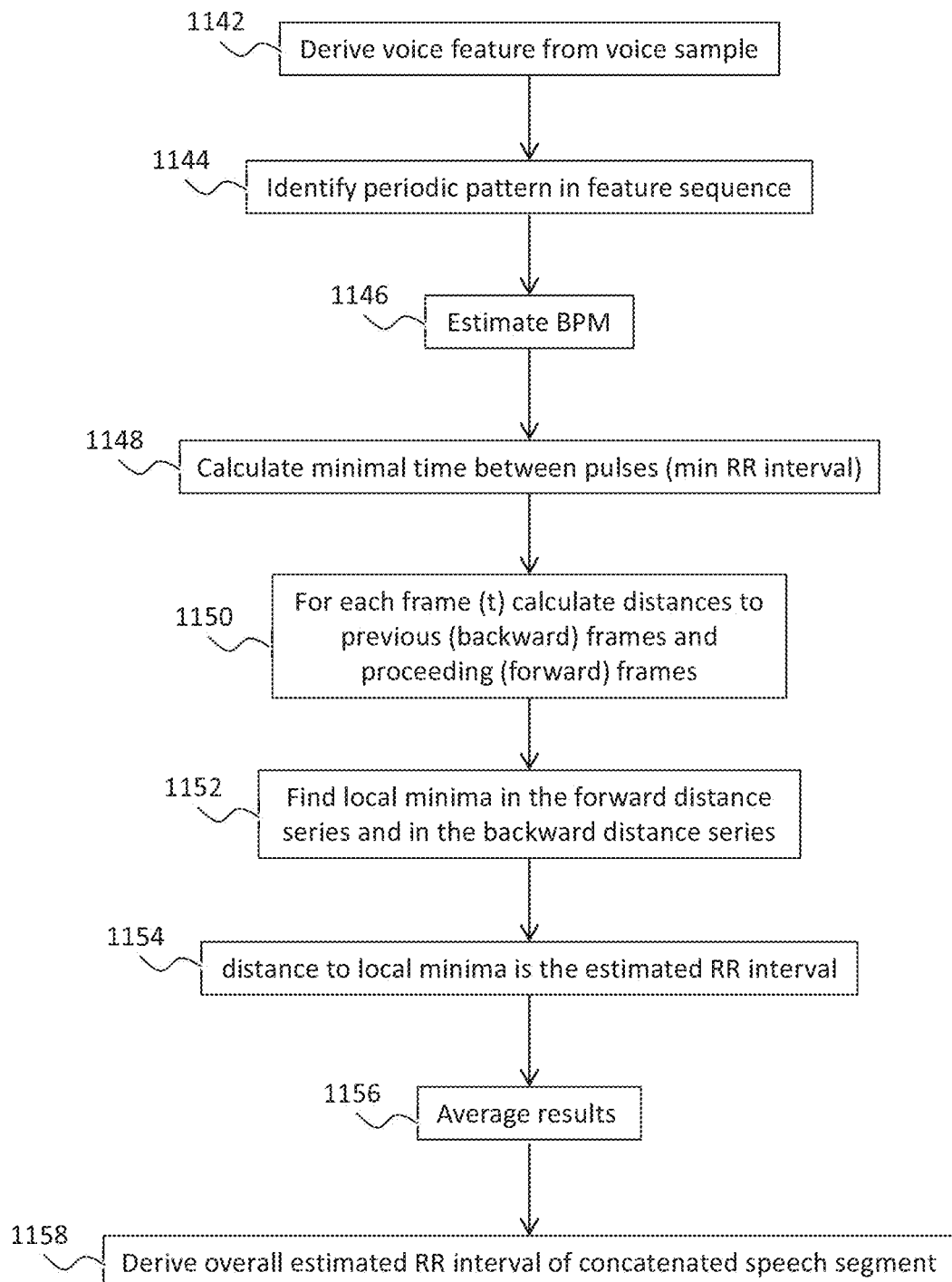
Figure 11D:
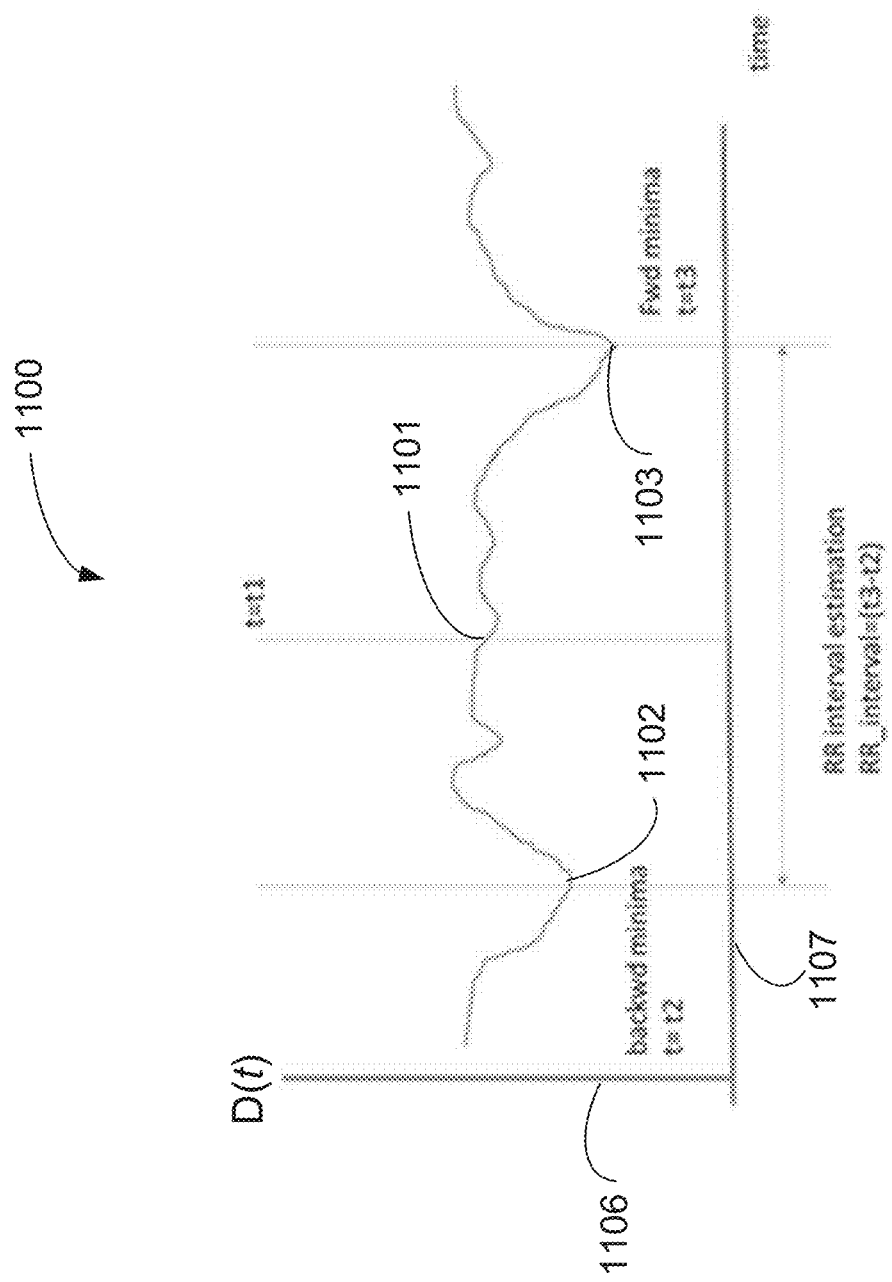
Figure 12A:
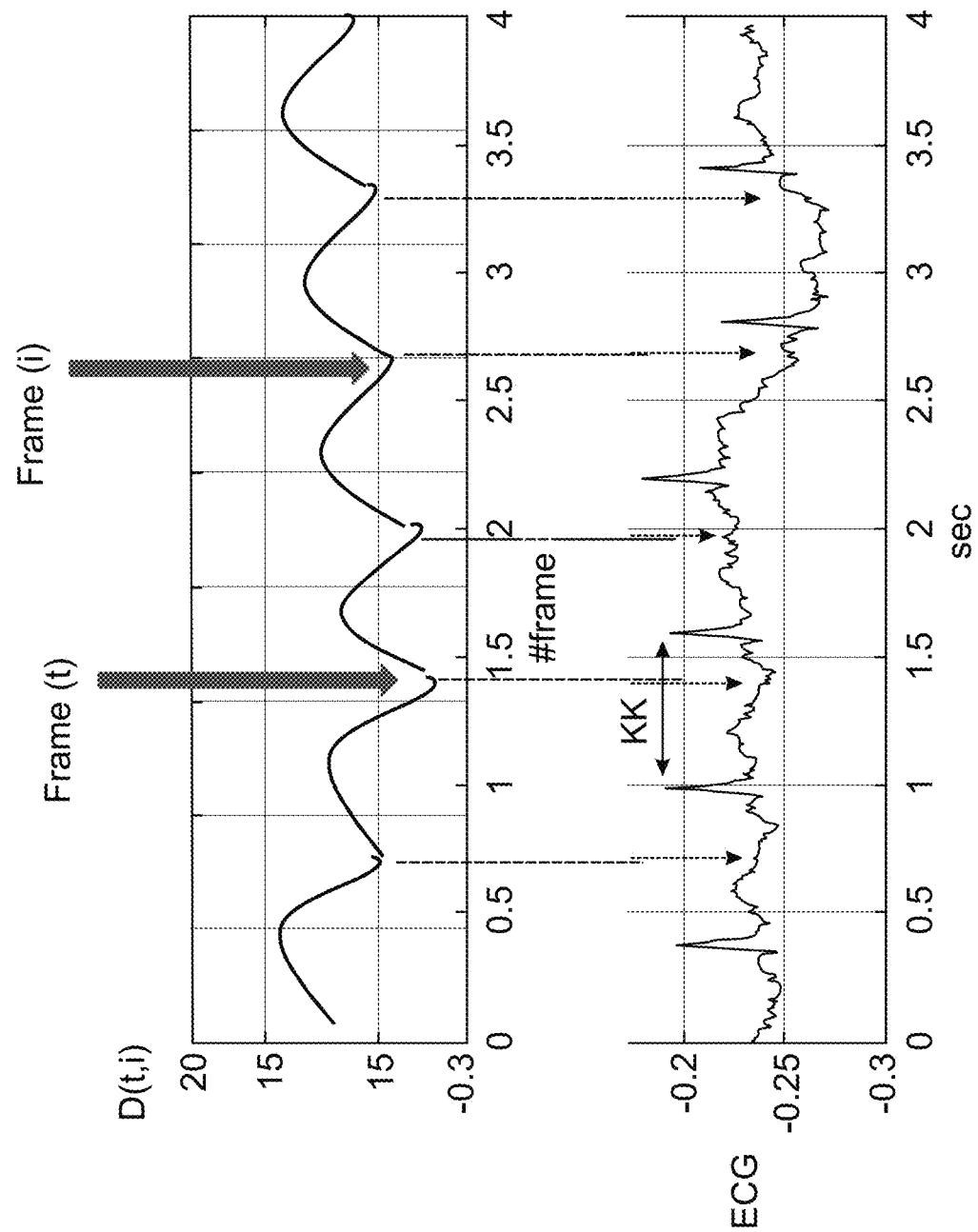
Figure 12B:
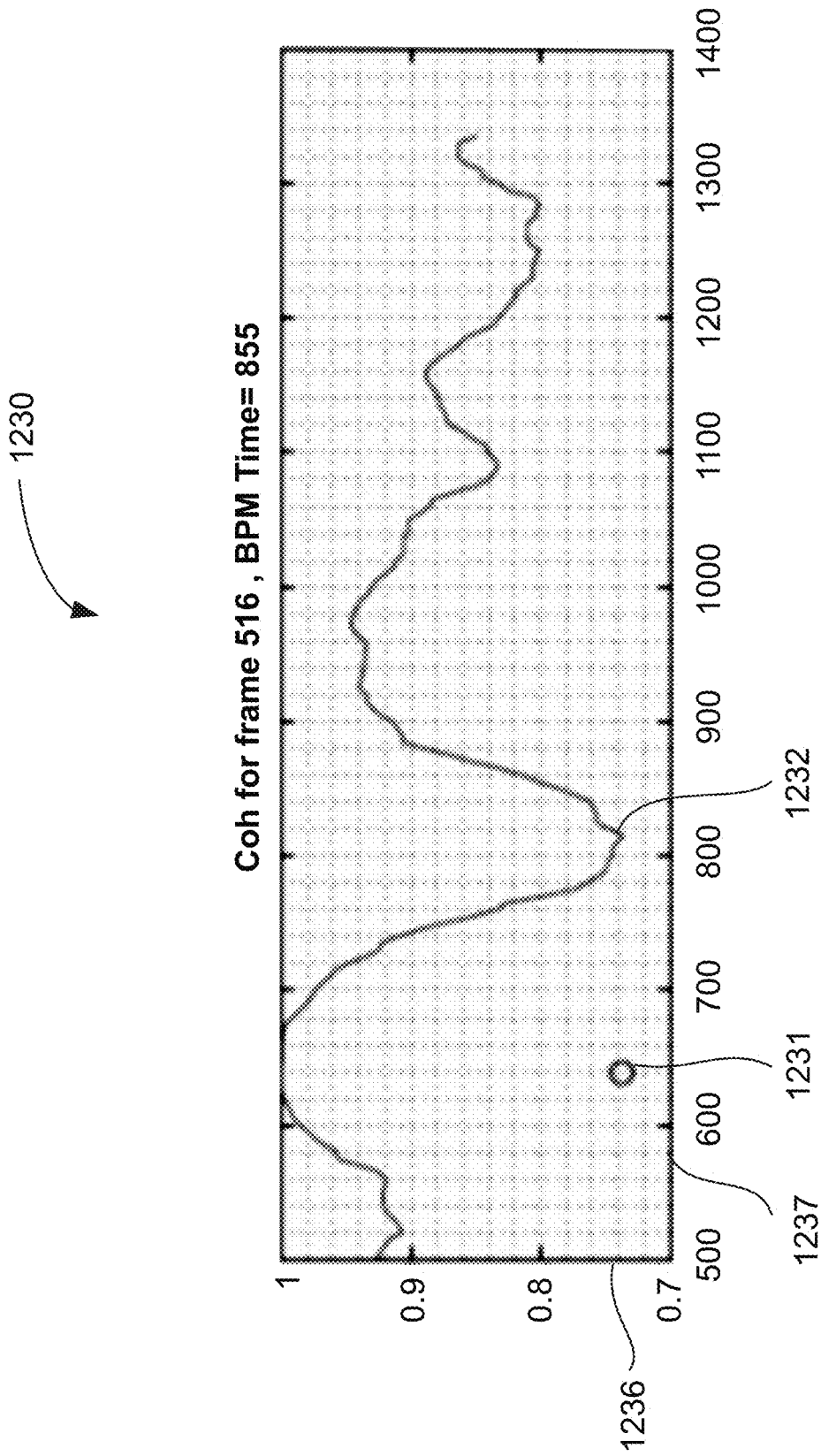
Figure 13:
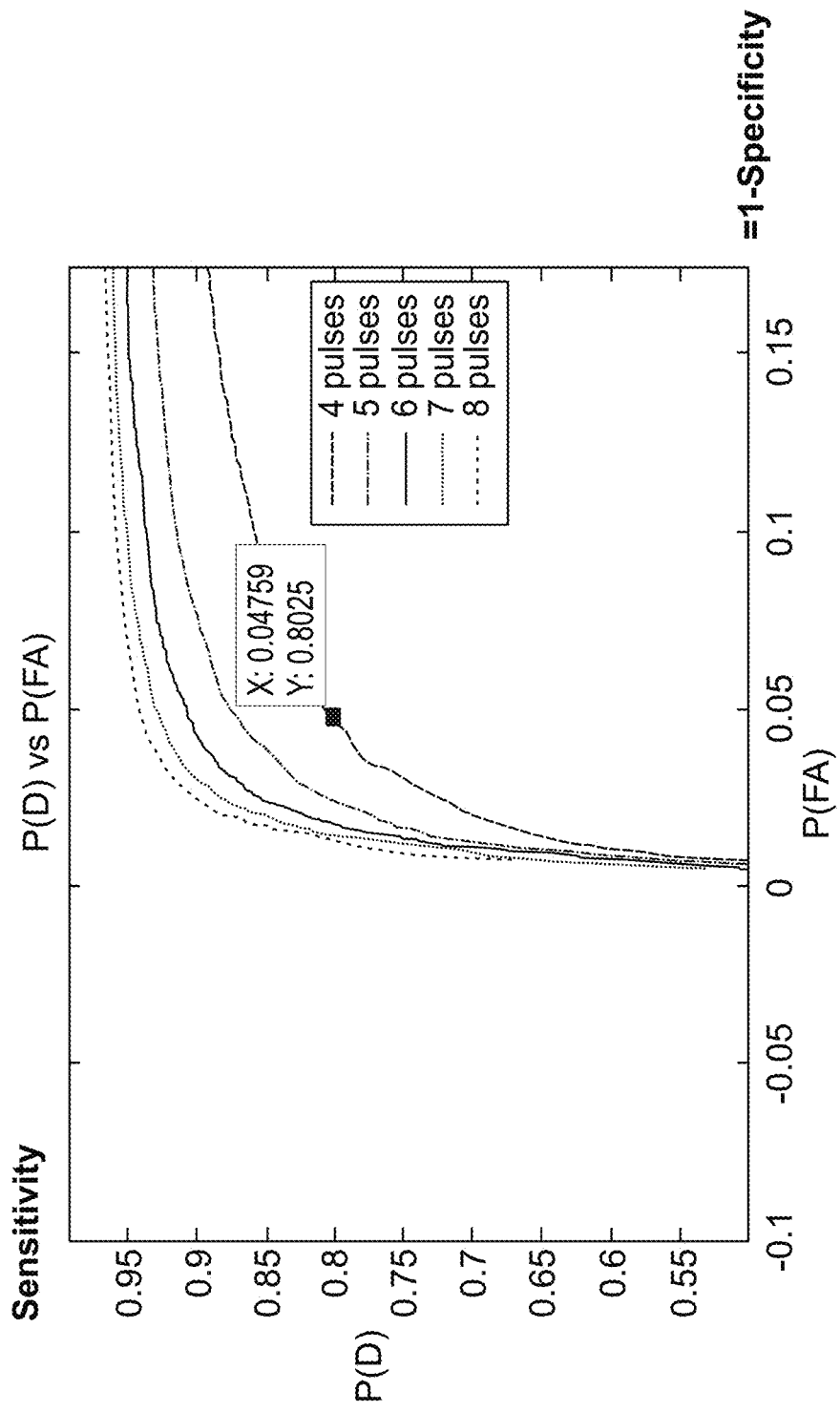
Figure 14A:
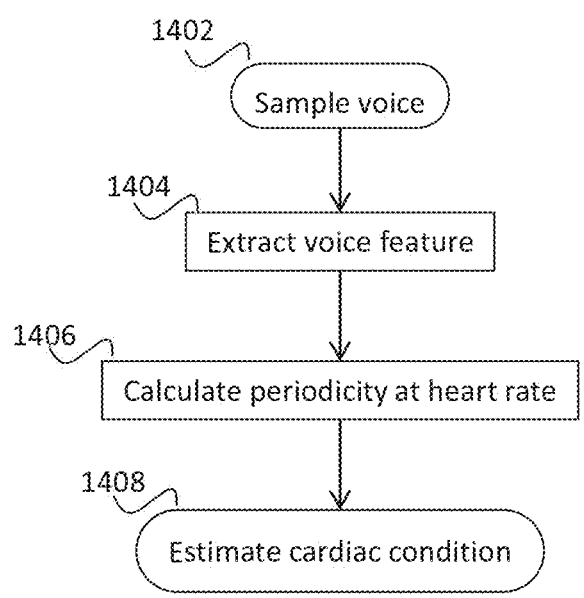
Figure 14B:
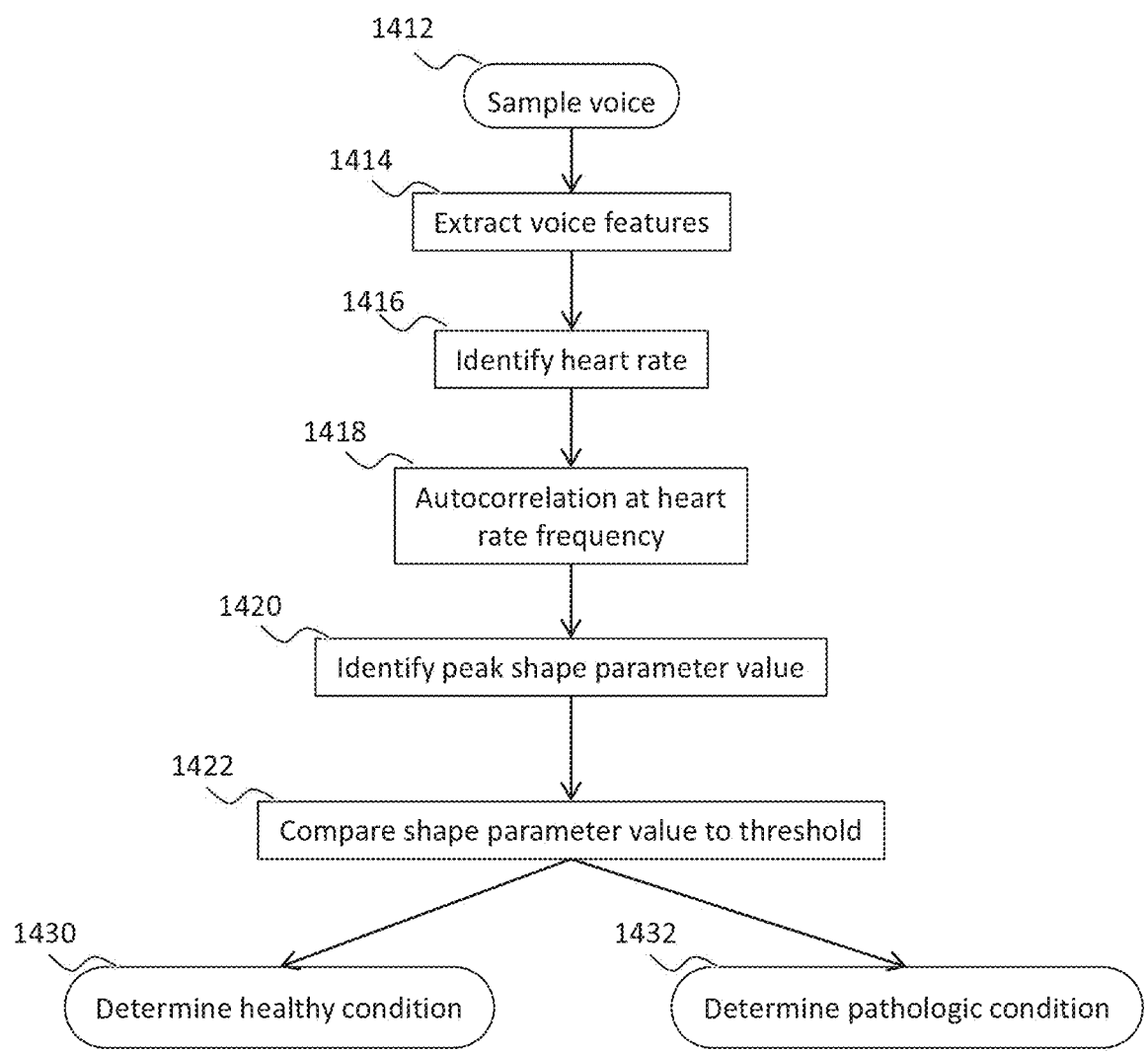
Figure 14C:
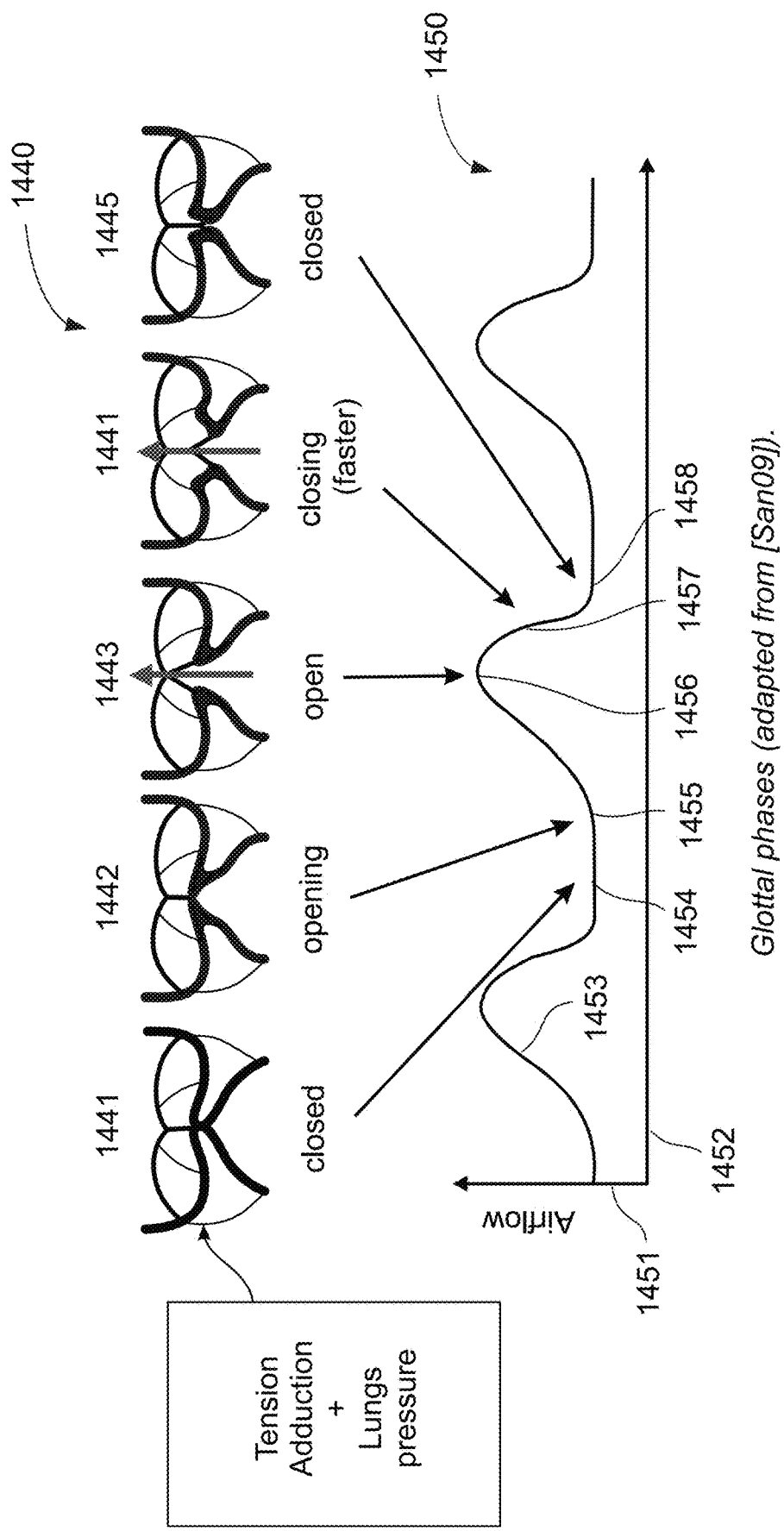
Figure 15A:
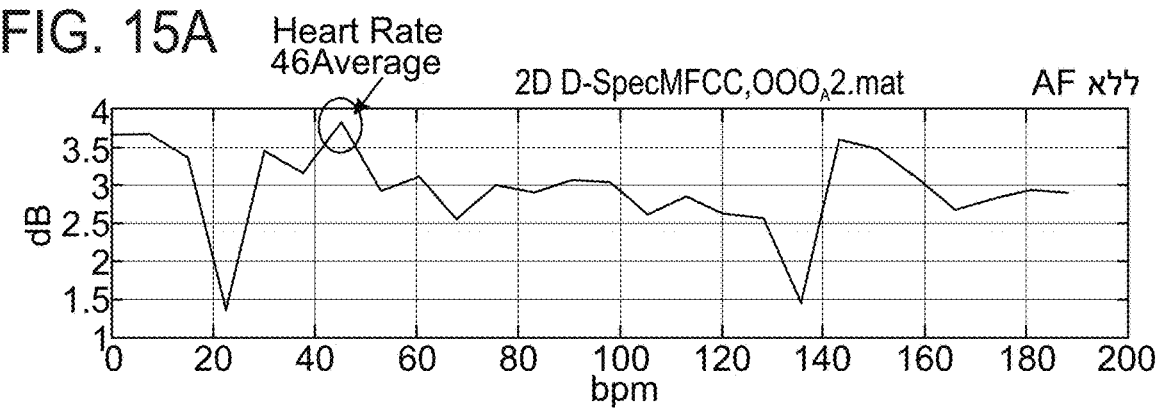
Figure 15B:
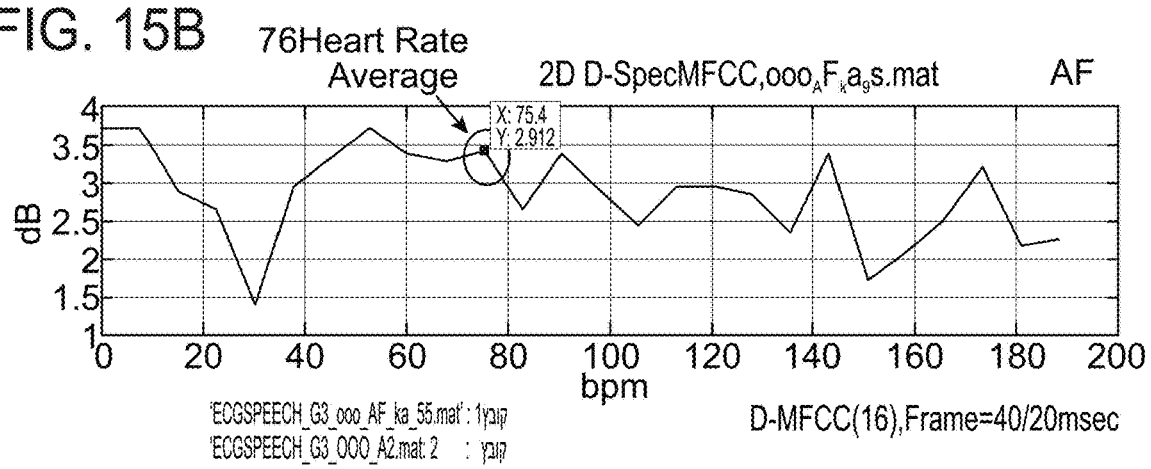
Figure 15C:
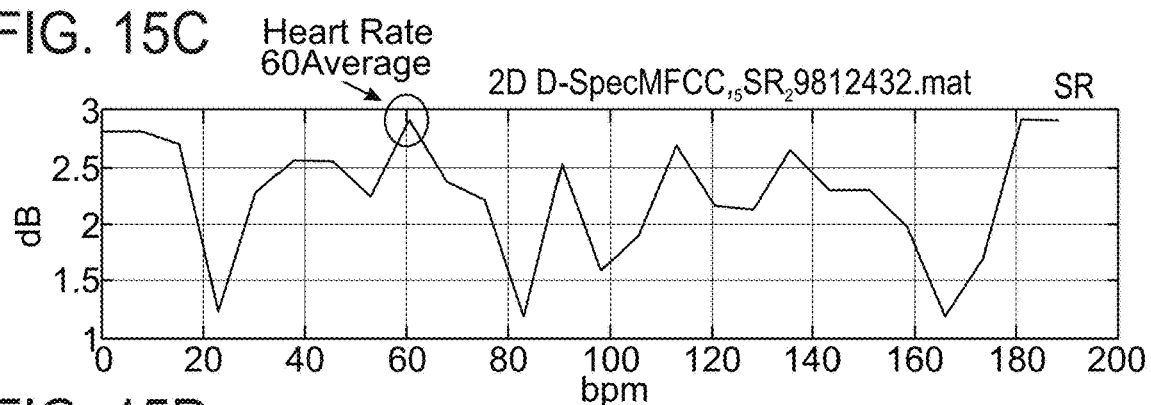
Figure 15D:
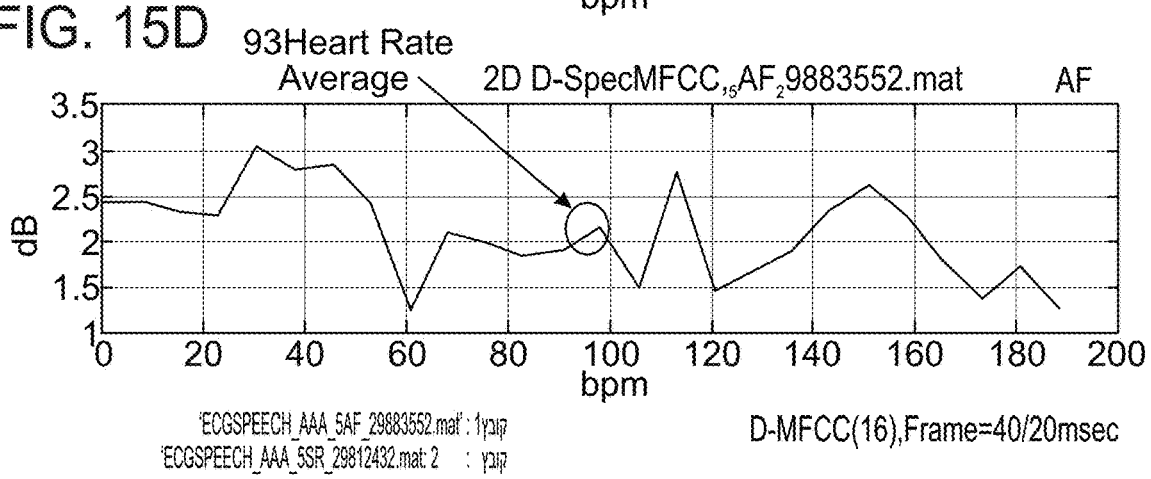
Figure 16:
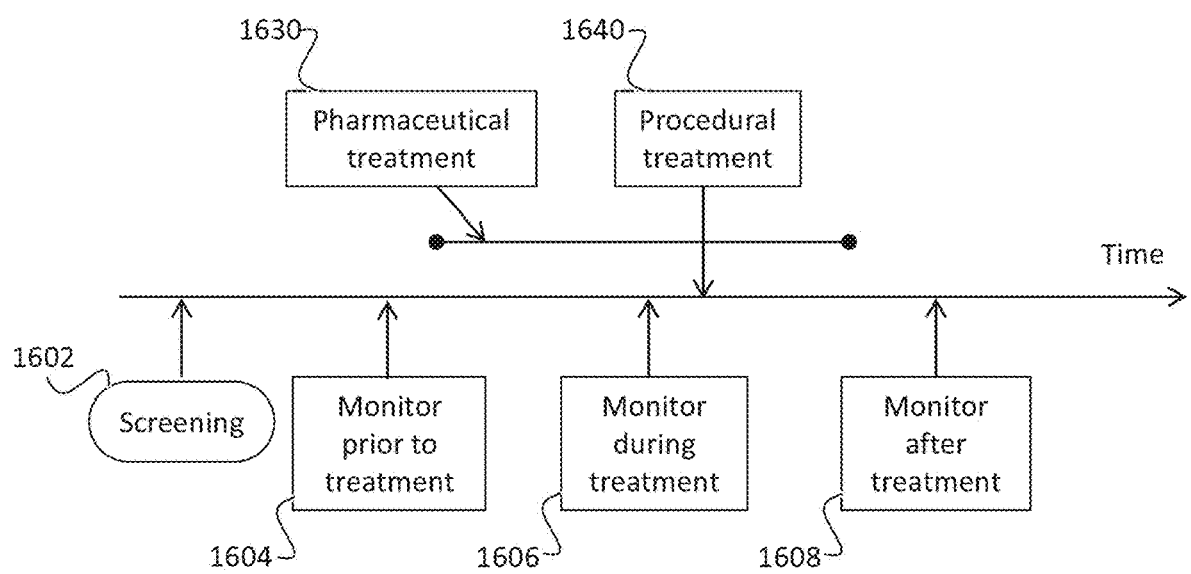
Figure 17:
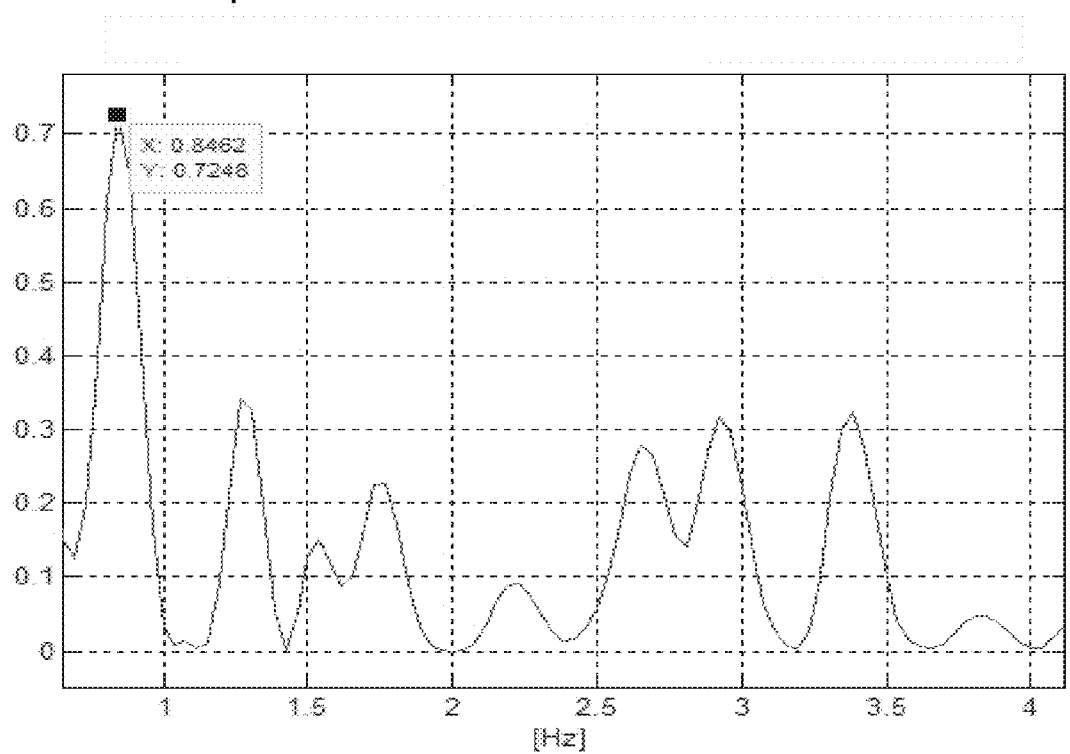
Figure 18B:
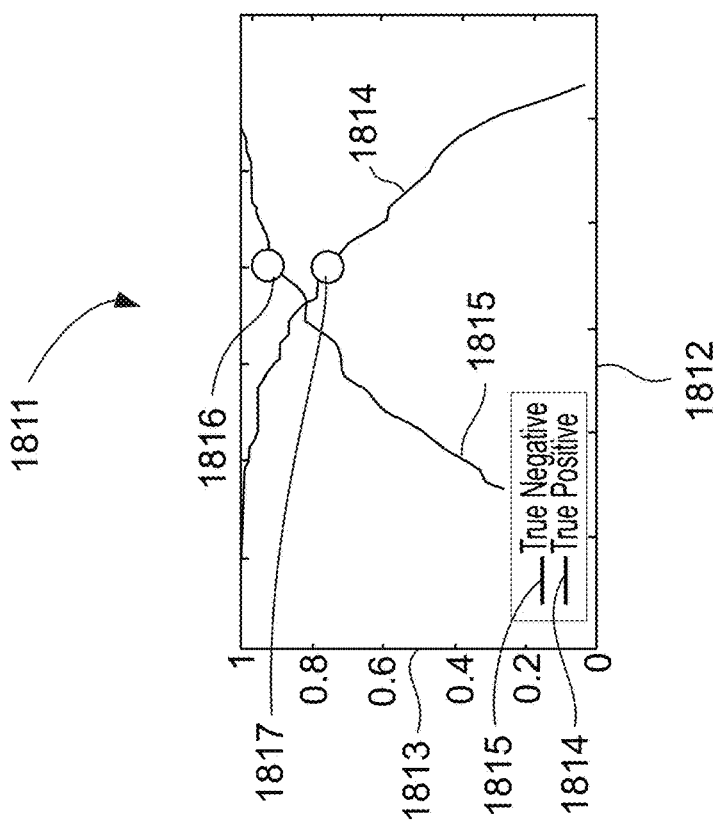
Figure 18A:
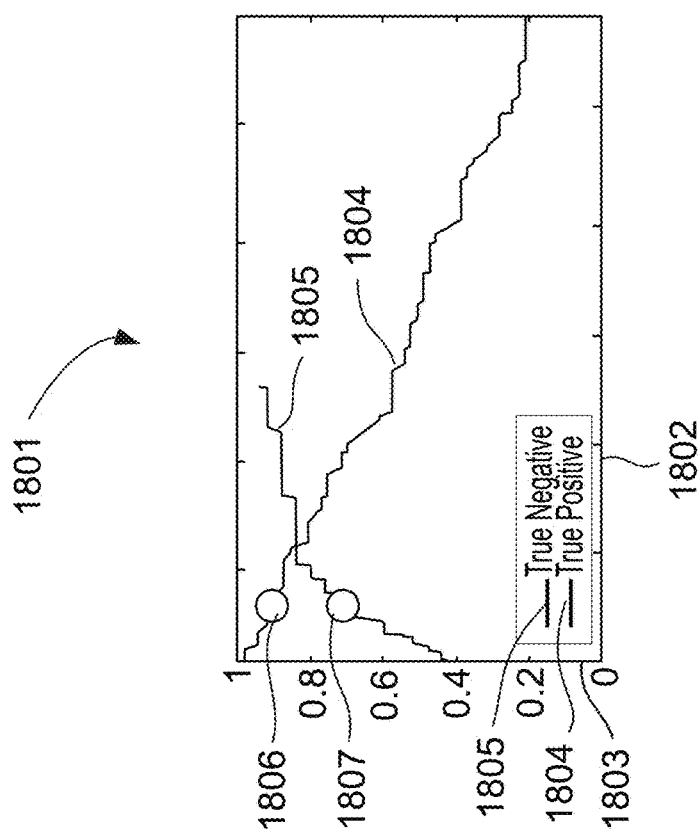

FIGS. 4A-4B schematically illustrate voice sampling and/or analysis in exemplary platforms, wherein FIG. 4A illustrates a mobile phone platform and FIG. 4B illustrates a vehicle platform, in accordance with some embodiments of the invention;

FIGS. 5A-C illustrate exemplary voice processing, in accordance with some embodiments of the invention, wherein FIG. 5A illustrates voice sample processing to obtain acoustic vectors, FIG. 5B illustrates voice feature normalization process and FIG. 5C presents a normalization example;

FIG. 6A is a general high level overview illustrating estimation of a cardiac condition from a voice sample by distribution analysis, in accordance with some embodiments of the invention;

FIG. 6B is a flowchart illustrating a detailed process for feature distribution analysis showing the pitch as an example for voice feature, in accordance with some embodiments of the invention;

FIG. 6C is a simplified flow chart illustration of a method for learning to diagnose cardiac conditions in accordance with some embodiments of the invention;

FIG. 6D is a simplified flow chart illustration of a method for classifying cardiac condition in accordance with some embodiments of the invention;

FIGS. 7A-7B present a voice sample shown in FIG. 7A, which has been classified to remove segments and the remaining segments have been concatenated in FIG. 7B, in accordance with some embodiments of the invention;

FIGS. 8A-8B show an example for pitch data extracted from a voice sample which has been smoothed, wherein FIG. 8A illustrates smoothing of "natural" fluctuations of the voice, and FIG. 8B illustrates smoothed data, in accordance with some embodiments of the invention;

FIGS. 9A-9B show an example for pitch data extracted from a voice sample, after being filtered and smoothed, in accordance with some embodiments of the invention, wherein FIG. 9A shows an example for concatenated voiced segments, and FIG. 9B shows an example for pitch extraction;

FIGS. 10A-10D show an example of histograms of the distribution of the normalized standard deviation values of a pitch of speech recorded during AF (FIGS. 10B and 10D) and during speech of healthy people (FIGS. 10A and 10C), in accordance with some embodiments of the invention;

FIGS. 11A-11C illustrate cardiac timing analysis in the form of pulse interval analysis, in accordance with some embodiments of the invention, wherein FIG. 11A shows a general flow chart, FIG. 11B shows a detailed flow chart and FIG. 11C shows exemplary pulse determination over time in accordance with some embodiments of the invention;

FIG. 11D shows an exemplary graph of RR interval estimation in accordance with some embodiments of the invention;

FIG. 12A shows an example of the frame to frame distance for MFCC type voice features, wherein the top graph shows frame to frame distance pattern and the bottom graph shows an ECG graph as a reference, in accordance with some embodiments of the invention;

FIG. 12B shows an exemplary graph of coherence calculation in accordance with some embodiments of the invention;

FIG. 13 shows an example for the change in sensitivity versus the specificity of heart condition determination with increasing occurrences of consecutive pulses, in accordance with some embodiments of the invention;

FIGS. 14A-14B show a process for determining periodicity at the heart rate used for determining a cardiac condition, in accordance with some embodiments of the invention, wherein FIG. 14A is a high level overview and FIG. 14B is a detailed flow chart;

FIG. 14C is a simplified illustration of a glottal wave, in accordance with some embodiments of the invention;

FIGS. 15A-15D show determination of probability for heart rate pathology using spectral properties of voice features, in accordance with some embodiments of the invention, wherein FIGS. 15A and 15C show a healthy pattern, and FIGS. 15B and 15D illustrate AF pattern, in accordance with some embodiments of the invention;

FIG. 16 shows a timeline of possible treatments and monitoring, in accordance with some embodiments of the invention;

FIG. 17 is an example for heart rate extraction from a voice sample, in accordance with some embodiments of the invention;

FIG. 18A is a graph showing speaker-independent detection results in accordance with some embodiments of the invention; and FIG. 18B is a graph showing speaker-dependent detection results in accordance with some embodiments of the invention.

DESCRIPTION OF SPECIFIC EMBODIMENTS OF THE INVENTION

The present invention, in some embodiments thereof, relates to medical diagnosis using voice and, more particularly, but not exclusively, to estimating cardiac conditions based on human voice.

Overview

An aspect of some embodiments of the invention relates to determining effect of timing and/or magnitude of an effect of a cardiac activity, such as blood flow, on a voice sample.

The cardiac activity may affect the voice sample in any one or more of:
  affecting blood flow, which affects the voice sample;
  transferring an effect of a heartbeat to the lungs, which affect the voice sample. It is noted that the left lung shares space in a chest with the heart;
  transferring an effect of a heartbeat to the bronchi, which affect the voice sample;
  transferring an effect of a heartbeat to pleural fluid, which affects the voice sample; and
  heartbeat-related mechanical changes in arteries and muscles along the larynx (the "voice box") and the vocal tract which potentially cause detectable modulations in the vocal sounds.

In some embodiments a voice sample of a subject is analyzed determine an arrhythmic cardiac condition, by detecting an effect of a cardiac condition on the voice sample, In some embodiments the analyzing includes detecting an effect of a cause which affects the voice sample.

Some none-limiting examples of such causes include:
  blood flow;
  ventricular beat; and
  atrial beat In the present application the example effect of blood flow affecting the voice sample is described, and the term "blood flow", in the specification and the claims, is meant to include the effect of a heartbeat on the voice sample.

In some embodiments, a cardiac activity effect comprises blood flow affected by the timing of heart pulses. Alternatively or additionally, a cardiac activity effect comprises blood flow affected by the magnitude of heart pulses. In some embodiments, the effect on the voice sample is used to determine an arrhythmic cardiac condition, for example atrial fibrillation (AF or Afib). Alternatively or additionally, the effect on the voice sample is used to determine an abnormal cardiac condition, for example tachycardia (VT). Alternatively or additionally, the effect on the voice sample is used to determine a healthy cardiac condition, e.g. a cardiac condition having sufficient periodicity in timing and/or magnitude.

In some embodiments, an effect is determined on a subject's voice by sampling the voice as a digital format, optionally during spontaneous speech, and analyzing the digital voice sample to identify a cardiac condition. Alternatively or additionally, effect is determined based on predetermined voiced sounds. In some embodiments, the subject's speech is sampled passively, without active actions taken by the subject himself. In some embodiments, the voice sample is analyzed to extract voice features from it. For example, voice features may include pitch and/or Mel Frequency Cepstral Coefficients (MFCC). Alternatively or additionally, the voice sample, or the voice features themselves, are analyzed to extract cardiac data, such as RR intervals, e.g. time interval between successive heart pulses.

In some embodiments, a variability or change in the heart rate is detected and or measured.

As used herein, the term "voice features" includes any value that can be calculated from the speech, in addition to any statistical and/or mathematical operation of this value, such as derivatives, standard deviation, auto-correlation, coherence, cross-coherence, wavelet transforms, skewedness, etc. The term "voice features" also includes values of changes in speech characteristics over time—such as changes of other voice features over time.

Typically, during speech production, the vocal folds vibrate creating pulses of air. The mass and tension of the vocal folds and the lungs air pressure determine the pitch. The pulses of air change their spectral density and composition according to the mouth\throat structure and volume and create the variety of sounds.

It is noted that the heart beats potentially affect the voice in several mechanisms: change the temporal blood pressure and/or the blood vessels volume. These changes, in the vocal-folds tissue cause small changes in the vocal cord mass which affect the voice;

in addition, blood pressure and heartbeats may also cause small changes in the volume of the nasal and/or oral cavities, which may also affect the speech;

the heart beat creates a "mechanical pulse", vibrating the lungs, vocal cords and/or mouth, potentially causing modulation of the speech;

the pulsations of the large artery that passes through the neck potentially cause mechanical vibration to the vocal folds.

Atrial fibrillation (AF) is typically identified by irregular heart rhythms and is clinically defined as uncoordinated contractions of the atria. AF may be asymptomatic. The presence of AF makes strokes up to five times more likely. Current medical practice manages to prevent about 80% of AF-related strokes. It is therefore a potential advantage to identify subjects suffering from AF early in order to begin medical treatment.

Some methods of detecting AF are primarily reliant on the use of continuous ECG recordings (e.g. cardiac holter monitors, mobile cardiac telemetry monitors etc.). Continuous measurements are typically needed since AF may occur only for several minutes per day and is non-symptomatic. However, continuous cardiac monitoring via ECG may present challenges, such as the precise application of a variety of electrodes, an uncomfortable apparatus, cabling, wearable sensors and issues with battery replacement or recharging. A passive monitoring has the potential advantage of identifying cardiac conditions without provoking active action steps from the screened subjects, and without having to deviate from everyday routines.

In some embodiments, a voice is sampled by a voice input, such as for example, a microphone device. Optionally, the voice input forms a part of a phone. Alternatively or additionally, the voice input forms a part of a computer and/or smartphone. Alternatively or additionally, the voice input forms a part of a car multimedia system, and/or speaker phone, and/or other relevant system at the car. Alternatively or additionally, a voice input includes a voice service (such as Alexa®). Alternatively or additionally, a voice input forms a part of a smart watch, and/or other wearable means having a microphone, and/or personal monitors (cellular and/or portable). In some embodiments, a voice sampling and/or analyzing module forms part of a panic alarm button having a microphone, optionally being a private application or related to a medical emergency service.

In some embodiments, voice sampling is initiated by the subject. Alternatively or additionally, voice sampling is initiated by the sampling device having the voice input, optionally, according to a predetermined schedule, for example, obtaining a voice sample every 5 minutes, once an hour, twice a day, and any regimen more or less frequent. In some embodiments, a plurality of voice samples is obtained and analyzed over time. A potential advantage of obtaining a plurality of tests is an improvement in the specificity and/or sensitivity of the test results and diagnosis. In some embodiments, the number of voice samples, and/or the time interval between sampling, is determined based on the estimated probability to detect the cardiac condition. For example, when looking for an AF episode suspected to occur once a week, a different regimen of testing, possibly more frequent, would be provided than when looking for an AF episode occurring every hour.

In some embodiments, a cloud server, private and/or public, is used for analyzing the voice sample. In some embodiments, voice is sampled and at least partially analyzed at a telephone switch or a call center, for example, when a subject calls to seek a cardiac condition estimation service. In some embodiments, a server is collocated with the telephone switch and gets the data from the switch.

Alternatively, a subject calls to seek a difference service, but receives cardiac condition estimation service by the same call. Optionally, analysis results are sent to the subject. Alternatively or additionally, they are sent to a caregiver. Alternatively or additionally, they are stored in a database until asked for, or paid for. In some embodiments, the database and/or a permanent memory is used as a reference for analyzed voiced samples.

In some embodiments, analysis is performed by circuitry and/or software in a smartphone, and/or CPU-based device, and/or server. In some embodiments, the circuitry has instructions to process the voice sample and estimate the speaker's cardiac condition. A potential advantage of passively using existing infrastructure, is that passive monitoring of heart diseases can be made, optionally providing warning indications and/or recommendations for further medical checkup in case of potential concerns, potentially without an active action taken by the sampled subject. Another potential advantage is a high chance for early detection due to the accessibility of the test in everyday life. An early detection can provide early intervention to prevent stroke and other complications, potentially preventing re-hospitalizations and/or death.

In some embodiments, telephone conversation are encrypted at a first station and decrypted at a second station. In such embodiments analysis of the speech is optionally performed by circuitry and/or software in the first station or in the second station, optionally analyzing the unencrypted speech.

In some embodiments, a characterizing parameter of an effect is compared to a threshold, or a reference. In some embodiments, the reference value is taken from the same subject but at samples which are known to be healthy and/or pathologic. A potential advantage of comparing an effect to a self-reference is the ability to identify changes occurring in the sampled individual, and optionally determine a cardiac condition based on these changes. Alternatively or additionally, the reference is provided from a database having a plurality of references associated with healthy and/or as having a cardiac pathology. Alternatively or additionally, the characterizing parameter is compared to a threshold which is predetermined to be with a cutoff to determine a cardiac condition, for example being lower than the threshold would be determined as a healthy condition and higher would be determined as a pathologic condition. In some embodiments, a cutoff value can be used to calculate the probability of the subject to have pathology.

In some embodiments, a threshold or a multi-dimensional threshold is optionally dynamically determined based on machine learning, optionally using other data derived from the voice sample. In some embodiments, a training set contains voice features calculated from other patients with the pathology and without. In some embodiments, a classifier is chosen for optimal separation of the training set and high separation on a separate test set. For example, these methods may include SVM, regression, PCA KNN and more.

In some embodiments, integration of several voice sample analysis methods is performed. In some embodiments, a different weight is assigned to each analysis method, optionally based on the specificity and/or sensitivity of the analysis result. In some embodiments, machine learning is used to dynamically determine the weight of each analysis. Optionally, other data is used in the integration process, such as the subject's medical history, and/or family history, and/or physiological tests results.

In some embodiments, a severity of an arrhythmic cardiac condition is determined, optionally based on the integrated results. Optionally, a severity of an arrhythmia is determined according to the number of identified episodes, for example, the number of identified AF episodes. Alternatively or additionally, severity is determined based on the time interval between identified episodes, and/or their duration. Alternatively or additionally, severity is determined based on the extent of the determined effect over the voice sample, for example, the more irregular a voice sample is, the more severe the pathologic condition which is determined.

In some embodiments, after determining a cardiac condition, a validation test is performed, optionally in the form of a second voice sample. In some embodiments, a second voice sample comprises predetermined words or vowels. Alternatively or additionally, a validation test includes an electrocardiogram (ECG) test and/or a photoplethysmography (PPG) test and/or designated mobile applications for performing ECG and/or PPG tests. A potential advantage of using complement testing is raising the specificity and the sensitivity of the diagnosis.

In some embodiments, the effect of blood flow over the voice is used to identify the heart rate and/or variability or change in the heart rate, which are used to identify an emotional condition, such as for example, stress, anger, nervousness, excitement and so forth. Alternatively or additionally, voice analysis is used to determine the fitness level of the sampled subject. Alternatively or additionally, the voice analysis is used to determine a general health and/or a clinical state of the sampled subject.

Extracting Effects of the Timing of the Cardiac Activity on the Voice

An aspect of some embodiments of the invention relates to determining a cardiac condition based on detecting the effect the timing of the cardiac activity has on the voice, for example, by detecting the effect of the timing of the heart pulses on the blood flow which affects the voice. It is estimated that an irregular heart pulse rate would have irregular occurrences of heart pulse effects that will affect the blood flow which will manifest in the voice.

In some embodiments, timed cardiac data is extracted from voiced segments of a voice sample. For example, timed cardiac data includes at least one RR interval. Optionally, the R apexes are non-successive. As used herein, the term "R" refers to the timing of the peak of the blood pressure during heart pulse. RR is the distance in time between two successive heart pulses. In some embodiments, cardiac parameters are extracted from spontaneous speech.

Spontaneous speech is typically compounded from voiced sounds, unvoiced sounds and silence. As used herein, voiced sounds are the parts of the speech where the vocal cords are closed and vibrate such as \a\ phoneme as in "cat", unvoiced sounds are parts of the speech where vocal cords are open such as \sh\ phoneme as in "shame", and silence periods are parts where no speech is present (such as pauses). It is estimated that heart activity affects mainly the voiced sound, while unvoiced sounds are less affected by it, and silenced periods are not affected at all. Voiced segments during spontaneous speech are relatively short, usually lasting less than 3 seconds. In some embodiments, cardiac conditions are estimated from non-continuous, fragmented speech data. Optionally, fragmented speech data is extracted from voiced segments of spontaneous speech. In some embodiments, the voice sample is classified to identify voiced segments, and optionally, the voiced segments are concatenated such that at least some segments are removed and remaining segment ends are smoothed.

In some embodiments, voiced sounds are classified by standard speech classification methods, for example such as recited in Yingyong Qi and Bobby R. Hunt, Voiced-Unvoiced-Silence Classifications of Speech Using Hybrid Features and a Network Classifier, Yingyong Qi and Bobby R. Hunt, 1993, incorporated herein as references in their entirety.

In some embodiments, heart pulse data is derived from intermittent voiced segments. In some embodiments, heart pulse data, and/or blood flow behavior, are extrapolated from segments which are not voiced, optionally found between two voiced segments having suggestive trends for the occurrence of a pulse. In some embodiments, a time interval between two occurrences of R pulses is sufficient to determine a cardiac condition. For example, when identifying a time interval characterizing an abnormally high heart rate condition, such as ventricular tachycardia. Alternatively or additionally, at least three occurrences of R pulses are sufficient to determine an arrhythmia, such as AF. In some embodiments, an arrhythmic cardiac condition is determined by calculating time intervals between the three consecutive occurrences of heart pulses. In some embodiments, a larger number of consecutive R pulses occurrences provides a higher sensitivity and/or specificity of the test, for example, a number of more than four, and/or more than five, and/or more than six, and/or more than seven, and/or more than eight and/or larger number of consecutive occurrences. In some embodiments, the time intervals between the identified heart pulses are matched with reference time intervals obtained from a reference heart condition, known to be healthy or pathologic and/or arrhythmic. Optionally, a matching probability is calculated and compared to a threshold for determining the cardiac condition.

An aspect of some embodiments of the invention relates to estimating a cardiac condition by looking for variations of specific parameters that carry relevant information from the voice over time. For example, by analyzing voice features over time and calculating a periodicity of the values of the voice features. In some embodiments, voice features are extracted from a voiced sample, optionally a spontaneous speech. In some embodiments, voice features include, for example, a weighted spectrum, and/or Linear Predictive Coefficient (LPC) and/or LPC based spectrum, and/or Mel Frequency Cepstral Coefficients (MFCC), and/or fundamental frequency (pitch), and/or energy, and/or zero crossing, and/or formants, and/or glottal pulse (vocal cord pulse), and/or jitter, and/or shimmer, and/or fractal dimension, and/or coherence, and/or wavelet analysis, or any other mathematical\statistical presentation of the speech samples.

In some embodiments, a heart rate of a subject is estimated, optionally by analyzing his voice sample. In some embodiments, a non-uniformity of the voice feature is used to identify irregularities in the timing of the cardiac activity, for example by identifying a periodicity at frequencies at a predetermined range around the frequency of the heart rate. In some embodiments, spectral analysis and/or autocorrelation, is used to identify periodic and/or semi-periodic changes in the voice sample. In some embodiments, periodicity is calculated in a band width of a spectral peak at the predetermined range of the heart rate, of a voice feature. Typically, the wider the band width, the lower the periodicity, and therefore the probability for an arrhythmia is higher. In some embodiments, in order to determine the cardiac condition, the band width is compared to a predetermined threshold.

In some embodiments, a characterizing parameter of the periodicity is compared to a threshold to determine the cardiac condition. For example, a peak of an autocorrelation function (of a voice feature, such as pitch) around the frequency of the heart rate may be characterized by its band width, and a band width of the autocorrelation function having a value above a predetermined threshold would be associated with a high probability for an arrhythmic cardiac condition.

In some embodiments, spectral cross-coherence of the speech is calculated between segments of the speech, optionally around the pitch and\or formant frequencies and\or around any frequencies that are potentially affected by the heart pulse. Coherence reaching lower values for a short period of time can be an indication of heart pulse. In this manner heart pulses can be located on the speech time line.

Extracting Effects of the Magnitude of the Cardiac Activity on the Voice

An aspect of some embodiments of the invention relates to determining a cardiac condition based on extracting the effect of the magnitude of the cardiac activity on the voice. As used herein, the term "magnitude" refers to the extent of the mechanical effect of the blood, such as the blood pressure and/or blood vessels volume and/or an effect of ventricular and/or atrial beat. It is estimated that an irregular heart rate would lead to variability in the magnitude of the blood flow to the vocal region, and would therefore lead to variability in the magnitude of its effect over the voice. It is estimated that the heartbeat modulates the speech, resulting in a variation of the acoustic signals. It is therefore expected that regular heart pulse wave, for example characterized by a sinus rhythm, causes periodic modulation, probably resulting from periodic changes of blood flow through the speech organs. On the other hand, irregular heartbeat, for example AF, causes chaotic changes in blood flow and cause larger variations of the acoustic signals.

In some embodiments, the distribution of the values of the voice feature is determined, for example the standard deviation. In some embodiments, a characterizing parameter of the shape of the distribution is compared to a threshold to determine the cardiac condition. For example, a large width of the shape of the distribution, and/or of the spectral peak values, could be compared to a predetermined threshold which is associated with a high probability for an arrhythmic cardiac condition.

In some embodiments, a multi-feature classifier is optionally used (combining several features) and an optionally multi-dimensional threshold over the multi-dimensional distribution of the values of the voice features is determined, for example using a Support Vector Machine (SVM) method, and/or Vector Quantization methods such as K-MEANS clustering analysis.

In some embodiments, a characterizing parameter of the shape of the multi-dimensional distribution is compared to a multi-dimensional threshold to determine the cardiac condition.

Detecting Atrial Fibrillation

An aspect of some embodiments of the invention relates to detecting atrial fibrillation by its effect on a patient's voice.

In some embodiments, chronic pathological conditions are potentially detected by changes in voice parameters. In some cases Atrial Fibrillation (AF) causes expansion of the Left Atrium (which happens in a majority of pathologic AF cases). The expansion impacts the recurrent laryngeal nerve, causing constant changes of the voice. The changes are potentially manifested in the parameters of the pitch signals and can be analyzed and detected.

This enables to detect AF patients with chronic conditions even in instances where the heart beats at a normal rate.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Voice Sampling and Analysis

Figure 1A:
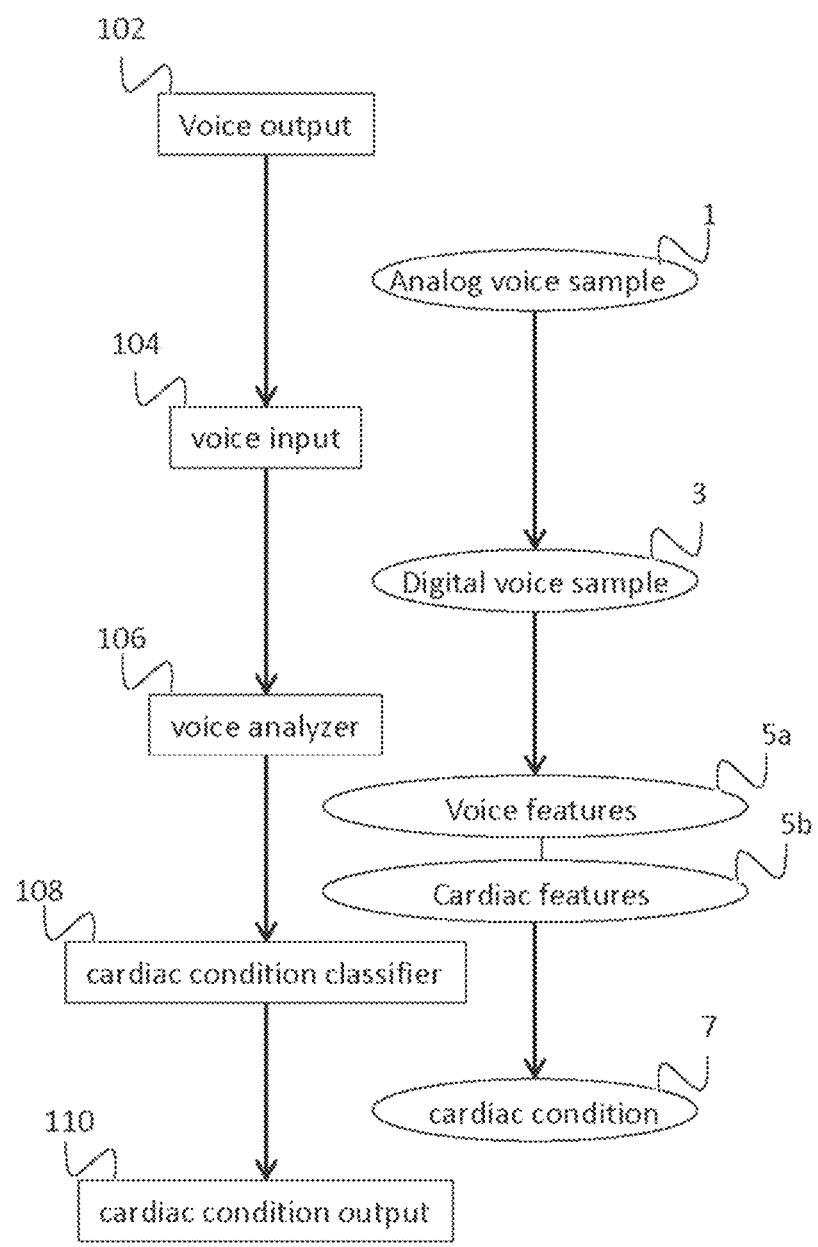
FIG. 1A is a high level flowchart illustrating general voice detection and analysis components and the data flow between them, in accordance with some embodiments of the invention.

Referring now to the drawings, FIG. 1A is a high level block diagram and data flow exemplifying determining cardiac condition from human voice, illustrating participating elements and the data flow between them, in accordance with some embodiments of the invention.

In some embodiments, an analog voice sample 1 is generated by voice output 102, which may include one or more speaking subjects. In some embodiments, analog voice sample 1 is sampled by voice input 104, for example, an electronic device having a microphone, and converted into digital voice sample 3. In some embodiments, digital voice sample 3 is processed by voice analyzer 106. In some embodiments, processing by analyzer 106 identifies voice features 5*a* and/or cardiac features 5*b*. For example, cardiac features may include RR intervals, and/or heart rate, and/or heart rate variability. Examples for voice features may include pitch, and/or formants, and/or Mel Frequency Cepstral Coefficients (MFCC) and/or cross coherence values between frames, and\or wavelet based features, and/or spectral band energies and band width of one or more of the above parameters, and/or fluctuation during utterance and\or derivatives of such features.

Cross Coherence as a speech feature: for a specific frame of speech samples at time (t)—cross coherence is calculated to a frame at time (t+Δn). This value is optionally stored in a vector containing N values:

$$CohVec(t) = [CrossCoh(\text{frame}(t), \text{frame}(t + \Delta)),$$

$$CrossCoh(\text{fame}(t), \text{frame}(t + \Delta^*2)),$$

$$\ldots$$

$$CrossCoh(\text{fame}(t), \text{frame}(t + \Delta^*N))]$$

Wavelet as a feature:

The wavelet transform is optionally used as a speech feature in several ways.

In a first way, in some embodiments, wavelet decomposition is used, optionally using High Pass Filter (HPF) and/or Low Pass Filter (LPF) decomposition.

Figure 1B:
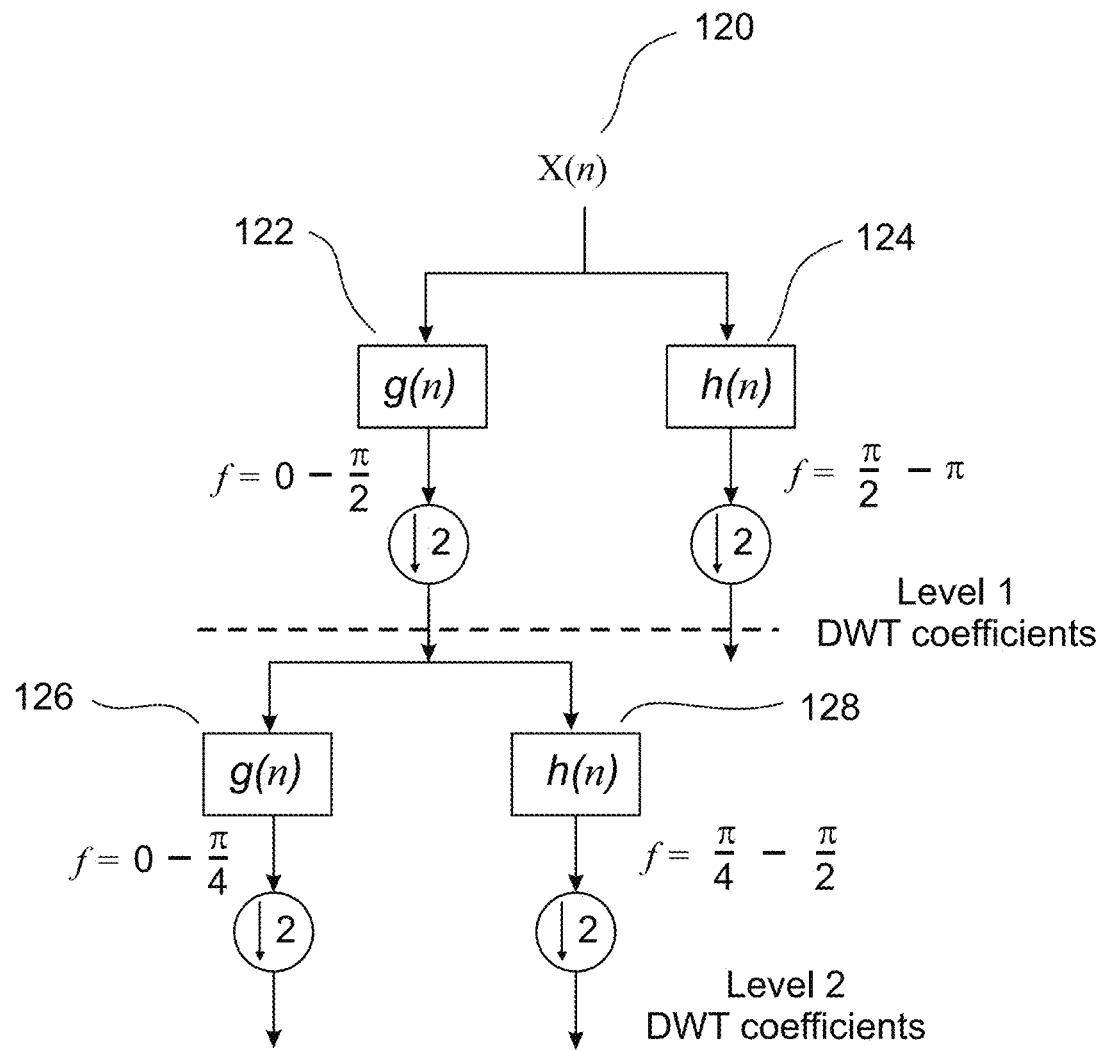
FIG. 1B is a simplified illustration of wavelet decomposition in accordance with some embodiments of the invention.

Reference is now made to FIG. 1B, which is a simplified illustration of a wavelet decomposition by a Discrete Wavelet Transform (DWT) in accordance with some embodiments of the invention.

FIG. 1B shows a signal x(n) 120, producing Level 1 DWT coefficients h(n) 124 and g(n) 122.

FIG. 1B also shows the Level 1 DWT coefficients g(n) 122 optionally producing Level 2 DWT coefficients h(n) 126 and g(n) 128.

FIG. 1B shows an example embodiment where each filter's output energy is used as a component of the output feature vector.

In a second way, in some embodiments, "Scale" and "coefficient" values for each frame are optionally calculated, similarly to energy and frequency using spectrum, and using the values as features.

Spectral energy & BW of fluctuation feature:

In some embodiments the following two step calculation is performed:

calculating a feature vector of the speech utterance, per each frame; and using spectral estimation methods to calculate the spectrum of the feature vectors.

By way of some non-limiting examples, in a case when a feature vector is the pitch frequency (per frame):

FtrVec(n)=Pitch(n), n=1, 2, ..., where N is a frame number,

The spectrum is:

SpecVec=Spectrum_Estimation(FtrVec(1) ... FtrVec(n)).

In some embodiments the SpecVec is optionally used to manifest a frequency by which the feature vector changes over time. Since the heart beats modulates some features of the voice signal, the SpecVec potentially shows a frequency peak at a heart rate frequency.

In some embodiments spectrum estimation is optionally performed by methods such as:

a Fourier transform;
a covariance method;
a periodogram method;
a Yule-Walker method;
a Multiple SIgnal Classification (MUSIC) method; and
an eigenvector method.

In some embodiments the spectral estimation method optionally produces several values per utterance:

Location(s) of spectral peak(s) [Hz];
Band-width(s) of spectral peak(s) [Hz]; and
Energy of spectral peak(s), optionally Band-width*height [Watt].

The above values are optionally used as an indication for heart rate status.

In some embodiments, cardiac/voice features are analyzed by cardiac condition classifier 108 to estimate cardiac condition 7. For example, a cardiac condition may be a healthy cardiac condition, or a pathologic cardiac condition, for example, being identified as arrhythmia and/or AF. Optionally, cardiac condition 7 is presented by cardiac condition output 110, for example a screen.

In some embodiments, voice output 102 includes a human subject generating analog voice sample 1. The human subject may be any person being a candidate for cardiac condition diagnosis using voice. Optionally, voice output 102 includes more than one human subject generating voice sample 1, for example when voice sample 1 contains a conversation between two or more subjects. In some embodiments, only identified speakers are analyzed. In some embodiments, voice sample 1 includes spontaneous speech, for example, a sequence which may comprise segments of user speaking, and/or users conversing, and/or silence periods, and/or background noise, and/or background speakers. Alternatively or additionally, voice sample 1 includes limited speech, for example, specific words and/or vowels, optionally pre-determined or selected from a look-up table.

In some embodiments, voice input 104 records analog voice sample 1 by converting it into digital voice sample 3. In some embodiments, voice input 104 is a device having a microphone. For example, voice input 104 can be a land-line phone, and/or a cellular phone, and/or a computer, and/or speaker-phone, and/or a voice recorder. Alternatively or additionally, voice input 104 is a server which records digital voice sample 3, optionally remote server, for example located in a call center.

Optionally, voice input 104 comprises a database for storing digital voice sample 3. Alternatively or additionally, voice input 104 only converts the sound and transmits it without storing it for long terms. In some embodiments, digital sound sample 3 is stored in a voice data format, for example PCM, and/or WAV, and/or ADPCM. Alternatively or additionally, analog sound is not converted into a digital format, but is analyzed by an analog analysis circuitry which then converts it into a digital format.

In some embodiments, sampling by voice input 104 is provided automatically, i.e. without active action conducted by the subject with regards to the sampling. Alternatively or additionally, the sampling is provided manually, by being operated by an active action of the subject, such as for example, by actively calling a dedicated call center, or by pressing a recording button on a device. Alternatively or additionally, sampling is provided in a pre-scheduled configuration, optionally where the user is asked to speak and/or pronounce certain words or sounds. For example, a service can call a user in pre-scheduled times and sample the conversation. Alternatively, a subject may record digital voice sample 3 in his free time and then transmit this voice sample to a service, for example, by uploading to a server.

In some embodiments, pre-scheduled operation can be initialized from a monitoring infrastructure, and/or from a monitoring application, and/or from medical assistance and/or from the software application after possible risk is detected. In some embodiments, a pre-scheduled operation includes periodic screening. A potential advantage of a periodic screening is continuous monitoring of the subject's condition. In some embodiments, the pre-scheduled operation includes enticing the person to pronounce specific speech, optionally by sending a notification. In some embodiments, the notification includes oral and/or textual alert, and/or a beep sound, and/or a text message to a smartphone, and/or voiced instructions. In some embodiments, a user initiates a test for him and/or his relatives using manual activation of the system. Optionally upon agreement of the user, in some embodiments, a device can be programmed to automatically activate the microphone. In some embodiments, the device can be activated from a remote location, for example through a healthcare service.

In some embodiments, digital sample 3 is classified before going into analysis in voice analyzer 106. For example, for switch/server applications (mass central screening) only selected calls may be analyzed. Optionally, the selection is made based on sample characteristics such as, for example, call duration, and/or noise level, and/or duration of specific speaker voiced segments, and/or duration of voiced segments, and/or speaker identification data, and/or any other criteria that may affect sensitivity and/or the specificity of the diagnosis.

In some embodiments, voice analyzer 106 performs speaker identification. An identification of the speaker may be important for several reasons, such as to know to whom the analysis results should be sent. Alternatively or additionally, speaker identification can be associated with personal information of the speaker, which is optionally used to assist in the clinical diagnosis. For example, personal information may include weight, and/or smoking habits, and/or previously known pathologies, and/or prior medical diagnostics. In some embodiments, user identification helps to identify a single speaker from a plurality of speakers, and/or from a conversation in which voice samples alternate between participants. Optionally, following the identification, voice analyzer 106 separates the voice segments of a subject from voice segments having other speakers.

In some embodiments, only identified speakers will be analyzed. Optionally, a speaker would be analyzed upon request. Alternatively, a speaker would be analyzed once a payment for the service has been received. Alternatively, a speaker would be analyzed if he is identified as a member of a group, for example, being a member of insurance or a health maintenance organization.

Optionally, a subject's voice is identified using a database having pre-identified speakers. In some embodiments, for example, in cases that several users use the same analysis device, separation between the users can be obtained by building a voice signature and/or using other details related to the speech and\or other parameters such as, for example, a caller identification number. Alternatively or additionally, the user is identified by pronouncing a pre-determined word, or list of words.

In some embodiments, for some applications (such as monitoring in telecom network) if the speaker identification is unknown, but the system found a probability of heart pathology, the analysis results are stored, optionally in the system data-base. In such cases, in some embodiments, results are stored using alternative classifications, such as, for example, a phone number and/or a caller ID, and/or International Mobile Equipment Identity, etc. For example, during mass screening at a call center, when a diagnostic result is stored in the system database, it is saved according to a speaker personal file if the speaker is registered or under caller information if the speaker is unknown.

In some embodiments, digital voice sample 3 is stored for future uses other than estimation of the cardiac condition of the speaker. Optionally, a database containing voice samples, and/or analyzed voice samples, and/or diagnostic results is used in future analyses of other voice samples. Alternatively or additionally, such a database is used for epidemiological research, for example, in order to have statistical knowledge regarding the monitored pathology.

In some embodiments, processing voice sample 3 is performed by voice analyzer 106, including, for example, smart phone circuitry, and/or remote server (cloud computing), and/or circuitry running at a standalone device (such as PC, and/or tablet), and/or a server at a call center, for example, where a person can initiate a call and his voice would be recorded and analyzed.

In some embodiments, voice analyzer 106 is embedded in the same device as voice input 104. For example, a smartphone may have a microphone 104 for sampling an analog voice sample 1, converting it into digital voice sample 3 and also have voice analyzer 106 (such as circuitry and\or software that perform signal processing) for analyzing the voice, optionally to derive voice features 5a and/or cardiac features 5b.

Alternatively or additionally, voice analyzer 106 is in a different device than voice input 104, and/or in a different geographical location. For example, a smartphone may have a voice input 104 (such as a microphone), but digital voice sample 3 may be transmitted to a remote server having voice analyzer 106 circuitry.

Alternatively or additionally, both voice input 104 and voice analyzer 106 are remote from the voice output 102. For example, when a subject calls a call center and his voice is recorded in a server found at the telecom network and being analyzed by that server as well.

In some embodiments, voice analyzer 106 extracts voice features 5a from digital voice sample 3. For example, voice features 5a may include a weighted spectrum, and/or Linear Predictive Coefficient (LPC) and/or LPC based spectrum, and/or Mel Frequency Cepstral Coefficients (MFCC), and/or fundamental frequency (pitch), and/or energy, and/or zero crossing, and/or formants, and/or glottal pulse (vocal cord pulse), and/or jitter, and/or shimmer, and/or fractal dimension, and/or coherence, wavelet analysis, or any other feature that extracts relevant information from the speech samples (such as: energy, and/or mean power, and/or entropy, and/or the like).

Alternatively or additionally, voice analyzer 106 extracts cardiac features 5b from the digital voice sample 3, and/or from voice features 5a. In some embodiments, cardiac features 5b include pulse data, for example RR intervals. Alternatively or additionally, cardiac features include heart rate and/or heart rate variability.

In some embodiments, a cardiac condition classifier 108 processes voice features 5a and/or cardiac features 5b and estimates a cardiac condition 7. In some embodiments, cardiac condition classifier 108 determines the probability a subject has arrhythmia. Alternatively or additionally, cardiac condition classifier 108 determines the probability a subject has atrial fibrillation. Alternatively or additionally, other cardiac conditions are determined, for example, acute coronary syndrome and/or warning signs of embolic stroke, and/or myocardial infarction and/or sudden cardiac arrest, and/or ventricular flutter, and/or atrial flutter, and/or atrial tachycardia, and/or ventricular tachycardia, and/or Bradycardia, and/or dyspnea, and/or chest pain.

Optionally, the estimated cardiac condition 7, and/or the voice features 5a, and/or the cardiac features 5b are presented in cardiac condition output 110. In some embodiments, cardiac condition output 110 includes a screen, for example, a monitor and/or a display of a device. In some embodiments, cardiac condition output 110 includes a notification to the speaker and/or caregiver of the speaker. Examples for notifications may include text message, and/or email, and/or phone call, and/or messaging applications (such as WhatsApp, Facebook and other means selected by the user). Alternatively or additionally, a notification may be a graphical presentation. Alternatively or additionally, a notification may be in the form of visual and/or audio notification. For example, a speaker phone embedded in a vehicle and having an application providing speaker analysis, in accordance with some embodiments of the invention, may be connected to a notification infrastructure of the vehicle, such as a blinking light, or a vocal notification through the speaker system in the vehicle.

Exemplary Data Flow

Reference is now made to FIG. 2, illustrating a data flow map of some options of data transfer between optional voice analyzing stations, in accordance with some embodiments of the invention.

In some embodiments, at least one subject 220 outputs an analog voice sample 1 in a range of a voice input, e.g. a device having a microphone, such as a voice recorder and/or a feature phone, exemplified in feature phone 240. Alternatively or additionally, voice input could be a module in a smart device, for example a personal computer, and/or a smartphone and/or any other phone device (such as a wireless phone, and/or speaker phone) and/or a tablet, exemplified as tablet 260. In some embodiments, the voice input in 240 and/or 260 converts analog voice sample 1 into digital voice sample 3.

In some embodiments the voice input is optionally to a wearable microphone (not shown), optionally connected by wire or wirelessly to a computing unit for analysis or to a transmitting unit for transmitting to a computing unit for analysis.

In some embodiments, digital sample 3 is transmitted to an analyzer, such as server 262, which could be a remote server or a cloud server. Alternatively or additionally, digital sample 3 is transmitted to call center, where it is optionally recorded and then analyzed. Alternatively or additionally, digital sample 3 is transmitted to a telephone switch 265, for example, by configuring digital sample 3 to pass through a telephone switch 265 first, before directed to a call center 290. For example, a subject may call to speak with a governmental or private sector customer service located at 290, but upon consent his voice would transfer through switch 265 to be analyzed for estimating a cardiac condition. In some embodiments, a call center comprises a service for people who want to be analyzed. Alternatively or additionally, a call center comprises a service for other purposes than cardiac condition diagnosis. For example, a call center for governmental service may include voice sampling for diagnostic purposes a side service. Other examples for telecom services include health telecom services, and/or emergency call centers, and/or medical services, and/or insurance services, and/or personal virtual assistants.

Alternatively or additionally, smart device 260 also has instructions for analyzing digital sample 3 and optionally transmitting output, for example in the form of cardiac and/or voice features 5 and/or an estimated cardiac condition 7. In some embodiments, output is transmitted directly to caregiver 280. Alternatively or additionally, is transmitted to a server 262 for further analysis and/or for storage. Alternatively or additionally, output is transmitted to a call center 290, with or without passing through switch 265, and optionally from there transmitted to caregiver 280. In some embodiments, output is provided back to the analyzed subject 220.

In some embodiments, circuitry is configured to report to the user on the current state of atrial fibrillation. Such circuitry may be implemented in smartphones 240 and/or cloud servers 262, private and/or public. A potential advantage of using existing infrastructure is no additional radiation for either sensing and/or data transferring, as opposed to for example, an external wireless device for recording and/or analyzing and/or transmitting.

In some embodiments, local assessment is provided. For example, local assessment is provided when the same device both samples the voice and analyzes it, such as a smartphone both sampling the voice and analyzing it to extract features and/or cardiac condition. Optionally, local assessment is provided by manual operation. Alternatively or additionally, local assessment is automatically operated, for example by operating each time a subject uses his phone, and/or by periodically sampling voice by the device.

Alternatively or additionally, remote assessment is provided. For example, remote assessment is provided when the voice sampling occurs in one geographic location while at least a portion of the analysis of the voice sample is provided in a different geographic location. For example, a subject may be sampled by a phone, but the sampled voice may be transmitted to be analyzed by a remote sever (cloud, cellular, landline). In some embodiments, telecom network components, such as BTS, and/or MSC or servers\cloud, and/or switch are equipped with analysis circuitry. In some embodiments, analyzing circuitry is provided in VoIP servers, such as Skype, WhatsApp, Viber, conference calls, video messages and/or recordings and the like. In cases of encrypted communication, in some embodiments, relevant voice features that contain cardiac information are calculated at the device before encryption and are optionally analyzed locally, or alternatively or additionally, sent to remote analysis in a server.

In some embodiments, speaker identification is used to identify the subject through his voice. For example, when a person calls a call center 290 to get service, circuitry adapted for voice analysis may be also configured to identify the subject, for example, the user phone number can also be used, optionally in order to trace him back and notify his detected condition. In some embodiments, at least one subject, or a plurality of subjects, may be detected from a plurality of simultaneously sampled voices, such as when sampling a conversation and/or a conference call.

Exemplary High Level Overview

Figure 3:
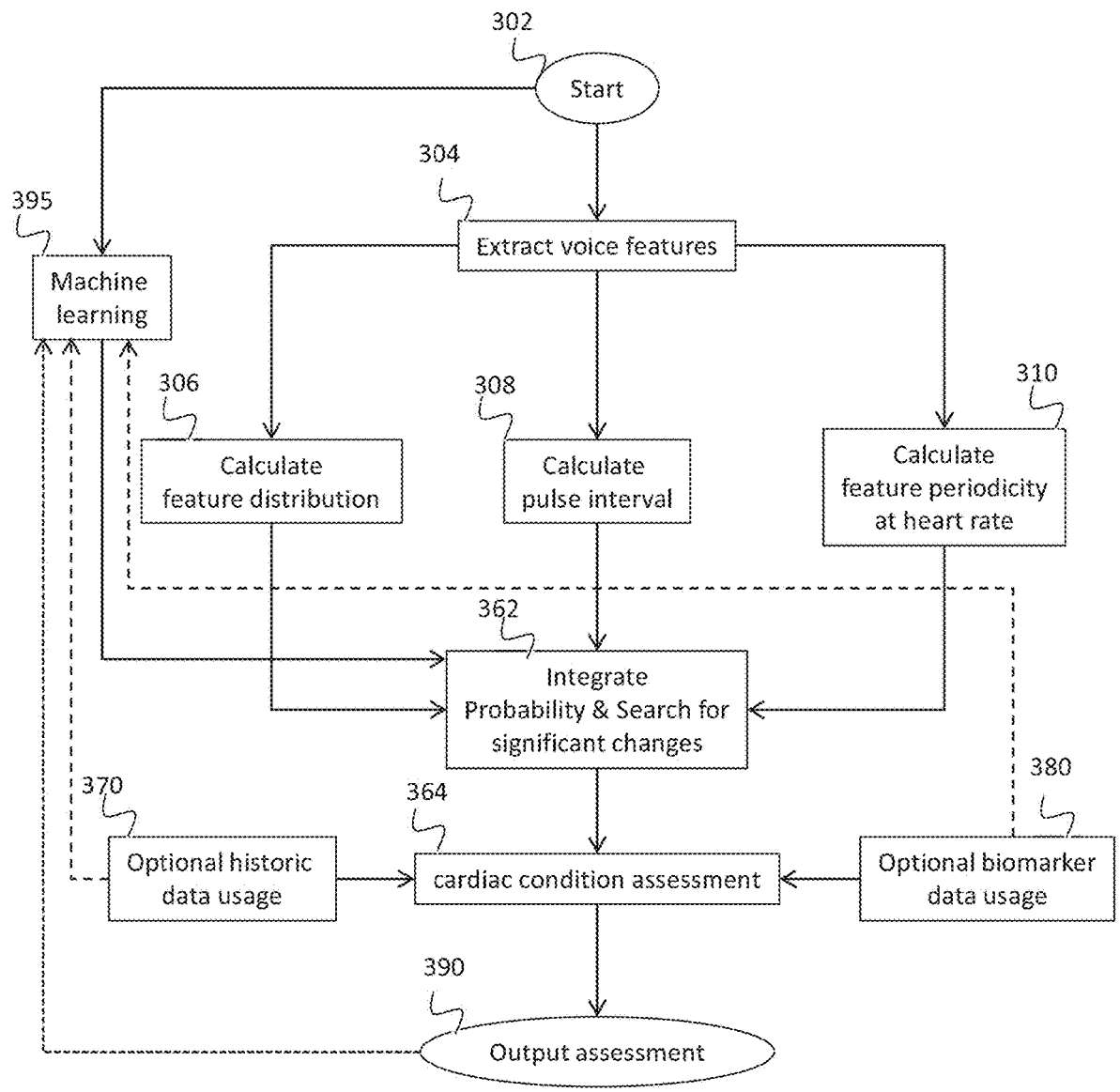
FIG. 3 is a general high level overview of cardiac condition estimation based on a voice sample, in accordance with some embodiments of the invention.

Reference is now made to FIG. 3 illustrating a general high level flow chart for cardiac condition estimation based on a voice sample, in accordance with some embodiments of the invention.

In some embodiments, analysis starts at 302 by obtaining a voice sample, optionally fragmented and/or classified, for example as shown in FIG. 5A. In some embodiments, voice features are extracted at 304, optionally in the form of voice features vector per each fragment of the voice sample.

In some embodiments, a voice sample and/or voice features are used to calculate voice feature distribution, and/or calculate any mathematical operation to reveal relevant information at 306. For example, a distribution such as the variability of a plurality of values of a voice feature is calculated. It is estimated that voice features are affected by the blood flow to the vocal organs which is affected by the pulse timing and power\strength. It is thus estimated that an irregular pulse, such as found in arrhythmia, would result in irregular effects over the voice feature, which would manifest in a high variability of the voice feature values. Voice feature distribution is further detailed and exemplified in FIGS. 6A-6B, 7A-7B, 8A-8B, 9A-9B and 10A-10D.

Alternatively or additionally, a voice sample and/or voice features are used for calculating the time interval between heart pulse occurrences at 308.

In some embodiments, temporal changes in a voice feature values are used as indication of heart pulses. Locating the temporal changes on a time-scale gives approximation of heart pulse locations.

In some embodiments, a voice sample is used to identify pulse occurrences and calculate time intervals between consecutive occurrences. In some embodiments, a plurality of time intervals is put together as a sequence. In some embodiments, a heart condition is estimated based on the sequence. Pulse extraction is further detailed and exemplified in FIGS. 11A-11D, 12A-12B, and 13.

Alternatively or additionally, a voice sample and/or voice features are used to calculate voice feature periodicity around the heart rate at 310. For example, a voice feature can be subjected to autocorrelation calculation at the heart rate value. It is estimated that influence of the pulse over the voice feature would be periodic when the heart pulse is in a healthy condition, but would be irregular when the heart pulse is arrhythmic. A periodicity calculation, such as autocorrelation, can reveal how regularly a voice feature is affected. Further details and examples follow in FIGS. 14A-14B, 15A-15D.

In some embodiments, results of the analyzed patterns are integrated at 362 to provide an overall probability of a cardiac condition, and reach a cardiac condition assessment at 364.

In some embodiments, the analysis module (362) stores the values obtained from the speech analysis on an ongoing basis in each of the three methods listed herein. Optionally, the system learns these values; they are defined as "normal values" that define a healthy condition for the specific monitored person. In some embodiments, during ongoing monitoring of the specific person, the system compares the stored (normal) values to the current values and measures the relative change level. In some embodiments, the amount of changes in the values compared to the "normal values" is proportional to the probability of having the pathology.

Optionally, cardiac condition assessment also takes into consideration the medical and/or personal history data of the examined subject at 370. Alternatively or additionally, biomarker tests are taken into consideration at 380

Examples for biomarkers include any one or a combination of weight, gender, occupation, historical diagnosed diseases and AF episodes, smoking habits, CHADS2 (congestive heart failure history), hypertension history, age, diabetes mellitus history, stroke and TIA (Transient Ischemic Attack) symptoms.

In some embodiments, cardiac condition assessment is presented to a user through an output 390, for example a display.

Optionally, obtained data is used for machine learning at 395. For example, voice samples, processed voice data, voice features, historical data, biomarker data and/or cardiac condition, could be used to generate rules and statistical characterizations for more accurate diagnostics in future processes, and to assist in the integration conducted at 362.

In some embodiments, the machine learning includes training stage. For example, in the training stage, voice samples, and/or voice features and/or cardiac features might be taken from healthy subjects and subjects known to have a cardiac pathology, and used as a reference. For example, based on this data, the stage will give to most appropriate algorithm to separate between healthy and pathological speech. During operating stage that machine learning model will calculate probability of pathology from the user voice (and/or features) and will assist in the decision making.

Additionally or optionally, Voice features may then be calculated for selected frames of the voice sample and spectral representation may be calculated for each feature. Based on the spectral analysis of each population, training statistical models may be formed to characterize healthy profiles and training statistical models may be formed to characterize non-healthy profiles.

Optionally, a classifier is provided to distinct between the two training statistical models. Alternatively or additionally, the probabilities are compared and a decision is made accordingly.

In some embodiments, the process disclosed in the flow chart of FIG. 3 can be used to identify a variety of cardiac conditions, whether arrhythmic or otherwise. For example, diagnosing atrial flutter, and/or ventricle tachycardia, and/or premature ventricular contractions (PVC) and/or abnormal cardiac rhythm and/or ectopic beats are based on similar evaluations as depict previously, optionally with adjustment of the integration process at 362 and/or the assessment at 364 to the specific abnormal cardiac rhythm determined. Alternatively or additionally, adjustment is made to the thresholds and/or references used in assessing feature distribution at 306, and/or pulse interval at 308, and/or periodicity at 310.

When detecting abnormal cardiac rhythms, such as ventricle tachycardia or bradycardia, in some embodiments, the process is similar to the depicted above but with a few changes. For example, at 308—in some embodiments, by looking for a very high or low pulse intervals—for example, higher than 200 BPM (tachycardia) or lower than 60 BPM (bradycardia). In some embodiments, at 306—other parameters characterizing the distribution are calculated. In some embodiments, at 380—important input is the monitored person age (above 60 years).

In some embodiments, for detecting atrial flutter, and/or PVC, and/or any other type of arrhythmias, the process shown in FIG. 3 is followed but with different thresholds and parameters values.

In some embodiments, for detecting Dyspnea and/or chest pain, the same process is used but with different voice features, and/or thresholds and/o parameters values.

For example, for all the above pathologies the detection can be based on:

(1) Estimating heart pulse timing (RR interval) for detecting heart rhythm and comparing it to a rhythm known to be pathological/healthy.

(2) Calculating periodicity of speech features (autocorrelation and/or spectral domain) and comparing it to a periodicity known to be pathological/healthy.

(3) Using machine learning strategy to train statistical models from voice features from healthy speakers and/or from speakers having pathology.

In some embodiments, the process is used to identify a healthy cardiac condition, for example, by identifying a sinus rhythm.

In some embodiments, for unknown speakers—the pathology will be detected by comparing, for example by probability calculations, the acoustic features to each of the pathological and/or healthy models (such as the models that were calculated in the training phase) and taking the highest probability model as the result.

Exemplary Apparatus for Voice Sampling and/or Analysis

Reference is now made to FIG. 4A-B schematically illustrating voice sampling and/or analysis in exemplary platforms, such as a mobile phone in FIG. 4A and a vehicle in FIG. 4B, in accordance with some embodiments of the invention. Optionally, the system can be implemented in any voice platforms and/or voice assisting platforms.

In some embodiments, vehicles are used for embedding with sampling and/or analyzing circuitry. For example, a voice input and/or analyzer can be embedded in a car multimedia system and/or speakerphone system; for example, by sampling when a subject is talking on the phone/speaker in the car, and/or outputting voice commands, and/or spontaneously talking inside the car.

In some embodiments, a phone and/or smartphone are used for sampling a voice sample using a voice input 422, for example a microphone. Optionally, analysis of the voice sample is also conducted in the phone by circuitry having instructions for such an analysis. In some embodiments, a voice processor 420 is used to process the voice sample, as further illustrated in FIGS. 5A-C. In some embodiments, voice processor 420 cleans the voice sample at voice filtering unit 424, for example by filtering and/or classifying and/or segmenting into fragments. For example, filtering unit 424 may remove noises and "clean" the signal of the sampled voice. In some embodiments, filtered, or non-filtered, voice is further subjected to classification. Optionally, the voice sample is classified into speech and/or non-speech parts and/or silence parts and/or transition parts. In some embodiments, filtering unit 424 is used to detect and mark the location of the relevant speech data from the voice stream, optionally by using a sound criterion. For example, a sound criterion may be an energy, and/or zero crossing, and/or formants, and/or pitch. For example, in the voiced parts, an autocorrelation analysis exhibits a significant peak in the pitch frequency which is optionally used for voiced\unvoiced classification.

In some embodiments, feature extractor 426 extracts data from the voice sample, for example voice features and/or acoustic vectors and/or cardiac features. In some embodiments, at least one value of a voice feature is calculated per frame. For example, voice features may include a weighted spectrum, and/or Linear Predictive Coefficient (LPC) and/or LPC based spectrum, and/or Mel Frequency Cepstral Coefficients (MFCC), and/or fundamental frequency (pitch), and/or energy, and/or zero crossing, and/or formants, and/or glottal pulse (vocal cord pulse), and/or jitter, and/or shimmer, and/or fractal dimension, and/or coherence and/or wavelet analysis, or any other feature that extracts relevant information from the speech samples. Alternatively or additionally, a combination of some or all of the voice features is used into a single high dimension vector containing multiple features, optionally including statistical weights for each parameter, as further demonstrated in FIG. 5A.

In some embodiments, voice features and/or acoustic vectors and/or cardiac features are analyzed at feature processor 440. In some embodiments, pulse interval calculator 442 is used to calculate time intervals between heart pulses. Alternatively or additionally, voice feature distribution calculator 444 is used to characterize the distribution and/or variability of at least one voice feature. Alternatively or additionally, voice feature periodicity calculator 446 is used for identifying regularities in changes over time of at least one voice feature.

In some embodiments, the outcome of the feature processor 440 is analyzed by cardiac condition classifier 460 to estimate the probability of a cardiac pathology using various statistical methods. In some embodiments, probability integration module 462 is used to weigh the various outcomes of feature processor 440, which could be any combination of the results of calculators 442, 444 and 446. In some embodiments, a cardiac condition assessment module 464 uses the weighing result of probability integration module 462 to derive cardiac condition estimation. In some embodiments, probability integration module 462 and/or cardiac condition assessment module 464 exchange data, transmit and/or receive, with machine learning module 466.

Optionally, as exemplified in FIG. 4B, system 400 for cardiac condition determination, is embedded in a compartment for housing a subject 450, such as for example vehicle 402. In some embodiments, system 400 is integrated with the multimedia system of the car, and/or any other computational hardware. In some embodiments, system 400 is configured to input a voice sample 420 from subject 450. In some embodiments, system 400 comprises circuitry for performing at least some of the analysis of the cardiac pathology. Alternatively or additionally, the voice sample and/or at least a partially analyzed sound sample are transmitted, for example, through a multimedia system of a connected car, to a server for further analysis. In some embodiments, results are sent to subject 450 directly, for example, through a smartphone and/or email. Alternatively or additionally, output is presented to the user through the car interfaces, such as for example, though the multimedia system, and/or speakers, and/or dashboard interface (such as in the form of a warning light). Alternatively or additionally, results are sent to a caregiver.

Exemplary Voice Sample Processing

Reference is now made to FIG. 5A, illustrating exemplary voice processing, in accordance with some embodiments of the invention. In some embodiments, it is potentially beneficial to divide obtained voice sample into frames, potentially having cardiac and/or voice feature information, and possibly remove frames which are less likely to provide such information.

In some embodiments, a voice sample is filtered at 502, for example to remove noise and/or distortion. Optionally, voice filtering includes sound reduction and/or active noise cancellation techniques. A potential advantage of filtering, for example by attenuating background noises and/or voice distortions, is potentially increasing efficiency of later processing. In some embodiments, filtering is done by active noise cancellation—where the noise is subtracted from the speech. Alternatively or additionally, filtering is done by noise filtering in the time domain or frequency domain.

In some embodiments, the voice sample is classified at 504. It is estimated that blood flow following a heartbeat causes modulation of the speech signal. In some embodiments, to extract cardiac and/or acoustic information from the speech signal, the speech signal is optionally classified into four classes: (i) silence\background noise fragments—typically having no relevant information, (ii) unvoiced fragments—typically having minor information, (iii) voiced fragments, estimated to have relevant information and (iv) transition parts defined as parts of the speech where the vocal organs change their structure (e.g. the mouth cavity orientation, and/or the tongue position, and/or the lips position, and/or the vocal cords configuration) between one sound to another. Optionally, after classification, non-speech (and/or noise) segments are removed. Alternatively or additionally, unvoiced segments are removed. In some embodiments, classification is made on the voiced segments to include or exclude a particular vowel, for example, only /ah/ vowels, or only /eh/ vowels, or only /oh/ vowels, or only /uh/ vowels, or only /eeh/ vowels.

In some embodiments, the speech sample is divided into $\{m\}$ frames at 506, for example, having length of about 0.1 msec to about 400 msec. Alternatively or additionally, frames have length of about 20 msec to about 40 msec. Optionally, the frames are overlapping, for example an overlap of 10%, and/or 20%, and/or 30%, and/or 40%, and/or 50%, and/or 60%, or an overlap in the range of 1% to 99%.

In some embodiments, for each frame $\{m\}$, $\{j\}$ voice features are calculated at 508, such that, for example:

Voice feature vector $\{j,m\}=Fj\{Speech\_frame(m)\}$ calculated from speech samples at frame $\{m\}$ $$Speech\_frame(m)=Speech(t+Ts*m), Speech((t+1)+Ts*m) \ldots Speech((t+Tw)+Ts*m)$$

Where:

(m)—frame number (t)—samples time index (t=1/Fs where Fs=sampling frequency usually between 6 Khz to 100 Khz)

(Ts)—frame step (if Ts=Tw there is no overlap, Ts=0.5*Tw is 50% overlap)

(Tw)—Frame size (duration)

(Speech)—samples of speech

F{ } is the function of speech samples=Voice features which are alternative representation of the information of the speech. For example: Spectrum, and/or MFCC, and/or LPC, and/or autocorrelation, wavelet features etc.

In some embodiments, the time derivatives (any order) are also calculated for each feature at 510, for example:

$$\text{First derivative: } Diff1(j, m) = \frac{d}{dm} Acoustic_{parameter(j,m)}$$

$$\text{Second derivative: } Diff2(j, m) = \frac{d}{dm} diff1(j, m)$$

In some embodiments the difference between feature values is calculated between various points along the speech signal. By way of a non-limiting example, heart beat potentially changes the feature values in a pattern that can be used to locate the RR-pulses.

By way of a non-limiting example: the heart beat potentially changes spectral cross coherence at the pitch and formant frequencies so that the time difference between two parts of the speech where coherence is minimal can be used to estimate RR interval.

In some embodiments, some features are averaged on the whole utterance.

In some embodiments, some statistical values of some features are calculated over the whole utterance. Optionally, for some voice features the unvoiced parts are used. Alternatively or additionally, for some voice features only voiced parts are used (for example, by choosing features such as formants and/or pitch). In some embodiments, small gaps (e.g. less than about 20% of a BPM length, less than about 15% of a BPM length, and/or less than about 10% of a BPM length, and/or less than about 5% of a BPM length) between continuous segments are neglected, for example, omitted from the feature sequence. Potentially, small gaps are not significant since the heart pulse effect on the blood pressure is estimated to be longer than the gaps. Alternatively or additionally, a gap between segments is reconstructed and/or extrapolated, for example, when identifying a slope at the end of the segment and a complementary slope on the next segment, an occurrence of a voice feature and/or cardiac feature can be extrapolated.

Optionally, a voice feature is normalized at 512, as shown for example in FIG. 5B-5C. A potential advantage of normalization is minimizing analysis of frames potentially having less information, such as transition frames. In some embodiments, frames are removed at 514 according to predetermined rules, the rules optionally pertaining to the probability of the frame to indicate cardiac information.

In some embodiments, the calculated voice features are combined into an acoustic vector to represent each frame at 516. Optionally, the acoustic vector contains several voice features (such as MFCC, LPC, wavelet, pitch etc., generically termed acoustic parameters), and/or voice feature statistics and/or derivatives (named "DIFF" in equation below) that are combined into a single vector, for example:

$$Acoustic_{VEC(m)} = \begin{cases} Acoustic\_parameter(1, m) \\ Acoustic\_parameter(2, m) \\ \ldots \\ Acoustic\_parameter(12, m) \\ Diff1(1, m) \\ Diff1(2, m) \\ \ldots \\ Diff1(12, m) \\ Diff2(1, m) \\ Diff2(2, m) \\ \ldots \\ Diff2(12, m) \\ \ldots \end{cases}$$

where the acoustic vector contains a series of acoustic parameters and their derivatives—marked as Diff1—for first derivative and Diff2 for the second derivative.

By way of a non-limiting example the Acoustic vector of frame "m" can be:

Acoustic_parameter(1 . . . 12,m)=LPC (1 . . . 12,m)
Acoustic_parameter(13 . . . 26,m)=MFCC (1 . . . 13,m)
Acoustic_parameter(27,m)=Pitch(m)
Acoustic_parameter(28,m)=RMS_ENERGY(m)
Acoustic_parameter(29 . . . TBD, m)=$SPECTRAL\_COHERENCE\_PITCH$(m,t)
  Remark: coherence value to adjacent frames in pitch frequencies|Acoustic_parameter(29 . . . TBD, m)=$SPECTRAL\_COHERENCE\_FORMANTS$(m,t)
  Remark: coherence value to adjacent frames in formant frequencies|Acoustic_parameter(TBD . . . TBD,m)= WAVELET_TRANSFORM(m)
Diff1(1 . . . 12,m)=first derivative of LPC (1 . . . 12,m)
Diff2(1 . . . 13,m)=second derivative of MFCC (1 . . . 13,m)

Optionally, the voice feature vector per frame is subjected to subsequent analysis, for example, deriving heart rate information. Alternatively or additionally, subsequent analysis includes distribution and/or periodicity calculations. Alternatively or additionally, the voice sample, optionally after filtering and/or classification, is used for subsequent analysis rather than the voice features or the acoustic vectors.

Reference is now made to FIG. 5B, exemplifying normalization of a voice sample, in accordance with some embodiments of the invention. Since the acoustic vectors contain information on cardiac condition and speech phonetics, it is potentially beneficial to remove (e.g. normalize) the speech phonetic information in order to emphasize the cardiac information. FIGS. 5B and 5C exemplify a method on normalizing "natural" changes in the speech (due to phonetic information).

In some embodiments, the normalization algorithm estimates the "natural" changes in the speech using polynomial regression curve fitting method, for example as described below.

In some embodiments, once voice feature vectors are obtained, acoustic vector coefficients are derived at 542. In some embodiments, the coefficients are subjected to polynomial approximation at 544. The polynomial function estimates the time fluctuation of the features—i.e. parameter as the function of the time. The fluctuation function representation by a polynomial is a "smooth" function that accounts only "natural" long changes and not short changes originating in a heart pulse effect.

In some embodiments, a slope change is calculated at 546. Optionally, the feature vectors (per frame) are band pass filtered at 548 based on their slope value and its position with respect to a predetermined threshold or range. In some embodiments, the polynomial estimation reflects a "natural" fluctuation of speech, that is, changes in speech due to phonation, and is optionally subtracted from the voice feature. For example:

Let x(i) be the voice feature vector coefficient for a segment of speech i=1 . . . N, which are sampled at time t(i) i=1 . . . N.

The Frame sampling interval is: Ts which is equal to 1/Fr Where Fr is the frame rate M-order polynomial is used for estimation, resulting in estimation error E(i):

$$x(i) = \sum_{k=0}^{m} a_k * t(i) + \varepsilon(i)$$

This can be written as $$\begin{bmatrix} x(1) \\ \ldots \\ x(N) \end{bmatrix} = \begin{bmatrix} t(1) & \ldots & t(1) \\ \ldots & \ldots & \ldots \\ t(N) & \ldots & t(N) \end{bmatrix} * \begin{bmatrix} a_0 \\ \ldots \\ a_m \end{bmatrix} + \begin{bmatrix} \varepsilon(1) \\ \ldots \\ \varepsilon(N) \end{bmatrix}$$

OR $$\vec{X} = T * \vec{a} + \vec{\varepsilon}$$

The polynomial coefficients can be estimated using least square estimation:

$$\vec{a} = (T^T * T)^{-1} * T^T * \vec{X}$$

The polynomial estimation reflects the "natural" fluctuation of the speech and is subtracted from the voice feature:

$$\tilde{x}(i) = x(i) - \sum_{k=0}^{m} a_k * t(i)$$

FIG. 5C, illustrates an exemplary normalization process, where the black line shows the voice feature value over time (top graph). The blue (dotted) line is the normalization—correction function, using 3-order polynomial. The top graph shows the original signal and the correction function, and the bottom graph shows the signal after the normalization. In some embodiments, the parts of the speech which are between constant sound periods are removed from the analysis.

It is estimated that during speech the voice features reflect both vocal information and heart information. Since the heart pulse effect on the speech signal is estimated to be delicate, in some embodiments a normalization algorithm is used to reduce natural changes, optionally during constant sound periods, in the voice features that are "natural".

Such a sound normalization process, optionally takes place in some embodiments of the invention. In some embodiments, a normalization algorithm reduces the transition parts and/or "smooths" the single sound parts in order to take more data into account for analysis. FIGS. 8A-8B show another example of using the pitch parameter.

Exemplary High Level Overview of Distribution Analysis

Reference is now made to FIG. 6A, is a general high level overview illustrating estimation of a cardiac condition from a voice sample by distribution analysis, in accordance with some embodiments of the invention.

In some embodiments, a voice is sampled at 602 and analyzed to extract at least one voice feature at 604. In some embodiments, the distribution over time of the voice feature is calculated at 606, and used to determine a cardiac condition at 608. Optionally, distribution calculations include calculating the variability of the extracted voice feature. It is estimated that blood flow affected by the heart pulse, influences the voice, and when an arrhythmia occurs, the influence is estimated to be irregular. It is therefore estimated, that in pathologic heart conditions, the distribution of the voice feature values would change.

Exemplary Detailed Flowchart of Exemplary Distribution Analysis

Reference is now made to FIG. 6B, showing a flowchart illustrating a detailed process for feature distribution analysis showing the pitch as an example for voice feature, in accordance with some embodiments of the invention.

In some embodiments, the voice feature selected is the pitch. A potential advantage of calculating the pitch is that it is one of the main voice features that manifest the heart pulse due to changes in mass of the vocal folds resulting from the heart beat. It is estimated that the pitch parameter has only relatively minor "natural" changes during the constant speech signal. As used herein, natural changes refer to changes that occur in voice features during voice transitions, e.g. between and in between sounds and/or phonemes, including for example breathing. The natural changes are not related to the heart beat and in some embodiments are minimized by normalization algorithm, as exemplified in FIG. 5B-5C. It is a potential advantage to use the pitch for voice analysis over other vocal features which are more prone to non-cardiac alterations. Other potential benefits of the pitch feature are that it is typically found in more than 40% of the time of the voice signal, and that it is likely to sustain stable values over different sounds of spontaneous speech.

In some embodiments, a voice is sampled at 612 and voiced segments are classified at 614. In some embodiments, classified voiced segments are concatenated at 616 to receive continuous data. In some embodiments, the pitch is extracted from the concatenated voiced segments at 618.

Optionally, natural fluctuations of the pitch, e.g. resulting from the vocal organs movement and/or operation rather than from the blood flow, are removed, for example, using processes as described and illustrated in FIGS. 5B-5C. In some embodiments, after segments are removed, remaining voiced segments are concatenated at 622 and optionally smoothed at 624. In some embodiments, smoothing includes smoothing the transition at fusion points between different segments.

In some embodiments, the pitch distribution is calculated at 626. For example, distribution calculation includes a statistical variability of the pitch values and/or any other statistical information obtained from mathematical operation on the voice features, for example, such as standard deviation, and/or high order moments, and/or skew deviation, and/or average, etc.

In some embodiments, the distribution value is compared to a predetermined threshold at 628 to determine a healthy condition at 630 or a pathologic condition at 632. For example, a high distribution is suggestive of irregular effects, therefore a distribution value which is above the threshold, might be considered as a pathologic condition. In some embodiments, the value of the distribution could be its shape.

An Exemplary Single-Speaker Method

In some embodiments variations in pulse rhythm are optionally detected by measuring a variation between a single patient's voice at one time compared to the same patient's voice at another time.

In some embodiments a patient is requested to voice the same sound(s) and/or the same phoneme(s) at different times, especially at one time when the patient's heart is arrhythmic and at a time when the patient's heartbeat is regular.

Changes in heart rhythm are optionally detected by analysis of the voice signal.

In some embodiments the analysis is of recordings of tones, and/or phonemes, and/or words, and/or sayings of a patient at different times and optionally comparison to live voicing of the same tones, and/or phonemes, and/or words, and/or sayings of the patient.

In some embodiments same phonemes of patients with chronic diseases, such as chronic heart disease, are optionally analyzed when their pulse is regular, and acoustic features of the analysis are optionally saved to compare to acoustic features of live voicing or other recordings of the same patients at other times.

The acoustic features optionally include one or more of:

Spectrum based parameters, such as spectral distribution of energy, peaks, peak energy, peak band width, spectral slope. etc.

Mel Frequency Cepstral Coefficients (MFCC);

LPC coefficients;

Glottal pulse parameters (glottal pulse rise time, glottal pulse fall time, glottal pulse open period, glottal pulse close period, glottal pulse frequency, glottal pulse peak location, glottal pulse spectrum, jitter of glottal pulse periods, jitter of glottal pulse amplitudes and more);

pitch parameter(s);

partial correlation coefficients, abbreviated PARCOR, which are a measure of correlation between the parameters, yet not necessarily between all the parameters; and wavelet analysis parameters.

In some embodiments calculating the acoustic features includes one or more of:

centroids of feature space, optionally using K-MEANS clustering analysis;

a histogram and\or Probability Density Function (PDF) of variations of features. In some embodiments one or more acoustic feature(s) are calculated for an utterance, and a distribution of the acoustic feature(s) (such as minimal & maximal values, standard deviation, distribution shape etc.) is optionally used as an indication of heart rate pathology in speech;

modulation parameters—after calculating acoustic parameter(s) for the utterance, a spectrum of the parameter(s) is optionally calculated using parametric and\or non-parametric methods. The parameters from the spectrum that are used are one or more of:

peaks location(s), peak band-width(s), peak energy, spectral slope(s) etc.

sub-space calculation of feature space using a Support Vector Machine (SVM); and other clustering methods from a machine learning approach.

The above calculations of acoustic features optionally produce distributions of different character for speech of a healthy person and speech of a person with a pathological cardiac condition.

In some embodiments an initial learning/training stage a statistical model of an acoustic signal is optionally calculated, optionally including distributions of lengths of RR intervals for a healthy regular cardiac rhythm and for a pathological cardiac rhythm, and a threshold is determined for differentiating between a healthy value and a pathological value of one or more of the statistical measures of the acoustic features.

In some embodiments a statistical cardiac condition classifier is optionally trained by:

collecting voice recordings of cardiac-healthy and cardiac-unhealthy speakers;

calculating one or more acoustic features as mentioned herein for the recordings;

training a statistical classifier using the above-mentioned techniques and/or additional machine learning techniques.

In some embodiments, the voice recordings are collected for different people, optionally even a large number of healthy and/or a large number of unhealthy speakers.

In some embodiments, the voice recordings are collected for a single person, for example at a time when the person is known to be healthy.

In some embodiments when a change in the healthy speech is detected, the person is optionally classified as potentially having an unhealthy cardiac condition.

In some embodiments, the voice recordings are optionally also collected for a single person, for example at a time when the person is known to be unhealthy, optionally with a known cardiac condition.

In some embodiments when the speech is detected to be similar to the unhealthy recording(s), the person is optionally classified as potentially having an unhealthy cardiac condition.

In some embodiments an initial learning/training stage a statistical model of an acoustic signal is optionally calculated, optionally including distributions of lengths of RR intervals for a healthy regular cardiac rhythm and for a pathological cardiac rhythm, and a threshold is determined for differentiating between a healthy value and a pathological value of one or more of the statistical measures of the acoustic features.

Reference is now made to FIG. 6C, which is a simplified flow chart illustration of a method for learning to diagnose cardiac conditions in accordance with some embodiments of the invention.

FIG. 6C shows a method including:

Sampling voice (640);

Extracting voice features (642);

Optionally combining voice features from several utterances (644);

Performing cluster analysis (646);

Optionally producing a codebook (648).

In some embodiments the sampling is optionally performed by digitizing voice in a range of frequencies including 6 Hz to 100 KHz.

In some embodiments the sampling of the voice is optionally done for speech known to be spoken by a cardiac-healthy speaker or speakers and/or at least at a period when the speaker(s) have a non-pathological heart rhythm.

In some embodiments the sampling of the voice optionally includes speech known to be spoken by a speaker or speakers having a pathological heart rhythm, optionally recognized as examples of speech of a speaker or speakers having a pathological heart rhythm.

In some embodiments the optional combining of voice features from several utterances is optionally performed for utterances of healthy speaker(s) and/or when the speaker(s) have a non-pathological heart rhythm.

In some embodiments the optional combining of voice features from several utterances is optionally performed separately for utterances of healthy speaker(s) and/or when the speaker(s) have a non-pathological heart rhythm and separately for speech of a speaker or speakers having a pathological heart rhythm.

In some embodiments the cluster analysis is optionally performed for utterances of healthy speaker(s) and/or when the speaker(s) have a non-pathological heart rhythm.

In some embodiments the cluster analysis is optionally performed separately for utterances of healthy speaker(s) and/or when the speaker(s) have a non-pathological heart rhythm and separately for speech of a speaker or speakers having a pathological heart rhythm.

In some embodiments the codebook is optionally of healthy speaker(s) and/or representative of when the speaker(s) have a non-pathological heart rhythm.

In some embodiments the codebook optionally includes classifications for speech of healthy speaker(s) and speech of a speaker or speakers having a pathological heart rhythm.

In some embodiments the cluster analysis is optionally performed by K-means analysis.

Reference is now made to FIG. 6D, which is a simplified flow chart illustration of a method for classifying cardiac condition in accordance with some embodiments of the invention.

FIG. 6D shows a method including:

Sampling voice (650);

Extracting voice features (652);

Optionally selecting a voice feature (654);

Calculating distance of voice feature from one or more codebook value(s) (656);

Comparing distance to threshold (658); and

Classifying cardiac condition (659).

In some embodiments the sampling is optionally performed by digitizing voice in a range of frequencies including 6 Hz to 100 KHz.

In some embodiments the classifying cardiac condition is optionally determined based on the distance being greater than a threshold value from one or more codebook values of a healthy cardiac condition.

In some embodiments the classifying cardiac condition is optionally determined based on the distance being smaller than a threshold value from one or more codebook values of a healthy cardiac condition.

In some embodiments the classifying cardiac condition is optionally determined based on the distance being greater than a threshold value from one or more codebook values of a diseased cardiac condition.

In some embodiments the classifying cardiac condition is optionally determined based on the distance being smaller than a threshold value from one or more codebook values of a diseased cardiac condition.

Example of Concatenated Voiced Segments Reference is now made to FIGS. 7A-7B, showing an example for a voice sample shown in FIG. 7A, which has been classified to remove voice segments and then remaining segments have been concatenated in FIG. 7B, in accordance with some embodiments of the invention.

In the exemplified classification, the voice sample of FIG. 7A has been classified for voiced 702 and unvoiced segments 704. The graph shown in FIG. 7B shows that remaining voiced segments 702 have been concatenated. It should be noted that concatenation of segments is conducted only in some embodiments of the invention, and is typically provided when the time sequence of the voice feature is less significant, but rather the behavior at each point, and/or all points as a whole, is analyzed.

Example of Data Smoothing

Reference is now made to FIGS. 8A-8B, showing an example for pitch data extracted from a voice sample which has been smoothed, wherein FIGS. 8A and 8B illustrates smoothing of "natural" fluctuations of the voice. The red line indicates the voice feature over time, in this case the pitch over time, and the blue line indicates the correction function.

FIG. 8B shows the pitch signal after the normalization. Typically, after removing the "natural" changes from the voice feature, higher accuracy of extracting heart information is obtained.

Example of pitch extraction

Reference is now made to FIGS. 9A-9B, showing an example for pitch data extracted from a voice sample, after being filtered and smoothed, in accordance with some embodiments of the invention, wherein FIG. 9A shows an example for concatenated voiced segments, and FIG. 9B shows an example for pitch extraction of the concatenated voice segments if FIG. 9A, in accordance with some embodiments of the invention. The dotted parts are the "fusion" points between separate segments that are omitted from the analysis since the "natural" changes are significant and might mask the heart contributed changes.

Exemplary Determination of Probability for Heart Rate Pathology Using Voice Features Statistical Analysis Method In some embodiments, the "healthy" voice feature (and\or its statistics and\or mathematical operation) distribution is calculated from a training set of healthy speakers (i.e. a speaker independent model). Alternatively or additionally, the "healthy" voice feature distribution (and\or its statistics and\or mathematical operation) is calculated from the tested speaker during known healthy, e.g. sufficiently periodic, states (i.e. a speaker dependent model).

Reference is now made to FIGS. 10A-10D, showing an example of histograms of the distribution of the normalized standard deviation values of a pitch of speech recorded during AF (FIGS. 10B and 10D) and during speech of healthy people (FIGS. 10A and 10C). exemplifying the determination of probability for heart rate pathology using voice features distribution analysis, in accordance with some embodiments of the invention.

Figure 10A:
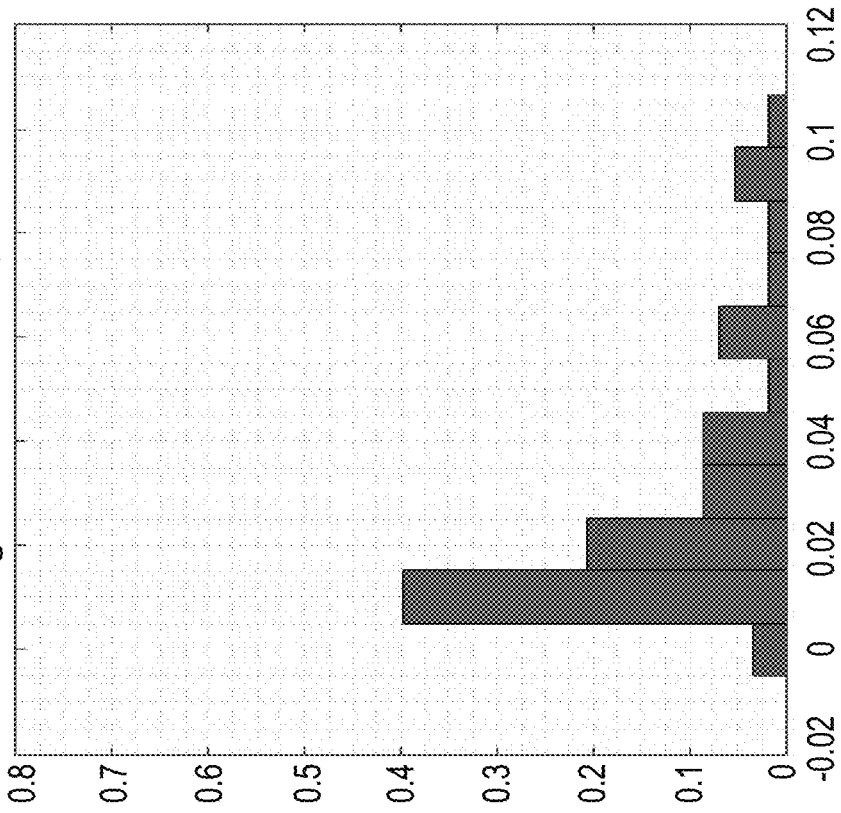
Figure 10B:
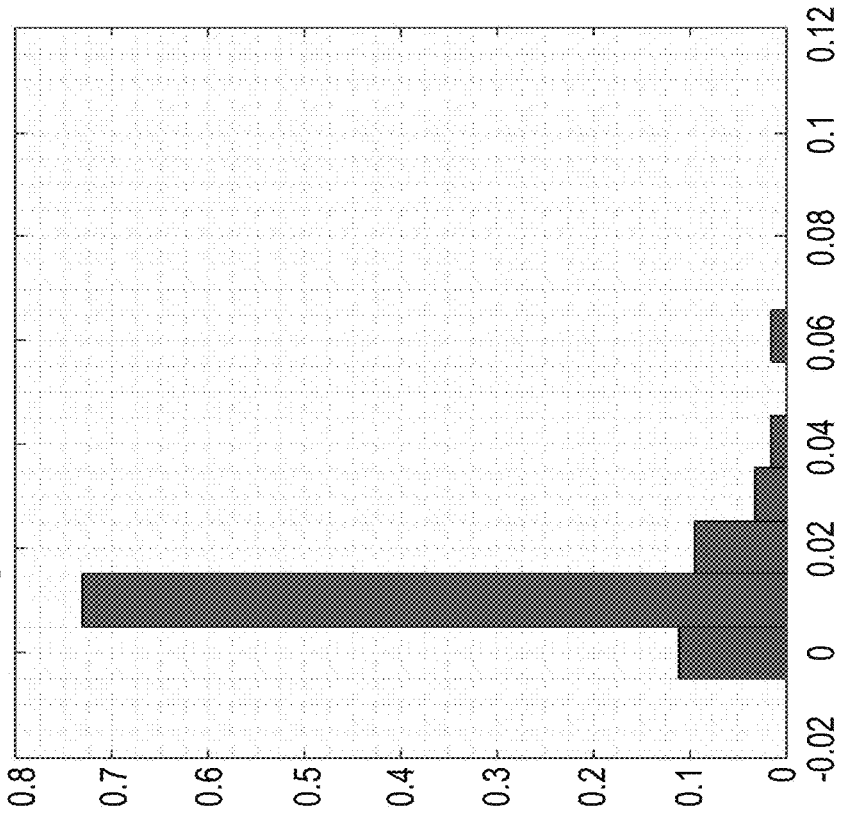
Figure 10C:
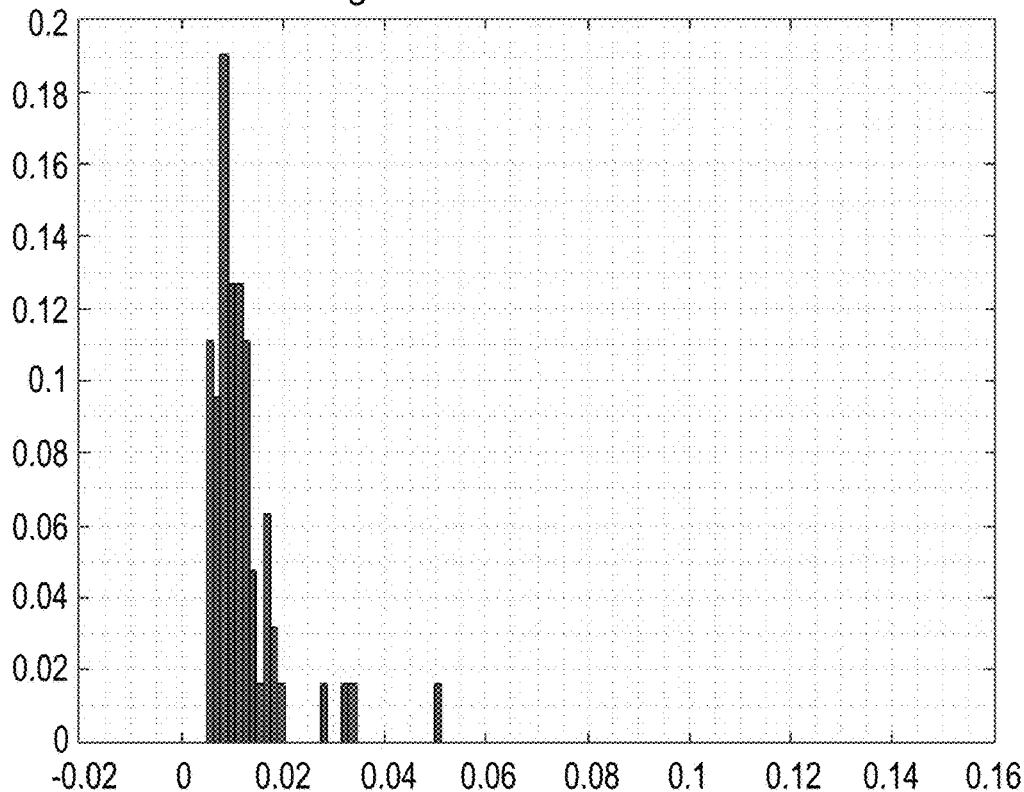
Figure 10D:
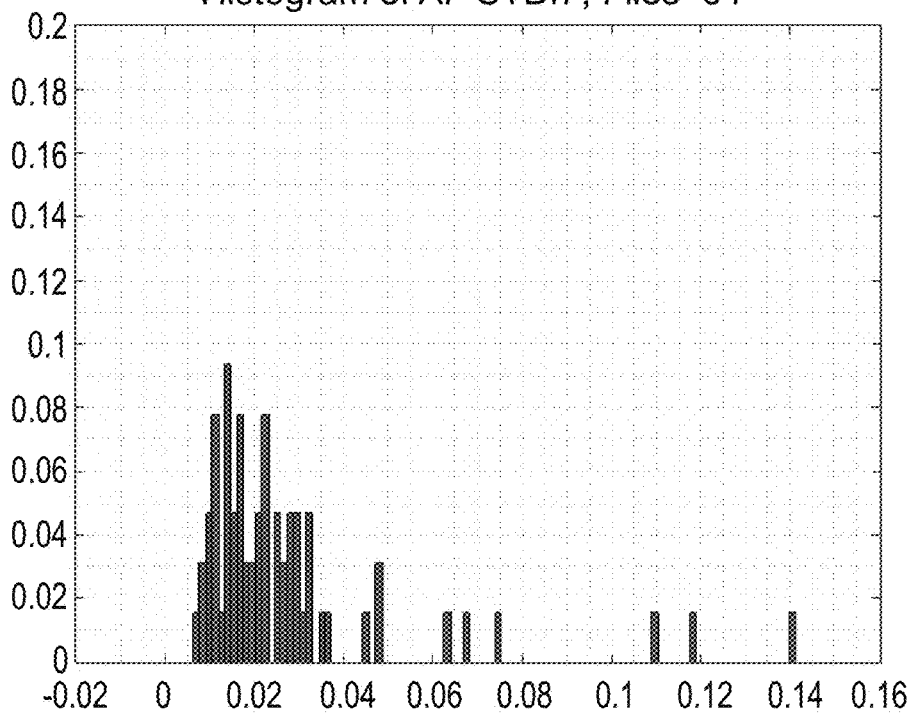

Exemplified is the calculated normalized standard deviation of a pitch over a training set of speech deriving from healthy subjects in FIG. 10A (and FIG. 10C—that show identical distribution of 10A with higher resolution) and AF diagnosed subjects in FIG. 10B (and FIG. 10D—that show identical distribution of 10B with higher resolution). In this example, the pitch parameter was chosen due to its relatively high stability over different sounds, and it's presence over more than 40% of the natural speech period.

In some embodiments, a threshold of the normalized standard deviation of the pitch is used to detect AF. Alternatively or additionally, a trained statistical distribution is formed for healthy subjects and a trained statistical distribution is formed for non-healthy subjects, and optionally the current distribution is statistically matched to each trained distribution. Optionally, diagnosis is estimated based on the higher statistical probability to match.

For example, for pitch values calculated for the $i^{th}$ frames of speech, i=1 . . . N:

The Standard deviation is calculated overall several parts of the speech signal. The parts duration is chosen to be minimal (in order to detect short pathology episodes) according to the variability of the acoustic parameter that is used.

$$STDEV = \sqrt{\frac{1}{N}\sum_{i=1}^{N}(\text{Pitch}(i) - \mu)^2},$$

$$\mu = \frac{1}{N}\sum_{i=1}^{N}\text{Pitch}(i)$$

For this example it can be seen that 85% of the STD<0.02 for regular pulse, and for 60% of the AF-recordings STD>0.02.

Exemplary Heart Rate Extraction

In some calculations, in some embodiments, the heart rate of the analyzed subject is used. Following is an exemplary heart beat frequency extraction from the voice sample of the subject, in accordance with some embodiments of the invention.

In some embodiments, the heart rate is calculated based on spectral analysis (for example as shown in FIG. 14B, block 1416), for example discrete Fourier transform on the voice features. In the following example, $\vec{V}$ denotes the matrix of p voice features of T continuous speech fragments (e.g. fragments of the speech frames without noise and/or silence):

$$\vec{V} = \begin{bmatrix} v(t, 1) & v(t+1, 1) & \dots & v(T, 1) \\ \dots & \dots & \dots & \dots \\ v(t, p) & v(t+1p) & \dots & v(T, p) \end{bmatrix}$$

The matrix may include various voice features at specific times, for example:

V(t,1)—can be pitch value at time t.
V(t,2)—can be pitch derivative at time t
V(t,3)—can be MFCC coefficients at time t A discrete Fourier transform may be calculated for each coefficient (raw of the matrix) by using:

$$\vec{V}(w) = \begin{bmatrix} V(w, 1) \\ \dots \\ V(w, p) \end{bmatrix} = \begin{Vmatrix} \sum_{n=0}^{N-1} v(t, 1) * e^{-i\omega t/N} \\ \dots \\ \dots \\ \sum_{n=0}^{N-1} v(t, p) * e^{-i\omega t/N} \end{Vmatrix}$$

Each raw is equal to the absolute value of the Fourier transform of one voice feature parameter. The heart rate will be shown in the frequency domain by a peak in the frequency of the heart rate. Optionally, BPM (Beats Per Minute—of heart rate) is calculated for several voice features, followed by averaging and using the average value, or a value after a majority vote selection of the most common value in all calculated feature coefficients. In some embodiments, non-reasonable values are filtered (for example, below about 30 bmp and above about 300 bpm). Alternatively or additionally, for highly irregular heart-beat the spectral energy is not band limited.

Exemplary Pulse Interval Extraction

Reference is now made to FIG. 11A illustrating a general flow chart for calculating pulse interval, in accordance with some embodiments of the invention.

In some embodiments, a voice sample 1102 is used to identify at least two heart pulses at 1104. In some embodiments, the time interval between the pulse occurrences is calculated at 1106. In some embodiments, cardiac condition is estimated at 1108 based on the extracted time interval.

Optionally, the pulses are consecutive to each other. Alternatively, if the time interval is calculated to be short enough, non-consecutive pulses are sufficient to determine a cardiac condition.

In some embodiments, analysis is executed on each frame separately. Alternatively or additionally, analysis is executed on a composed sequence of a plurality of frames. In some embodiments, a sequence of identified pulses is compiled, optionally maintaining the time sequence of the pulses, even if they occur at different frames. In some embodiments, the time intervals between the identified pulses are compared to a reference and/or a threshold in order to determine the cardiac condition.

Exemplary Detailed Pulse Interval Extraction

Reference is now made to FIG. 11B, showing a flowchart exemplifying detailed pulse interval extraction, in accordance with some embodiments of the invention.

In some embodiments, a voice sample 1112 is classified to extract voiced segments at 1114. In some embodiments, voiced segments include length of about 0.5 sec to about 3 sec. In some embodiments, the voiced segments are used for identifying heart pulses at 1116, such as for example R pulses as further detailed and described in FIGS. 11C and 11D. In some embodiments, the time interval between the identified pulses is calculated at 1118.

In some embodiments, at least two pulses are identified in a single voice segment. Alternatively, at least three pulses, or at least four, or at least five, or at least six, or at least seven, or at least eight pulses are identified per voice segment. In some embodiments, this segment includes non-continuous parts). In some embodiments, only pulses which are consecutive to each other are taken into consideration. Alternatively, only time intervals which are equal to, or smaller than, the heart rate of the subject, are taken into consideration.

Optionally, short sequences of time interval between identified pulses are matched to a reference at 1120, and the probability to match the reference is calculated. In some embodiments, a reference is time intervals of pulses identified in the same subject, but during a healthy condition. Alternatively or additionally, a reference contains time intervals of pulses known to be characteristic of a healthy, and/or a pathologic condition. Alternatively or additionally, a reference includes a database of a plurality of time interval sequences derived from other healthy and/or pathologic voice samples. In some embodiments, the reference patterns are obtained in a preliminary stage using databases of both healthy and pathological speech samples.

In some embodiments, the probability to match value is compared to a threshold at 1122, wherein, for example when matching to a pathologic sequence, a value below the threshold would lead to healthy condition determination at 1130 and a value above the threshold would lead to pathologic condition determination at 1132. In some embodiments, the threshold is a predetermined fixed value. Alternatively, the threshold is a variable which is dynamically determined based on multiple sources of data, such as for example by using machine learning. For example, if in another test, a high probability to determine an arrhythmia is detected, the threshold for determining an arrhythmia based on the time intervals at 1122 could be lower.

Exemplary R Pulse Location Identification

Reference is now made to FIG. 11C, showing a flowchart exemplifying identification of R pulses location on a time axis.

Therefore, in some embodiments, after a classification of the speech frames (shown in FIGS. 5A-5C), and optionally omitting silence, and/or frames with no information and/or transition frames.

In some embodiments, for a continuous segment of speech, acoustic vectors representing frames of speech are obtained. In some embodiments, a distance is calculated from each frame acoustic vector to all other frames in the segment. Potentially, the distances hold information regarding the changes in the speech signal that is caused by non-continuous\unknown small changes in speech organ tissues that reflect tissue flexibility, and/or natural changes due to changes in muscle tension and/or changes in blood vessels mass and volume. Distance between consecutive frames is expected to be minor, and larger for more separated frames.

In some embodiments, at 1150 for each frame (t) a distance is calculated to previous (backward) frames and proceeding (forward) frames, optionally for all the speech frames.

For example, the distance function between two acoustic vectors can be calculated by:

$$Acoustic_{VEC(m)} = \begin{Bmatrix} Acoustic\_parameter(1, m) \\ Acoustic\_parameter(2, m) \\ \ldots \\ Acoustic\_parameter(12, m) \\ \mathit{Diff}1(1, m) \\ \mathit{Diff}1(2, m) \\ \ldots \\ \mathit{Diff}1(12, m) \\ \mathit{Diff}2(1, m) \\ \mathit{Diff}2(2, m) \\ \ldots \\ \mathit{Diff}2(12. m) \\ .. \end{Bmatrix} = \begin{Bmatrix} ap(1, m) \\ ap(2, m) \\ ap(3, m) \\ \vdots \\ .. \\ ap(36, m) \end{Bmatrix} =$$

{where the acoustic vector contains a series of acoustic parameters and their derivatives—marked as Diff1—for first derivative and Diff2 for the second derivative}

$$D(t1, t2) = D(Acoustic\_vec(t1), Acoustic\_vec(t2)) =$$
$$= \frac{1}{12} \sum_{p=1}^{12} [(ap(p, t1) - ap(p, t2)) * W(p)]^{\wedge}2$$

Where W(p) is weighing coefficients serving for normalization and scaling.

In some embodiments, at 1152 local minima in the forward distance series and/or in the backward distance series are identified.

Find local minima in a distance measured from point (t=t1) in a forward direction (t>t1):

$$t2 = \text{ARGMIN}_j\{D(t,j)\}, j > t1$$

and in a backwards direction (t<t1)

$$t3 = \text{ARGMIN}_j\{D(t,k)\}, k < t1$$

In some embodiments, the sum of distances to the local minima is used to estimate RR interval at 1154, based on frame t:

$$R\widetilde{R_{inteval}^t} = \alpha(t3+t2)$$

Where α is a constant.

Reference is now made to FIG. 11D, which shows an exemplary graph of RR interval estimation in accordance with some embodiments of the invention.

FIG. 11D includes a graph 1100 which shows D(t) in a Y-axis 1106, as a function of time t along an X-axis 1107.

The graph 1100 shows D(t1) 1101 at a time t1, a first minimum of D(t) 1102 at a time t2 prior to t1, and a second minimum of D(t) 1103 at a time t3 following t1.

FIG. 11D shows the RR interval being estimated based on detecting the minima 1102 1103, as RR_interval=(t3-t2).

In some embodiments, several RR intervals are estimated.

In some embodiments, only some estimated RR intervals are used, according to one or more criteria such as:

(1) The shape of local minima ("deep" or "flat")

(2) The RR interval validity. In some embodiments the RR interval is optionally only used if suitable for estimating BPM values within reason. such as, by way of a non-limiting example, larger than 45 BPM and smaller than 250 BPM)

(3) Choose some RR intervals that are most probable. In some embodiments RR interval lengths are optionally calculated, and a distribution of the RR interval lengths is optionally calculated. Optionally, RR intervals are chosen which fall within a specific threshold surrounding an average RR interval length, such as within approximately +/−5%, 10%, 20%, 33%, 50% of the average. Optionally, RR intervals are chosen which fall within a specific range of RR interval lengths which correspond to heart rates surrounding an average heart rate, such as within approximately +/−5%, 10%, 20%, 33%, 50% of the average. In some embodiments such an analysis is optionally made after analyzing a segment of speech, optionally an entire conversation, and obtaining a list of possible RR intervals.

In some embodiments analysis of the sequence is made, looking for most probable patterns. For a regular heart rate—similar RR intervals will be found. For irregular heart rate none or few similar RR intervals will be found.

(4) Use other criteria to estimate probability of natural speech changes which are not "heart pulse" related.

In some embodiments, when local minima is not sharp (e.g. longer periods) the estimated distance is removed from subsequent analysis and the next minima is considered. In some embodiments, one RR interval per frame segment is calculated, typically for short frame segments. Alternatively, a plurality of RR intervals is calculated, typically for longer segments.

In some embodiments, RR interval is estimated for all frames {t=0, 1, . . . T}. Optionally, the RR intervals derived from an entire speech sample are averaged over all features that are calculated at 1156, and optionally an overall estimate of RR interval of the whole speech sample is derived at 1158.

Example of RR Interval Identification in a Voice Sample

Reference is now made to FIG. 12A, presenting an example of the frame to frame distance for MFCC type voice features in a constant vowel, wherein the top graph shows frame to frame distance pattern (of MFCC acoustic features calculated in each frame) and the bottom graph shows an ECG graph as a reference, in accordance with some embodiments of the invention. The arrows shown in FIG. 12A indicate two frames: frame (t) and frame (i). For a given frame {t} the frame to frame distance to frame {i} will have periodic nature where a local minima that is likely to appear every RR interval, that is D(t,i) will have local minima at points that the time distance between them is equal to the RR intervals. The arrows from the top graph to the bottom graph show that the local minima of the frame-to-frame distance (top graph) appear in locations that are periodically similar to the RR intervals (bottom graphs).

Example of RR Interval Identification in a Voice Sample Using Coherence

In some embodiments the above method is optionally used, using a coherence value as a measure of fluctuations of speech.

Using the above method and definitions:

$$D(t1, t2) = D(Acoustic\_vec(t1), Acoustic\_vec(t2)) =$$
$$= \frac{1}{12} \sum_{p=1}^{12} [(ap(p, t1) - ap(p, t2)) * W(p)]^{\wedge}2$$

For coherence:

$$D(t1,t2) = Coherence(Speech(t1:t1+tw), Speech(t2:t2+tw))$$

In some embodiments spectral cross coherence is calculated between two speech frames, one starting at a time t1 and the other starting at a time t2.

$$X(n) = speech(t1, t1+1, t1+2, \ldots t1+Tw))$$

$$Y(n) = speech(t2, t2+1, t2+2, \ldots t2+Tw)$$

Where Tw=frame size of analysis $$C_{xy}(f) = \frac{|G_{xy}(f)|^2}{G_{xx}(f) * G_{yy}(f)}$$

$$G_{xy}(f) = \frac{1}{2\pi} \sum R_{xy}(n) * e^{-i2\pi fn}$$

$$D(t1, t2) = \sum_{f=pitch\ or\ f=formants} C_{xy}(f)$$

Reference is now made to FIG. 12B, which shows an exemplary graph of coherence calculation in accordance with some embodiments of the invention.

FIG. 12B includes a graph 1230 which a coherence value in a Y-axis 1236, as a function of time t in milliseconds along an X-axis 1237.

The graph 1230 shows coherence in pitch frequency from a point at time t1 1231 reaching a minimal value, corresponding to a maximal shift in frequency, at a time t2 1232 of ~820 msec distance. The time t2 is close to a patient's pulse period of 855 msec.

Example of RR Interval Data

Reference is now made to FIG. 13, presenting an example for the change in sensitivity versus the specificity of heart condition determination with increasing occurrences of consecutive pulses, in accordance with some embodiments of the invention.

The graph shows the percentage of people correctly diagnosed as having a pathology on the Y axis as P(D), versus the probability of people incorrectly diagnosed as having a pathology on the X axis as P(FA) (shown in 1 minus the probability). The graph shown exemplifies how the sensitivity increases when the number of consecutive pulses increases. It also shows that when the number of consecutive pulses increases both specificity and sensitivity increase as well.

It should be noted that the calculation is based on the algorithm shown below under the section of overall Arrhythmia probability integration, which includes a method of AF assessment from only a few RR pulses.

Exemplary Periodicity Determination Overview

Reference is now made to FIG. 14A, presenting a flow chart illustrating a process for determining periodicity at the heart rate used for determining a cardiac condition, in accordance with some embodiments of the invention. Assuming heart rate is periodic, it is expected that the changes in blood vessels mass and/or volume are semi-periodic (or periodic for normal sinus heart rate). Therefore, timing of cardiac activity is potentially detected by finding periodic changes in the frame to frame distance pattern.

In some embodiments, a voice is sampled at 1402 and at least one voice feature is extracted at 1404. In some embodiments, periodicity of the at least one voice feature is calculated at 1406, for example, using spectral analysis and/or autocorrelation. In some embodiments, cardiac condition is estimated at 1408 based on the periodicity of the voice feature. This means that regular pulse rate is estimated to create "narrow" energy in the spectral\autocorrelation domain (of a voice feature over time) since most energy is estimated to be concentrated in the heart rate frequency. Irregular pulse (mostly AF) will probably not have concentrated energy in one frequency and the spectrum\autocorrelation values near the average heart rate will probably be less concentrated.

Exemplary Detailed Periodicity Determination of the Voice Features

Reference is now made to FIG. 14B, presenting a flow chart for determination of timing of cardiac activity based on timing of its effects over the voice sample, in accordance with some embodiments of the invention.

In some embodiments, voice is sampled at 1412 and at least one voice feature is extracted at 1414. In some embodiments, the voice sample is used to extract the heart rate of the sampled subject. Alternatively or additionally, heart rate is measured by a heart rate monitor. In some embodiments, autocorrelation of the voice feature is calculated at 1418 at a plurality of frequencies which include the heart rate frequency. The autocorrelation is optionally characterized at a predetermined range around the frequency of the heart rate. In some embodiments, characterization is provided by identifying a peak shape parameter and determining its value at 1420. For example, a peak shape parameter could be a band width of the peak and/or its amplitude. In some embodiments, the parameter value is compared to a threshold at 1422 to determine a healthy condition at 1430 or a pathologic condition at 1432.

Example for Glottal Pulse Analysis of Voice Features

Glottal pulse analysis is a technique to calculate a pulse resulting from movement of glottal cords potentially without effects of other speech organs such as, for example, mouth, tongue, lips and/or oral/nasal cavities.

Reference is now made to FIG. 14C, which is a simplified illustration of a glottal wave, in accordance with some embodiments of the invention.

FIG. 14C shows illustrations 1440 of cross sections 1441 1442 1443 1444 1445 of a throat and glottis.

FIG. 14C also includes a graph 1450 showing a line 1453 showing airflow values on a Y-axis 1451, as a function of time t along an X-axis 1452.

The illustrations 1440 of cross sections 1441 1442 1443 1444 1445 of a throat and glottis show different states of the glottis and the graph 1450 shows corresponding airflow values to the above states.

By way of some examples, FIG. 14C shows:

a first location 1454 on the line 1453 corresponding to a closed glottis;

a second location 1455 on the line 1453 corresponding to an opening glottis;

a third location 1456 on the line 1453 corresponding to an open glottis; and a fourth location 1457 on the line 1453 corresponding to a closing glottis, the glottis at this location closing at a faster rate than the line 1453 shows for the glottis closing prior to location 1454.

a fifth location 1458 on the line 1453 corresponding to a closed glottis;

A glottal pulse is optionally extracted from the speech signal.

In some embodiments a glottal pulse calculation from a speech signal is optionally used for determining a heart rate condition. A first phase is optionally obtaining the glottal pulse.

In some embodiments the glottal pulse is optionally calculated as described in the above-mentioned article titled "Estimation of the glottal pulse from speech or singing voice".

In some embodiments one or more of the following parameters are calculated from the glottal pulse signal:

a glottal rise time (increase time from 10% to 90%);
a glottal fall time (decrease time from 90% down to 10%);
an open\close duration for the glottis;
a period (distance between peaks of the glottal pulse signal);
peak heights and/or widths of the glottal pulse signal; and
a spectrum of several periods of the glottal pulse signal.

In some embodiments statistics of the parameters are optionally compared, and a determination is optionally made of heart rate variability.

In some embodiments one or more of the above-mentioned parameters is/are used as "speech features" in the processing techniques described herein.

A potential advantage of using a glottal signal is that "natural" changes of speech organs that are not related to cardiac pulse (such as tongue and/or mouth movements), are potentially not considered, and potentially a more accurate estimation can be obtained.

Example for Spectral Analysis of Voice Features

Reference is now made to FIGS. 15A-15D, presenting determination of probability for heart rate pathology using spectral properties of voice features, in accordance with some embodiments of the invention, wherein FIGS. 15A and 15C show a healthy pattern, characterized in a high amplitude, low width peak, and FIGS. 15B and 15D illustrate AF pattern, characterized in a low amplitude, high width peak. The red circles indicate the spectral peak in heart-rate (that is calculated in method described earlier)

Since heart pulse is estimated to modulate the speech, different heartbeat rhythms are expected to create different patterns in the voice features spectral pattern. The bandwidth of the spectral peak is expected to match to the periodic extent of the cardiac parameter. For example, AF pulse is highly irregular and will create a variety of peaks in the spectral domain and hence will have a wider band-width. The peaks band-width will be relatively large, reflecting the non-periodic changes common for AF and other heart beat disorders. In comparison, regular pulse, i.e. periodic pulse, is expected to cause constant modulation of the speech, typically generating one main peak in the spectral domain, probably exactly in the heart rate. The peak is likely to be narrow to reflect a periodic change (e.g. a sinus type heart pulse).

The example shown in FIGS. 15A-15D is calculated using first derivatives of MFCC parameters. The derivative operation is potentially useful since it removes most of the "natural" (phonetic) speech information and content. It should be noted that this method can use autocorrelation coefficients alternatively or additionally to spectral analysis.

Exemplary overall Arrhythmia probability integration

In some embodiments, a calculated probability of irregularity in a heart pulse, for example as shown in FIG. 3, blocks 362-364 and FIG. 4A, blocks 460-466, is based on at least one of (i) voice feature distribution (ii) voice feature periodicity, (iii) pulse interval data.

Some heart pathologies typically manifest in a high heart rate. In some embodiments, a high heart rate is defined as higher than 70 BPM, or higher than 90 BPM, or higher than 100 BPM, or higher than 120 BPM. In some embodiments, for these pathologies, when a low and steady BPM is detected (e.g. high energy in the spectral domain concentrated around a single frequency), a lower probability for these specific pathologies can be estimated.

Optionally, a total variation of the series of pulse data intervals is calculated, for example using:

$$diff(i) = (T_{i+1} - T_i)/average(T_i)$$

$$TV = \sum_{i=1} diff(i)^2$$

time of heart pulse i: $T_i$. Distance between two pulses (RR) is: $|T_{i+1} - T_i|$ It was experimentally found that TV values of AF heart rate and normal heart rate have different values. This resulted in a threshold of AF detection based on a short series of Heart pulses (for example as exemplified in FIG. 11B, blocks 1122-1130, 1132)

In some embodiments, if the total variation exceeds a predetermined threshold, AF is detected. Optionally, for certain positive estimations (e.g. high probability for cardiac pathology) further medical checkup is recommended, for example, by sending the user a notification and/or notifying a caregiver.

In some embodiments, optionally for less certain estimations (e.g. medium probability for cardiac pathology) additional voice testing is initiated. In some embodiments, the subject is asked to pronounce some predetermined speech signals for further examination, Optionally using pre-selected speech sounds (such as, for example, long repetition 3-6 sec of voiced sounds—\ah\), to retrieve more information.

In some embodiments, for subjects exhibiting a low probability for cardiac pathology, data of the subject is stored, optionally for further analysis in subsequent testing, or for appending to the healthy training models database.

In some embodiments, once a probability to have a pathologic condition is established, the subject is referred to further diagnosis methods, potentially increasing the sensitivity of the detection. For example, a subject may be referred to have a hospital based checkup, and/or be referred to use complementary home-use applications, such as photoplethysmography (PPG) and/or a portable ECG monitor, which for example, could be used in a smartphone. In some embodiments, at the moment a condition is identified, the subject is notified to apply one of the complementary home-use applications, thereby increasing the likelihood for a correct diagnosis.

In some embodiments, complementary applications are manually operated. Optionally, the complementary applications are operated according to a predetermined regimen, for example, once a day, twice a day, three times a day and so forth, optionally according to the probability to suffer from a condition. For example, if a probability to have a condition is higher, then a higher number of complementary application operations is desired. Alternatively or additionally, complementary applications are operated immediately upon pathologic condition estimation.

Exemplary Treatment Monitoring

Reference is now made to FIG. 16, showing a timeline of a possible treatment and monitoring provided by the system and methods disclosed herein, in accordance with some embodiments of the invention.

In some embodiments, screening 1602 is provided to a large population of people or a single person. In some embodiments, following a determination of a cardiac condition in a sufficient predetermined probability, treatment is given. Alternatively or additionally, following a determination of a cardiac condition in a sufficient predetermined probability, a second diagnosis test is conducted, or a validation test, for example, such as ECG monitoring and/or photoplethysmography (PPG) and/or a second voice sample comprising a predetermined vocalization. Optionally, a treatment includes a pharmaceutical treatment 1630, typically ranging across a period of time. Alternatively or additionally, treatment includes a procedural treatment 1640 which is typically provided in a single occurrence.

In some embodiments, once a subject is about to begin treatment, at 1604 monitoring of his cardiac condition is provided before the treatment begins. Optionally, the severity of the condition is monitored and the treatment might change following such monitoring. Alternatively or additionally, at 1606 monitoring is provided during the treatment, optionally to monitor the effect of a medication. Alternatively or additionally, at 1608 monitoring is provided after a treatment, optionally, to identify relapse of the condition.

In some embodiments, monitoring schedule is based on the subject's diagnosed condition. For example, in a severe case of AF having atrial fibrillation for a few hours each day, sampling the subject once a day may be sufficient. On the other hand, if the subject is diagnosed with a mild case of AF, a more frequent sampling might be required to achieve detection.

General

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find calculated support in the following examples.

Examples

Example for Heart Condition Determination Using a Voice Sample

Reference is now made to the following example, which together with the above descriptions illustrates some embodiments of the invention in a non-limiting fashion.

In some embodiments, a human voice is sampled. In some embodiments, the voice sample is analyzed to extract desired voice segments. For example, silence periods may be taken out and/or only voiced segments are maintained. Optionally, only a specific kind of vowel is maintained, for example only /ah/ vowels, or only /eh/ vowels, or only /oh/ vowels, or only /uh/ vowels, or only /eeh/ vowels. In some embodiments, maintained voice segments are concatenated, potentially resulting in continuous data rather than following a time sequence. Alternatively, maintained voice segments keep their sequence over time, keeping the information of the timing of the segments.

In some embodiments, a voice feature, such as pitch, is extracted from voice segments which have been filtered to obtain voiced segments and concatenated. In some embodiments, natural fluctuations that are changes in phonation of the speech and changes due to natural fluctuation of the vocal cords and vocal cavities, of the pitch values are removed. In some embodiments the natural fluctuations are optionally filtered to achieve higher sensitivity in detecting heartbeat-related changes. In some embodiments, voice segments with adjusted pitch are concatenated after the natural fluctuations have been removed. Optionally, fusion points of consecutive voice segments are smoothed.

In some embodiments, the smoothed concatenated data of the pitch is analyzed to derive the normalized standard deviation (N-STD). In some embodiments, the value of the N-STD is compared to a threshold, above which the sampled subject is determined to have a pathologic cardiac condition and below which the sampled subject is determined to have a healthy cardiac condition.

In some embodiments, the same voice sample goes through a second analysis. Optionally, voice segments are extracted. In some embodiments, R pulses are identified in each maintained voice segment. Optionally, R pulses are extrapolated by identifying at least a portion of an R pulse consecutive to a removed voice segment. In some embodiments, RR intervals are calculated by locating consecutive R pulses. For example, by locating more than one R pulse in the same voice segment, and/or by locating R pulses on different voice segments having a short gap that can be neglected, and/or by identifying an R pulse consecutive to an extrapolated pulse.

In some embodiments, RR intervals are compared to a reference, for example, a reference having RR intervals known to be characteristic of a pathologic cardiac condition, such as AF. Alternatively or additionally, a reference includes a healthy RR interval sequence of the same sampled subject. Alternatively or additionally, a reference includes samples of different healthy and/or pathologic subjects.

In some embodiments, the probability of the RR interval sequence to match a reference is compared to a threshold. For example, if a probability of an RR interval is above a threshold when compared to a pathologic sequence, and/or below the threshold when compared to a healthy sequence, a pathologic condition is determined. Alternatively or additionally, if a probability of an RR interval is below a threshold when compared to a pathologic sequence, and/or above the threshold when compared to a healthy sequence, a healthy condition is determined.

In some embodiments, the voice sample goes through a third analysis. It should be noted that the order of conducting the analysis can be varied, and each analysis may be conducted at an independent manner from the other two analyses, in combination or alone.

In some embodiments, a voice sample is analyzed to extract voice features. In some embodiments, heart rate is determined, optionally by extracting the heart rate from the voice sample itself. In some embodiments, an autocorrelation and\or spectrum of the voice feature at the heart rate frequency is calculated. It is noted that blood flowing into and out of the vocal region is probably associated with the heart pulse. It is estimated that at least a portion of the variability of a voice feature would be influenced by this flow of blood and/or the ventricular beat and/or atrial beat. Therefore, if there is a healthy periodic heart rate, it is estimated that an autocorrelation analysis at the heart rate and\or spectral analysis would provide a peak shape which is indicative of a high periodicity of vocal blood influence at the heart rate. On the other hand, if there is arrhythmia, an autocorrelation at the heart rate would provide a smeared peak, indicative that blood influence is not very periodic.

In some embodiments, a parameter of the peak shape is compared to a threshold. For example, a parameter of the peak shape may include its bandwidth, and/or height and/or total area of the peak. In some embodiments, a peak shape parameter is compared to a threshold to determine a healthy or pathologic cardiac condition.

In some embodiments, a weighted probability for healthy and/or pathologic cardiac condition based on the above analyses is calculated.

In some embodiments, chronic conditions are potentially detected by changes in voice parameters. In some cases Atrial Fibrillation (AF) causes expansion of the Left Atrium (which happens in a majority of pathologic AF cases). The expansion impacts the recurrent laryngeal nerve, causing constant changes of the voice. The changes are potentially manifested in the parameters of the pitch signals and can be analyzed and detected.

This enables to detect AF patients with chronic conditions even in instances where the heart beats at a normal rate.

Example for Heart Rate Extraction

Reference is now made to FIG. 17, illustrating an example for heart rate extraction from a voice sample, in accordance with some embodiments of the invention. Voice features that are correlated to the heart beat are estimated to have peak value at frequency of the heartbeat. For example, FIG. 17 exemplifies an analysis of a speech sample of \ah\ sound, of a subject having 74 BPM. The chosen voice feature for the analysis is dMFCC: absolute value of first derivative of MFCC vector High energy (peak) at 0.84 Hz which is 74 bpm.

After deriving voice features from each frame, in some embodiments, periodic patterns of at least one voice feature are identified in a sequence over time of the voice feature. For example, identification of periodic patterns may be conducted using spectral analysis and/or autocorrelation analysis. In some embodiments, heart-rate in beats per minute (BPM), optionally maximal, is estimated from the identified periodic patterns.

Various embodiments and aspects of the present invention as delineated hereinabove and as claimed in the claims section below find experimental and calculated support in the following examples.

EXAMPLES

Reference is now made to the following examples, which together with the above descriptions illustrate some embodiments of the invention in a non-limiting fashion.

An IRB-approved clinical study has been conducted with AF patients in AF conditions and in normal heart rate conditions at a leading medical center in Israel.

Of 58 AF patients, 26 underwent cardioversion and were recorded twice (a) during an AF episode and (b) during normal heart rate condition two hours post-cardioversion. Cardioversion is a medical procedure by which an abnormally fast heart rate or other cardiac arrhythmia is converted to normal rhythm using electricity or drugs. The following table summarizes the number of ECG/voice recorded pairs that have been collected to date:

| Group | Number of patients |
|---|---|
| Same patients in AS and in normal heart rate conditions (pre- and post-cardioversion) | 32 |
| AF patients (total) | 58 |
| Subjects in normal heart rate condition | 23 |

Reference is now made to FIG. 18A, which is a graph showing speaker-independent detection results in accordance with some embodiments of the invention.

FIG. 18A shows a graph 1801 of an experiment where recordings of 58 patients having an AF condition and 23 patients having a normal heart rhythm (sinus rhythm) were analyzed by an example embodiment of the invention at different thresholds of decision for AF or normal heart rhythm.

The graph 1801 has an X-axis 1802 corresponding to a qualitative value of the threshold, and a Y-axis 1803 corresponding to a portion, in a range of 0 to 1, of the patient recordings where the patient's condition is analyzed correctly.

FIG. 18A shows a first line 1804 of true positive (having AF condition) cardiac condition classification, and a second line 1805 of true negative (sinus rhythm) cardiac condition classification.

FIG. 18A also shows two example points where a same specific threshold value provides results which are specifically described now: a first point 1806 showing 92% true positive identification of AF based on voice analysis, and a second point 1807 showing 70% true negative identification of AF, that is identification as normal sinus rhythm, based on voice analysis.

FIG. 18A shows speaker-independent results, that is, results of a system trained on a large number of speakers and used to detect cardiac condition on an unknown patient. The results shown are considered as successful in estimating cardiac conditions based on human voice.

Reference is now made to FIG. 18B, which is a graph showing speaker-dependent detection results in accordance with some embodiments of the invention.

FIG. 18B shows a graph 1811 of an experiment where recordings of 32 patients having an AF condition who were recorded under AF conditions and also under normal sinus rhythm conditions, analyzed by an example embodiment of the invention at different thresholds of decision for AF or normal heart rhythm.

The graph 1811 has an X-axis 1812 corresponding to a qualitative value of the threshold, and a Y-axis 1813 corresponding to a portion of the patient recordings where the patient's condition is analyzed correctly.

FIG. 18B shows a first line 1814 of true positive (having AF condition) cardiac condition classification, and a second line 1815 of true negative (sinus rhythm) cardiac condition classification.

FIG. 18B also shows two example points where a same specific threshold value provides results which are specifically described now: a first point 1816 showing 92% true negative (sinus rhythm) identification of AF based on voice analysis, and a second point 1817 showing 77% true positive identification of AF, that is identification as AF rhythm, based on voice analysis.

FIG. 18B shows speaker-dependent results, that is, results of a system trained by one or more voice recording(s) of a single speaker, taken in specific known heart conditions, healthy or AF, used to detect cardiac condition on the same speaker. The results shown are considered as successful in estimating cardiac conditions based on human voice.

Comparative Benchmarks

An estimation is now made of an amount of time it would take a single time-point ECG device (or an event recorder) used on an opportunistic basis, such as once a week, to capture an AF episode compared to some embodiments of the invention. The table below summarizes the results of the calculations when running a simulation under different AF burden and testing frequency scenarios, A simulator was configured to register AF detection when the AF voice biomarker is detected in at least two samples of non-spontaneous speech. In such a configuration, embodiment of the invention resulted in detection sensitivity (true positive) of 94% and a detection specificity (true negative detection of sinus rhythm) of 92%.

As shown in the table below, based on an AF burden of six 10-minute episodes per day, the simulation has shown that an ECG-based weekly monitoring will detect the AF within 163 days, whereas the embodiment of the invention will detect the AF within 8 days.

| | AF Scenario | | ECG | | embodiment | |
|---|---|---|---|---|---|---|
| # | Burden (mins/day) | Episode duration (mins) | Frequency | Days to Detect AF | Frequency | Days to Detect AF |
| 1 | 60 | 10 | 1/week | 163 | 5 calls per day × 4 minutes each | 8 |
| 2 | 15 | 5 | 1/week | 546 | 5 calls per day × 4 minutes each | 29 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for analyzing a voice sample of a subject to determine a cardiac condition, comprising:
receiving a voice sample;
extracting at least one voice feature from the voice sample;
analyzing said voice feature to detect an effect of a blood flow on said at least one voice feature, said effect being at least one of a timing of said blood flow, a periodicity of said blood flow and a magnitude or change in magnitude of said blood flow;
determining a pathological cardiac condition based on said effect.

2. The method according to claim 1, further comprising classifying said voice sample to identify voiced segments and concatenating said voiced segments, such that at least some segments are removed and remaining segment ends are smoothed.

3. The method according to claim 1, wherein said analyzing said voice feature to detect an effect of said blood flow on said at least one voice feature comprises detecting an effect of said blood flow as effected by at least one cause affecting voice selected from a group consisting of:
ventricular beat; and
atrial beat
on said at least one voice feature.

4. The method according to claim 1, wherein said determined cardiac condition comprises a cardiac condition selected from a group consisting of:
an abnormal heart rate;
an arrhythmic heart rate;
ventricle tachycardia;
ectopic beats;
premature ventricular contraction;
cardiac fibrillation; and
atrial fibrillation.

5. The method according to claim 1, comprising determining a presence of an arrhythmic cardiac condition when identifying more than a predetermined number of occurrences of cardiac fibrillation.

6. The method according to claim 1, wherein detecting an effect of a blood flow on said at least one voice feature comprises classifying one or more parameters of said cardiac behavior based on said detected effect, and said one or more parameters comprise a pulse wave shape.

7. The method according to claim 3, wherein said detecting an effect comprises identifying an effect of at least one of a timing of said cause affecting voice, a periodicity of said cause affecting voice and a magnitude or change in magnitude of said cause affecting voice.

8. The method according to claim 1, wherein said determining a pathological cardiac condition comprises;
calculating time intervals between consecutive occurrences of heart pulses;
matching said time intervals with reference time intervals obtained from a reference heart condition;
determining a probability of said matching; and
comparing said probability to a threshold for determining said pathological cardiac condition.

9. The method according to claim 1, wherein said detecting an effect comprises identifying three occurrences of heart pulses and said three occurrences of a heart pulse are not identified in the same voiced segment.

10. The method according to claim 1, wherein said detected effect comprises an effect of a magnitude, or a change in a magnitude of a heart pulse.

11. The method according to claim 1, wherein:
said detecting an effect comprises calculating a distribution of a plurality of values of said at least one voice feature; and
said determining said pathological cardiac condition based on said effect comprises comparing a characterizing parameter of said distribution to a threshold.

12. The method according to claim 1, further comprising validating said determining a cardiac condition and wherein said cardiac condition comprises a cardiac condition selected from a group consisting of:
an arrhythmic cardiac condition; and
atrial fibrillation.

13. The method according to claim 1, wherein extracting the voice feature comprises performing cross coherence between a first segment of the voice sample and a second segment of the voice sample.

14. The method according to claim 1, wherein extracting the voice feature comprises performing analysis of the speech signal selected from a group consisting of:
wavelet analysis;
Mel Frequency Cepstral Coefficient (MFCC) analysis;
glottal pulse analysis; and
Linear Predictive Coding (LPC) analysis.

15. The method according to claim 1, wherein said method comprises receiving, extracting, analyzing and determining a pathological cardiac condition when said voice sample comprises a voice sample of spontaneous speech.

16. The method according to claim 1, wherein said pathological cardiac condition comprises an irregular heartbeat.

17. A system for determining a cardiac condition in a voice sample provided by a subject, comprising:
a voice input for obtaining a digital voice sample of said voice sample;
a voice feature extractor that extracts at least one voice feature from said digital voice sample;
a voice feature processor that identifies an effect of a cardiac condition on said at least one voice feature; and
a cardiac condition classifier that determines the cardiac condition based on said effect,
wherein said system is configured to:
extract said at least one voice feature from said digital voice sample;
analyze said voice feature to identify an effect of a cardiac condition on said at least one voice feature; and
determine a pathological cardiac condition based on said effect.

18. The system according to claim 17, wherein said voice input forms a part of at least one of a mobile phone, digital assistant and a car multimedia system.

19. The system according to claim 17, further comprising a permanent memory, wherein:
said permanent memory stores at least one previously collected voice sample from said subject; and
said cardiac condition classifier determines said cardiac condition based on a change between said previously collected voice samples and said digital voice sample.

20. The system according to claim 17, wherein said system is configured to extract, analyze and determine a pathological cardiac condition when said digital voice sample comprises a digital voice sample of spontaneous speech.

21. The system according to claim 17, wherein said pathological cardiac condition comprises an irregular heartbeat.

* * * * *